(12) United States Patent
Finney et al.

(10) Patent No.: US 10,358,493 B2
(45) Date of Patent: Jul. 23, 2019

(54) BISPECIFIC FORMAT SUITABLE FOR USE IN HIGH-THROUGH-PUT SCREENING

(71) Applicant: UCB BIOPHARMA SPRL, Brussels (BE)

(72) Inventors: Helene Margaret Finney, Slough (GB); Stephen Edward Rapecki, Slough (GB); Michael John Wright, Slough (GB)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

(21) Appl. No.: 15/311,198

(22) PCT Filed: May 28, 2015

(86) PCT No.: PCT/EP2015/061819
§ 371 (c)(1),
(2) Date: Nov. 15, 2016

(87) PCT Pub. No.: WO2015/181282
PCT Pub. Date: Dec. 3, 2015

(65) Prior Publication Data
US 2017/0081404 A1    Mar. 23, 2017

(30) Foreign Application Priority Data

May 29, 2014 (GB) .................................. 1409558.2

(51) Int. Cl.
| C07K 16/00 | (2006.01) |
| C07K 16/28 | (2006.01) |
| C07K 16/14 | (2006.01) |
| C07K 16/46 | (2006.01) |
| G01N 33/68 | (2006.01) |

(52) U.S. Cl.
CPC .............. C07K 16/28 (2013.01); C07K 16/00 (2013.01); C07K 16/14 (2013.01); C07K 16/468 (2013.01); G01N 33/6854 (2013.01); C07K 2317/31 (2013.01); C07K 2317/55 (2013.01); C07K 2317/622 (2013.01); C07K 2317/76 (2013.01); C07K 2317/92 (2013.01); C07K 2319/00 (2013.01)

(58) Field of Classification Search
CPC ........ C07K 16/00; C07K 16/28; C07K 16/14; C07K 16/468
USPC .................. 424/133.1, 136.1, 178.1
See application file for complete search history.

(56) References Cited

U.S. PATENT DOCUMENTS

| 4,741,900 A | 5/1988 | Alvarez et al. |
| 5,223,409 A | 6/1993 | Ladner et al. |
| 5,403,484 A | 4/1995 | Ladner et al. |
| 5,427,908 A | 6/1995 | Dower et al. |
| 5,516,637 A | 5/1996 | Huang et al. |
| 5,545,806 A | 8/1996 | Lonberg et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,658,727 A | 8/1997 | Barbas et al. |
| 5,661,016 A | 8/1997 | Lonberg et al. |
| 5,698,426 A | 12/1997 | Huse |
| 5,731,168 A | 3/1998 | Carter et al. |
| 5,733,743 A | 3/1998 | Johnson et al. |
| 5,750,753 A | 5/1998 | Kimae et al. |
| 5,770,429 A | 6/1998 | Lonberg et al. |
| 5,780,225 A | 7/1998 | Wigler et al. |
| 5,798,229 A | 8/1998 | Strittmatter et al. |
| 5,821,047 A | 10/1998 | Garrard et al. |
| 5,969,108 A | 10/1999 | McCafferty et al. |
| 6,010,902 A | 1/2000 | Ledbetter et al. |
| 6,106,834 A | 8/2000 | Lazarovits et al. |
| 7,183,076 B2 | 2/2007 | Arathoon et al. |
| 8,088,378 B2 | 1/2012 | Chen et al. |
| 8,409,577 B2 | 4/2013 | Thompson et al. |
| 2003/0027247 A1 | 2/2003 | Wang et al. |
| 2003/0202975 A1 | 10/2003 | Tedder |
| 2005/0033031 A1 | 2/2005 | Couto |
| 2005/0048578 A1 | 3/2005 | Zhang |
| 2006/0252130 A1 | 11/2006 | Boehm et al. |
| 2007/0141672 A1 | 6/2007 | Shin |
| 2011/0076270 A1 | 3/2011 | Aversa et al. |

(Continued)

FOREIGN PATENT DOCUMENTS

| EP | 0392745 A2 | 10/1990 |
| EP | 0438474 B1 | 5/1996 |

(Continued)

OTHER PUBLICATIONS

Ward et al. (Nature 341:544-546 (1989)).*
Dmitrova, M. et al. "A new LexA-based genetic system for monitoring and analyzing protein heterodimerization in *Escherichia coli*" Molecular and General Genetics, Feb. 1998, pp. 205-212, vol. 257.

(Continued)

*Primary Examiner* — Lynn A Bristol
(74) *Attorney, Agent, or Firm* — Medler Ferro Woodhouse & Mills PLLC

(57) ABSTRACT

The present disclosure relates to a novel bispecific protein complex and a method of using the complexes to screen for synergistic or novel biological function. The bispecific format is particularly suitable for high-throughput screening because all of its components can be expressed from cells as individual units and the units can be assembled simply by mixing without employing conjugation or coupling chemistry.

9 Claims, 35 Drawing Sheets
Specification includes a Sequence Listing.

(56) References Cited

U.S. PATENT DOCUMENTS

| | | | |
|---|---|---|---|
| 2013/0209463 A1 | 8/2013 | Rotman et al. | |
| 2013/0336977 A1 | 12/2013 | Thompson et al. | |
| 2014/0099254 A1 | 4/2014 | Chang et al. | |
| 2014/0212425 A1 | 7/2014 | Chang et al. | |
| 2015/0239974 A1 | 8/2015 | Chang et al. | |
| 2017/0204178 A1 | 7/2017 | Finney et al. | |
| 2017/0204183 A1 | 7/2017 | Finney et al. | |
| 2018/0201678 A1 | 7/2018 | Finney et al. | |
| 2018/0334513 A1* | 11/2018 | Wright | C07K 16/00 |
| 2018/0334514 A1* | 11/2018 | Wright | C07K 16/00 |
| 2018/0346603 A1* | 12/2018 | Bhatta | C07K 16/00 |
| 2018/0355063 A1* | 12/2018 | Finney | C07K 16/468 |

FOREIGN PATENT DOCUMENTS

| | | |
|---|---|---|
| EP | 0463151 B1 | 6/1996 |
| EP | 0546073 B1 | 9/1997 |
| EP | 1242457 B1 | 8/2004 |
| EP | 1570267 B1 | 10/2011 |
| EP | 2706069 A1 | 3/2014 |
| WO | WO86/01533 A1 | 3/1986 |
| WO | WO89/00195 A1 | 1/1989 |
| WO | WO89/01476 A1 | 2/1989 |
| WO | WO90/02809 A1 | 3/1990 |
| WO | WO91/09967 A1 | 7/1991 |
| WO | WO91/10737 A1 | 7/1991 |
| WO | WO92/01047 A1 | 1/1992 |
| WO | WO92/02551 A1 | 2/1992 |
| WO | WO92/18619 A1 | 10/1992 |
| WO | WO92/22583 A1 | 12/1992 |
| WO | WO93/06231 A1 | 4/1993 |
| WO | WO 93/11162 | 6/1993 |
| WO | WO93/11236 A1 | 6/1993 |
| WO | WO95/15982 A1 | 6/1995 |
| WO | WO95/20401 A1 | 8/1995 |
| WO | WO 96/26964 | 9/1996 |
| WO | WO98/20734 A1 | 5/1998 |
| WO | WO 02/072832 | 9/2002 |
| WO | WO 03/012069 | 2/2003 |
| WO | WO03/031581 A2 | 4/2003 |
| WO | WO03/048327 A2 | 6/2003 |
| WO | WO 03/093320 | 11/2003 |
| WO | WO2004/039840 A1 | 5/2004 |
| WO | WO2004/051268 A1 | 6/2004 |
| WO | WO 2004/081051 | 9/2004 |
| WO | WO2004/106377 A1 | 12/2004 |
| WO | WO2005/003169 A2 | 1/2005 |
| WO | WO2005/003170 A2 | 1/2005 |
| WO | WO2005/003171 A2 | 1/2005 |
| WO | WO 2005/006210 | 1/2005 |
| WO | WO2005/026210 A2 | 3/2005 |
| WO | WO2005/113605 A1 | 12/2005 |
| WO | WO2005/117984 A2 | 12/2005 |
| WO | WO2005/118642 A2 | 12/2005 |
| WO | WO2006/004910 A2 | 1/2006 |
| WO | WO 2006/119897 | 11/2006 |
| WO | WO2007/060406 A1 | 5/2007 |
| WO | WO 2007/085837 | 8/2007 |
| WO | WO2007/087453 A2 | 8/2007 |
| WO | WO 2007/146968 | 12/2007 |
| WO | WO 2008/070569 | 6/2008 |
| WO | WO 2008/119353 | 10/2008 |
| WO | WO2009/012268 A1 | 1/2009 |
| WO | WO2009/040562 A1 | 4/2009 |
| WO | WO2010/035012 A1 | 4/2010 |
| WO | WO 2011/025904 | 3/2011 |
| WO | WO2011/061492 A2 | 5/2011 |
| WO | WO2011/086091 A1 | 7/2011 |
| WO | WO2011/130305 A2 | 10/2011 |
| WO | WO2011/131746 A2 | 10/2011 |
| WO | WO2012/023053 A2 | 2/2012 |
| WO | WO 2012/116453 | 9/2012 |
| WO | WO2012/151199 A1 | 11/2012 |
| WO | WO 2012/162561 | 11/2012 |
| WO | WO2013/060867 A2 | 5/2013 |
| WO | WO2013/078455 A2 | 5/2013 |
| WO | WO 2013/085893 | 6/2013 |
| WO | WO 2014/001326 | 1/2014 |
| WO | WO2014/011518 A1 | 1/2014 |
| WO | WO 2014/011519 | 1/2014 |
| WO | WO2014/011520 A1 | 1/2014 |
| WO | WO 2014/011521 | 1/2014 |
| WO | WO2014/096390 A1 | 6/2014 |
| WO | WO2014/131694 A1 | 9/2014 |
| WO | WO2015/021089 A1 | 2/2015 |
| WO | WO 2015/057834 | 4/2015 |
| WO | WO2015/181282 A1 | 12/2015 |
| WO | WO2015/197772 A1 | 12/2015 |
| WO | WO2015/197789 A1 | 12/2015 |
| WO | WO 2016/009029 | 1/2016 |
| WO | WO 2016/009030 | 1/2016 |
| WO | WO 2016/168773 | 10/2016 |
| WO | WO2017/009473 A1 | 1/2017 |
| WO | WO2017/009476 A1 | 1/2017 |
| WO | WO2017/093402 A1 | 6/2017 |
| WO | WO2017/093404 A1 | 6/2017 |
| WO | WO2017/093406 A1 | 6/2017 |
| WO | WO2017/093408 A1 | 6/2017 |
| WO | WO2017/093410 A1 | 6/2017 |

OTHER PUBLICATIONS

Larsen Spang, H. C. et al. "Heterodimeric Barnase-Barstar Vaccine Molecules: Influence of One Versus Two Targeting Units Specific for Antigen Presenting Cells" *PLoS One*, Sep. 18, 2012, pp. 1-13, vol. 7, No. 9.

Rodgers, D. T. et al. "Switch-mediated activation and retargeting of CAR-T cells for B-cell malignancies" *Proceedings of the National Academy of Sciences of the United States of America*, Jan. 12, 2016, pp. E459-E468.

Schoonjans, R. et al. "A new model for intermediate molecular weight recombinant bispecific and trispecific antibodies by efficient heterodimerization of single chain variable domains through fusion to a Fab-chain" *Biomolecular Engineering*, Jun. 1, 2001, pp. 193-202, vol. 17, No. 6.

Veri M-C. et al. "Therapeutic Control of B Cell Activation Via Recruitment of Fcγ Receptor IIb (CD32B) Inhibitory Function With a Novel Bispecific Antibody Scaffold" *Arthritis & Rheumatism*, Jul. 2010, pp. 1933-1943, vol. 62, No. 7.

Wang, X. et al. "Antibody Engineering Using Phage Display with a Coiled-Coil Heterodimeric Fv Antibody Fragment" *PLoS One*, Apr. 28, 2011, pp. 1-10, vol. 6, No. 4.

Willcox, B. E. et al. "Production of soluble αβ T-cell receptor heterodimers suitable for biophysical analysis of ligand binding" *Protein Science*, 1999, pp. 2418-2423, vol. 8.

Goldenberg, D. M. et al. "Multifunctional Antibodies by the Dock-and-Lock Method for Improved Cancer Imaging and Therapy by Pretargeting" *The Journal of Nuclear Medicine*, Jan. 1, 2008, pp. 158-163, vol. 49, No. 1.

Kontermann, R. "Dual targeting strategies with bispecific antibodies" *mAbs*, Mar. 1, 2012, pp. 182-197, vol. 4, No. 2.

Written Opinion in International Application No. PCT/EP2015/061819, dated Aug. 3, 2015, pp. 1-7.

Arndt, C. et al. "Costimulation improves the killing capability of T cells redirected to tumor cells expressing low levels of CD33: description of a novel modular targeting system" *Leukemia*, 2014, pp. 59-69, vol. 28, No. 1.

Campbell, J. D. M. et al. "Rapid detection, enrichment and propagation of specific T cell subsets based on cytokine secretion" *Clinical and Experimental Immunology*, 2010, pp. 1-10, vol. 163, No. 1.

Carnahan, J. et al. "Epratuzumab, a CD22-targeting recombinant humanized antibody with a different mode of action from rituximab" *Molecular Immunology*, 2007, pp. 1331-1341, vol. 44, No. 6.

Doerner, A. et al. "Therapeutic antibody engineering by high efficiency cell screening" *FEBS Letters*, 2014, pp. 278-287, vol. 588, No. 2.

Gold, M. R. et al. "The B Cell Antigen Receptor Activates the Akt (Protein Kinase B)/Glycogen Synthase Kinase-3 Signaling Pathway Via Phosphatidylinositol 3-Kinase" *The Journal of Immunology*, 1999, pp. 1894-1905, vol. 163.

(56) References Cited

OTHER PUBLICATIONS

Hanes, J. et al. "Ribosome display efficiently selects and evolves high-affinity antibodies in vitro from immune libraries" *Proc. Natl. Acad. Sci.*, Nov. 1998, pp. 14130-14135, vol. 95, No. 24.
Ko, S. et al. "Engineering Antibodies for Dual Specificity and Enhanced Potency" *Biotechnology and Bioprocess Engineering*, 2015, pp. 201-210, vol. 20, No. 2.
Luo, H. et al. "Design and Applications of Bispecific Heterodimers: Molecular Imaging and beyond" *Molecular Pharmaceutics*, Apr. 16, 2014, pp. 1750-1761, vol. 11, No. 6.
Pfeifer, M. et al. "Anti-CD22 and anti-CD79B antibody drug conjugates are active in different molecular diffuse large B-cell lymphoma subtypes" *Leukemia*, May 8, 2015, pp. 1578-1586, vol. 29, No. 7.
Zahnd, C. et al. "Directed in Vitro Evolution and Crystallographic Analysis of a Peptide-binding Single Chain Antibody Fragment (scFv) with Low Picomolar Affinity" *The Journal of Biological Chemistry*, Apr. 30, 2004, pp. 18870-18877, vol. 279, No. 18.
Adair et al., "Therapeutic Antibodies," Drug Design Reviews Online 2(3):209-217 (2005).
Altschul et al., "Basic local alignment search tool," J Mol Biol 215(3):403-410 (1990).
Altschul et al., "Gapped BLAST and PSI-BLAST: a new generation of protein database search programs," Nucleic Acids Res 25(17):3389-3402 (1997).
Ames et al., "Conversion of murine Fabs isolated from a combinatorial phage display library to full length immunoglobulins," J Immunol Methods 184(2):177-186 (1995).
Angal et al., "A single amino acid substitution abolishes the heterogeneity of chimeric mouse/human (IgG4) antibody," Mol Immunol 30(1):105-108 (1993).
Armour et al., "Recombinant human IgG molecules lacking Fcgamma receptor 1 binding and monocyte triggering activities," Eur J Immunol 29(8):2613-2624 (1999).
Babcook et al., "A novel strategy for generating monoclonal antibodies from single, isolated lymphocytes producing antibodies of defined specificities," Proc Natl Acad Sci USA 93(15):7843-7848 (1996).
Bartalena et al., "Thyroid hormone transport proteins," Clin Lab Med 13(3):583-598 (1993).
Berger et al., "Antigen recognition by conformational selection," FEBS Lett 450:149-153 (1999).
Bradshaw et al., "Concurrent detection of secreted products from human lymphocytes by microengraving: cytokines and antigen-reactive antibodies," Clin Immunol 129(1):10-18 (2008).
Bree et al., "Pharmacokinetics of intravenously administered 125I-labelled human alpha 1-acid glycoprotein," Clin Pharmacokinet 11(4):336-342 (1986).
Brinkmann et al., "Phage display of disulfide-stabilized Fv fragments," J Immunol Methods 182(1):41-50 (1995).
Brosterhus et al., "Enrichment and detection of live antigen-specific CD4(+) and CD8(+) T cells based on cytokine secretion," Eur J Immunol 29(12):4053-4059 (1999).
Bruhns et al., "Specificity and affinity of human Fcgamma receptors and their polymorphic variants for human IgG subclasses," Blood 113(16):3716-3725 (2009).
Burton et al., "Human antibodies from combinatorial libraries," Adv Immunol 57:191-280 (1994).
Caldas et al., "Humanization of the anti-CD18 antibody 6.7: an unexpected effect of a framework residue in binding to antigen," Mol Immunol 39:941-952 (2003).
Casset et al., "A peptide mimetic of an anti-CD4 monoclonal antibody by rational design," Biochem Biophys Res Comm 307:198-205 (2003).
Chan et al., "Therapeutic antibodies for autoimmunity and inflammation," Nat Rev Immunol 10(5):301-316 (2010).
Chang et al., "Loop-Sequence Features and Stability Determinants in Antibody Variable Domains by High-Throughput Experiments," Structure 22:9-21 (2014).

Chen et al., "Enhancement and destruction of antibody function by somatic mutation: unequal occurrence is controlled by V gene combinatorial associations," EMBO J 14(12):2784-2794 (1995).
Chien et al., "Significant structural and functional change of an antigen-binding site by a distant amino acid substitution: Proposal of a structural mechanism," Proc Natl Acad Sci USA 86:5532-5536 (1989).
Chothia et al., "Canonical structures for the hypervariable regions of immunoglobulins," J Mol Biol 196(4):901-917 (1987).
Chu et al., "Suppression of rheumatoid arthritis B cells by XmAb5871, an anti-CD19 antibody that coengages B cell antigen receptor complex and Fcγ receptor IIb inhibitory receptor," Arthritis Rheumatol 66:1153-1164 (2014).
Clargo et al., "The rapid generation of recombinant functional monoclonal antibodies from individual, antigen-specific bone marrow-derived plasma cells isolated using a novel fluorescence-based method," MAbs 6(1):143-159 (2014).
Crameri et al., "DNA shuffling of a family of genes from diverse species accelerates directed evolution," Nature 391:288-291 (1998).
Czerwinski et al., "Construction of dimeric F(ab) useful in blood group serology," Transfusion 42(2):257-264 (2002).
Datta-Mannan et al., "Humanized IgG1 variants with differential binding properties to the neonatal Fc receptor: relationship to pharmacokinetics in mice and primates," Drug Metab Dispos 35(1):86-94 (2007).
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J Immunol 169:3076-3084 (2002).
Dennis et al., "Albumin Binding as a General Strategy for Improving the Pharmacokinetics of Proteins," J Biol Chem 277(38):35035-35043 (2002).
Dubowchik et al., "Receptor-mediated and enzyme-dependent targeting of cytotoxic anticancer drugs," Pharmacol Ther 83(2):67-123 (1999).
Dunkin et al., "Immune cell therapy in IBD," Dig Dis 32:61-66 (2014).
Feldman et al., "Adoptive Cell Therapy—Tumor-Infiltrating Lymphocytes, T-Cell Receptors, and Chimeric Antigen Receptors," Semin Oncol 42(4):626-639 (2015).
Finney et al., "Chimeric receptors providing both primary and costimulatory signaling in T cells from a single gene product," J Immunol 161:2791-2797 (1998).
Gish et al., "Identification of protein coding regions by database similarity search," Nat Genet 3(3):266-272 (1993).
Gitlin et al., "The selectivity of the human placenta in the transer of plasma proteins from mother to fetus," J Clin Invest 43:1938-1951 (1964).
Giusti et al., "Somatic diversification of S107 from an antiphosphocoline to an anti-DNA autoantibody is due to a single base change in its heavy chain variable region," Proc Natl Acad Sci USA 84:2926-2930 (1987).
Glockshuber et al., "A comparison of strategies to stabilize immunoglobulin Fv-fragments," Biochemistry 29(6):1362-1367 (1990).
Gussow et al., "Humanization of Monoclonal Antibodies," Meth Enzymol 203:99-121 (1991).
Harris, "Processing of C-terminal lysine and arginine residues of proteins isolated from mammalian cell culture," J Chromatogr A 705(1):129-134 (1995).
Hermiston et al., "CD45: A Critical Regulator of Signaling Thresholds in Immune Cells," Ann Rev Immunol 21:107-137 (2003).
Hinnebusch, "Evidence for translational regulation of the activator of general amino acid control in yeast," Proc Natl Acad Sci USA 81:6442-6446 (1984).
Hinton et al., "Engineered human IgG antibodies with longer serum half-lives in primates," J Biol Chem 279(8):6213-6216 (2004).
Hollinger et al., "Engineered antibody fragments and the rise of single domains," Nat Biotechnol 23(9):1126-1136 (2005).
Holm et al., "Functional mapping and single chain construction of the anti-cytokeratin 8 monoclonal antibody Tsl1 ," Mol Immunol 44:1075-1084 (2007).
Holmes, "Buy buy bispecific antibodies," Nat Rev Drug Discov 10(11):798-800 (2011).

(56) References Cited

OTHER PUBLICATIONS

Holt et al., "Anti-serum albumin domain antibodies for extending the half-lives of short lived drugs," Protein Eng Des Sel 21(5):283-288 (2008).
Hope et al., "GCN4 protein, synthesized in vitro, binds HIS3 regulatory sequences: implications for general control of amino acid biosynthetic genes in yeast," Cell 43(1):177-188 (1985).
Idusogie et al., "Mapping of the C1q binding site on rituxan, a chimeric antibody with a human IgG1 Fc," J Immunol 164(8):4178-1484 (2000).
Idusogie et al., "Engineered antibodies with increased activity to recruit complement," J Immunol 166(4):2571-2575 (2001).
Jourdan et al., "An in vitro model of differentiation of memory B cells into plasmablasts and plasma cells including detailed phenotypic and molecular characterization," Blood 114(25):5173-5181 (2009).
Jung et al., "Design of interchain disulfide bonds in the framework region of the Fv fragment of the monoclonal antibody B3," Proteins 19(1):35-47 (1994).
Karnell et al., "CD19 and CD32b Differentially Regulate Human B Cell Responsiveness," J Immunol 192(4):1480-1490 (2014).
Kashmiri et al., "SDR grafting—a new approach to antibody humanization," Methods 36(1):25-34 (2005).
Keller et al., "Independent Metalloregulation of Ace1 and Mac1 in *Saccharomyces cerevisiae*," Eukaryot Cell 4(11):1863-1871 (2005).
Kettleborough et al., "Isolation of tumor cell-specific single-chain Fv from immunized mice using phage-antibody libraries and the re-construction of whole antibodies from these antibody fragments," Eur J Immunol 24(4):952-958 (1994).
Kohler et al., "Continuous cultures of fused cells secreting antibody of predefined specificity," Nature 256:495-497 (1975).
Kozbor et al., "The production of monoclonal antibodies from human lymphocytes," Immunol Today 4(3):72-79 (1983).
Kudo et al., "T lymphocytes expressing a CD16 signaling receptor exert antibody-dependent cancer cell killing," Cancer Res 74(1):93-103 (2014).
Labrijn et al., "Therapeutic IgG4 antibodies engage in Fab-arm exchange with endogenous human IgG4 in vivo," Nat Biotechnol 27(8):767-771 (2009).
Lazar et al., "Engineered antibody Fc variants with enhanced effector function," Proc Natl Acad Sci USA 103(11):4005-4010 (2006).
Love et al., "A microengraving method for rapid selection of single cells producing antigen-specific antibodies," Nat Biotechnol 24(6):703-707 (2006).
Low et al., "Mimicking Somatic Hypermutation: Affinity Maturation of Antibodies Displayed on Bacteriophage Using a Bacterial Mutator Strain," J Mol Biol 260(3):359-368 (1996).
Luo et al., "Vl-linker-Vh orientation-dependent expression of single chain Fv-containing an engineered disulfide-stabilized bond in the framework regions," J Biochem 118(4):825-831 (1995).
MacCallum et al., "Antibody-antigen Interactions: Contact Analysis and Binding Site Topography," J Mol Biol 262:732-745 (1996).
Madden et al., "Applications of network BLAST server," Methods Enzymol 266:131-141 (1996).
Mahoney et al., "Combination cancer immunotherapy and new immunomodulatory targets," Nat Rev Drug Discov 14:561-584 (2015).
Mariuzza et al., "The Structural Basis of Antigen-Antibody Recognition," Ann Rev Biophys Biophys Chem 16:139-159 (1987).
Marks et al., "By-passing immunization: building high affinity human antibodies by chain shuffling," Bio/Technology 10(7):779-783 (1992).
Merchant et al., "An efficient route to human bispecific IgG," Nat Biotechnol 16(7):677-681 (1998).
Moore et al., "Application of dual affinity retargeting molecules to achieve optimal redirected T-cell killing of B-cell lymphoma," Blood 117(17):4542-4551 (2011).
Muller et al., "Bispecific antibodies for cancer immunotherapy: Current perspectives," BioDrugs 24:89-98 (2010).
Nunez-Prado et al., "The coming of age of engineered multivalent antibodies," Drug Discov Today 20(5):588-594 (2015).
Nygren et al., "Scaffolds for engineering novel binding sites in proteins," Curr Opin Struct Biol 7(4):463-469 (1997).
Patten et al., "Applications of DNA shuffling to pharmaceuticals and vaccines," Curr Opin Biotechnol 8(6):724-733 (1997).
Persic et al., "An integrated vector system for the eukaryotic expression of antibodies or their fragments after selection from phage display libraries," Gene 187(1):9-18 (1997).
Peters, "Serum albumin," Adv Protein Chem 37:161-245 (1985).
Pule et al., "Artificial T-cell receptors," Cytotherapy 5(3):211-226 (2003).
Rajagopal et al., "A form of anti-Tac(Fv) which is both single-chain and disulfide stabilized: comparison with its single-chain and disulfide-stabilized homologs," Protein Eng 10(12):1453-1459 (1997).
Reiter et al., "Stabilization of the Fv fragments in recombinant immunotoxins by disulfide bonds engineered into conserved framework regions," Biochemistry 33(18):5451-5159 (1994).
Reiter et al., "Improved binding and antitumor activity of a recombinant anti-erbB2 immunotoxin by disulfide stabilization of the Fv fragment," J Biol Chem 269(28):18327-18331 (1994).
Richards et al., "Optimization of antibody binding to FcgammaRIIa enhances macrophage phagocytosis of tumor cells," Mol Cancer Ther 7(8):2517-2527 (2008).
Ridgway et al., "'Knobs-into-holes' engineering of antibody CH3 domains for heavy chain heterodimerization," Protein Eng 9:617-621 (1996).
Rudikoff et al., "Single amino acid substitution altering antigen-binding specificity," *Proc Natl Acad Sci USA* 79:1979-1983 (1982).
Ryan et al., "Antibody targeting of B-cell maturation antigen on malignant plasma cells," Mol Cancer Ther 6(11):3009-3018 (2007).
Shields et al., "High resolution mapping of the binding site on human IgG1 for Fc gamma Rl, Fc gamma Rll, Fc gamma Rlll, and FcRn and design of IgG1 variants with improved binding to the Fc gamma R," J Biol Chem 276(9):6591-6604 (2001).
Stavenhagen et al., "Enhancing the potency of therapeutic monoclonal antibodies via Fc optimization," Adv Enzyme Regul 48:152-164 (2008).
Stavenhagen et al., "Fc optimization of therapeutic antibodies enhances their ability to kill tumor cells in vitro and controls tumor expansion in vivo via low-affinity activating Fcgamma receptors," Cancer Res 16(18):8882-8890 (2007).
Steurer et al., "Ex vivo coating of islet cell allografts with murine CTLA4/Fc promotes graft tolerance," J Immunol 155(3):1165-1174 (1995).
Thireos et al., "5' untranslated sequences are required for the translational control of a yeast regulatory gene," Proc Natl Acad Sci USA 81:5096-5100 (1984).
Thompson et al., "Affinity maturation of a high-affinity human monoclonal antibody against the third hypervariable loop of human immunodeficiency virus: use of phage display to improve affinity and broaden strain reactivity," J Mol Biol 256(1):77-88 (1996).
Thorpe et al., "The preparation and cytotoxic properties of antibody-toxin conjugates," Immunol Rev 62:119-158 (1982).
Vaccaro et al., "Engineering the Fc region of immunoglobulin G to modulate in vivo antibody levels," Nat Biotechnol 23(10):1283-1288 (2005).
Vajdos et al., "Comprehensive Functional Maps of the Antigen-binding Site of an Anti-ErbB2 Antibody Obtained with Shotgun Scanning Mutagenesis," J Mol Biol 320:415-428 (2002).
Van Der Stegen et al., "The pharmacology of second-generation chimeric antigen receptors," Nat Rev Drug Discov 14:499-509 (2015).
Vaughan et al., "Human antibodies by design," Nat Biotechnol 16(6):535-539 (1998).
Verma et al., "Antibody engineering: comparison of bacterial, yeast, insect and mammalian expression systems," J Immunol Methods 216:165-181 (1998).
Waldemann et al, "Metabolism of immunoglobulins," Prog Allergy 13:1-110 (1969).
Walker et al., "CD22: an inhibitory enigma," Immunology 123(3):314-325 (2008).

(56) References Cited

OTHER PUBLICATIONS

Wienands, "The B-cell antigen receptor: formation of signaling complexes and the function of adaptor proteins," Curr Top Microbiol Immunol 245:53-76 (2000).

Winkler et al., "Changing the Antigen Binding Specificity by Single Point Mutations of an Anti-p24 (HIV-1) Antibody," J Immunol 165:4505-4514 (2000).

Wu et al., "Humanization of a Murine Monoclonal Antibody by Simultaneous Optimization of Framework and CDR Residues," J Mol Biol 294:151-162 (1999).

Yang et al., "CDR walking mutagenesis for the affinity maturation of a potent human anti-HIV-1 antibody into the picomolar range," J Mol Biol 254(3):392-403 (1995).

Young et al., "Thermal stabilization of a single-chain Fv antibody fragment by introduction of a disulphide bond," FEBS Lett 377(2):135-139 (1995).

Yu et al., "Interaction between Bevacizumab and Murine VEGF-A: A Reassessment," *Invest Ophthalmol Vis Sci* 49(2):522-527 (2008).

Yu et al., "Rationalization and Design of the Complementarity Determining Region Sequences in an Antibody-Antigen Recognition Surface," PLOS One 7(3):e33340 (2012).

Zhang et al., "PowerBLAST: a new network BLAST application for interactive or automated sequence analysis and annotation," Genome Res 7(6):649-656 (1997).

Zhu et al., "Remodeling domain interfaces to enhance heterodimer formation," Protein Sci 6(4):781-788 (1997).

Hernández-Molina et al., "The meaning of anti-Ro and anti-La antibodies in primary Sjögren's syndrome," Autoimmunity Reviews 10:123-125 (2011).

\* cited by examiner

|  | A₁X | A₂X | A₃X | A₄X |
|---|---|---|---|---|
| B₁Y | A₁X B₁Y | A₂X B₁Y | A₃X B₁Y | A₄X B₁Y |
| B₂Y | A₁X B₂Y | A₂X B₂Y | A₃X B₂Y | A₄X B₂Y |
| B₃Y | A₁X B₃Y | A₂X B₃Y | A₃X B₃Y | A₄X B₃Y |
| B₄Y | A₁X B₄Y | A₂X B₄Y | A₃X B₄Y | A₄X B₄Y |

Surface plasmon resonance analysis of Antigen5Fab- scFv (52RS4) binding to GNC4 peptide

| Sample | Biotin-GCN4 Peptide | | | |
|---|---|---|---|---|
| | ka (1/Ms) | kd (1/s) | Affinity (pM) | Immuno-reactivity % |
| Antigen5Fab52RS4scFv | 5.10E+05 | 2.70E-04 | 516 | 105 |

% Immunoreactivity = Rmax/Estimated Rmax x 100

Figure 22

Fab-X specificity antigen 1-15

Fab-Y specificity antigen 1-23

% Inhibition

| SP_Y... | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | 0.81 | 22.29 | 11.45 | 10.78 | 5.39 | 1.60 | 7.43 | 5.90 | 2.24 | 3.29 | -2.71 | 10.80 | 0.99 | 6.90 | -4.08 |
| 2 | 19.70 | 18.61 | 44.00 | 50.83 | 23.17 | 19.01 | 24.57 | 21.47 | 25.89 | 39.80 | 12.35 | 0.52 | 18.91 | 28.55 | 25.89 |
| 3 | 17.93 | 61.18 | 3.00 | 15.38 | 5.38 | -0.12 | 4.05 | 3.77 | 6.84 | 12.78 | 11.01 | 16.71 | 2.97 | 9.17 | 4.69 |
| 4 | 13.34 | 55.83 | -3.82 | 7.24 | 1.41 | -1.39 | 6.75 | 0.89 | 3.12 | 3.12 | 4.16 | 40.49 | 1.71 | 5.13 | 1.10 |
| 5 | 0.34 | 25.16 | 0.51 | -0.63 | 7.36 | -1.41 | 11.49 | 4.08 | 5.59 | 2.99 | 5.76 | 11.67 | 2.84 | 5.90 | -2.06 |
| 6 | --- | 20.71 | -0.85 | 6.04 | 0.40 | 3.49 | -2.60 | -0.87 | 3.41 | 0.22 | 1.34 | 12.34 | 3.36 | --- | --- |
| 7 | 10.95 | 27.95 | 1.38 | 15.66 | 11.27 | 2.40 | 2.48 | 4.45 | 6.13 | 16.07 | 3.18 | 12.77 | 3.92 | 5.85 | 0.37 |
| 8 | 7.73 | 24.86 | 4.02 | 5.23 | 3.56 | 0.49 | 2.68 | -1.16 | 2.39 | 1.45 | 4.10 | 8.50 | -0.64 | 3.01 | 0.97 |
| 9 | 7.37 | 28.27 | -0.02 | 3.22 | 6.39 | 1.35 | 4.75 | 4.06 | 4.92 | 4.09 | 3.10 | 10.50 | 0.62 | 5.62 | 1.50 |
| 10 | 17.08 | 47.69 | 7.72 | 5.65 | -5.55 | 1.40 | 21.89 | 6.66 | 5.90 | 5.11 | 7.61 | 35.77 | 1.50 | 4.32 | -0.06 |
| 11 | --- | 11.76 | -10.93 | 1.38 | -0.56 | -24.94 | -1.36 | 0.83 | 3.58 | 3.88 | 5.92 | 11.18 | -4.57 | --- | --- |
| 12 | 6.05 | -3.88 | 9.02 | 29.48 | 4.92 | 1.15 | 1.89 | 5.75 | 7.23 | 20.95 | 5.44 | 17.92 | 3.37 | 16.34 | 8.67 |
| 13 | --- | 23.78 | -0.99 | 7.30 | 0.43 | -1.40 | 1.83 | 6.41 | 8.91 | 3.25 | 2.76 | 11.64 | 5.41 | --- | --- |
| 14 | 4.40 | 28.11 | 1.77 | 5.61 | 4.01 | 1.73 | 5.95 | 2.45 | 4.05 | 6.85 | -0.60 | 20.60 | 5.45 | 4.11 | 0.05 |
| 15 | 4.96 | 25.60 | 0.87 | 3.43 | 5.41 | 1.77 | 1.89 | 1.80 | 3.72 | 1.96 | 2.29 | 14.57 | 5.26 | 2.36 | 0.11 |
| 16 | --- | 22.39 | -5.77 | 4.50 | 2.41 | -6.86 | 4.89 | 2.52 | 5.19 | 3.07 | 3.38 | 9.47 | 1.17 | --- | --- |
| 17 | --- | 19.53 | -6.98 | 6.73 | 2.99 | -10.27 | 2.35 | 2.13 | 6.02 | 2.08 | 3.10 | 10.86 | 2.03 | --- | --- |
| 18 | --- | 19.90 | 2.43 | 12.38 | 2.08 | -1.05 | 1.09 | 4.25 | 6.70 | 4.90 | 4.40 | 12.49 | 4.34 | --- | --- |
| 19 | --- | 35.50 | -12.22 | -2.38 | -1.61 | -9.05 | 5.97 | 1.78 | 5.27 | 4.63 | 5.92 | 15.60 | 3.16 | --- | --- |
| 20 | --- | 21.53 | -9.67 | 2.95 | -0.16 | -6.71 | -3.46 | -4.81 | 4.13 | 2.31 | 6.52 | 10.96 | 4.25 | --- | --- |
| 21 | --- | 19.03 | -6.66 | 2.36 | 1.10 | -6.49 | -0.95 | 5.09 | 4.96 | 3.55 | 3.97 | 10.89 | 3.63 | --- | --- |
| 22 | 14.73 | 26.47 | -5.00 | 0.58 | 3.97 | -0.08 | 3.70 | -1.25 | 1.72 | 0.99 | 11.40 | 7.99 | 2.80 | 8.39 | 4.58 |
| 23 | --- | 19.72 | -16.22 | 0.75 | -1.16 | -11.03 | -3.57 | 3.30 | 3.57 | 1.23 | 4.90 | 8.22 | 4.20 | --- | --- |

Figure 23

Fab-X specificity antigen 1-15

Fab-Y specificity antigen 1-23

| SP_Y... | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | -11.06 | 53.06 | -1.56 | 6.02 | -8.08 | -12.41 | 3.84 | -12.93 | -8.22 | -8.88 | -11.49 | -3.34 | -17.29 | -4.43 | -6.28 |
| 2 | 40.41 | 37.15 | 48.29 | 48.35 | 39.50 | 30.66 | 40.36 | 25.61 | 42.23 | 42.64 | 32.59 | 37.11 | 26.58 | 35.70 | 38.11 |
| 3 | 13.19 | 70.81 | 2.37 | 15.53 | 8.68 | 7.93 | 12.32 | 3.78 | 10.56 | 14.18 | 8.76 | -1.58 | 6.61 | 10.75 | 10.83 |
| 4 | 8.35 | 55.50 | -6.07 | 17.80 | 7.97 | 7.14 | 8.49 | 6.54 | 6.98 | 9.67 | 12.96 | 41.04 | 5.99 | 9.28 | 7.89 |
| 5 | -3.80 | 40.21 | -0.85 | 13.54 | 2.05 | -2.13 | 3.01 | -6.86 | 0.91 | 2.02 | 0.76 | 4.48 | -3.42 | 4.06 | 0.15 |
| 6 | --- | 40.39 | 6.67 | 19.26 | -4.86 | 12.95 | 3.52 | 2.59 | 6.73 | 5.65 | 5.28 | 4.77 | -1.03 | --- | --- |
| 7 | 0.53 | 45.36 | 4.87 | 18.76 | 4.08 | 0.72 | -1.43 | 5.07 | 4.69 | 11.49 | 6.48 | 5.72 | 4.78 | 0.73 | -3.71 |
| 8 | 6.61 | 37.54 | 5.72 | 16.25 | -1.45 | 2.38 | 0.64 | 0.17 | 1.10 | 2.08 | 6.50 | 7.58 | 2.18 | -4.37 | -4.53 |
| 9 | 0.51 | 42.34 | 0.95 | 9.41 | -0.30 | 1.07 | 2.86 | -2.56 | 0.51 | -0.55 | 2.07 | 2.49 | -2.84 | 4.54 | 0.16 |
| 10 | 11.13 | 52.32 | 3.75 | 12.67 | -4.41 | 3.82 | 15.78 | -3.15 | 5.70 | 4.26 | 1.77 | 22.73 | -4.68 | 7.65 | 8.05 |
| 11 | --- | 33.40 | -3.95 | 18.04 | 7.48 | 6.00 | 3.13 | 4.24 | 5.66 | 13.11 | 9.85 | 11.24 | 2.04 | --- | --- |
| 12 | 0.69 | 29.50 | -7.93 | 38.94 | 2.68 | 4.95 | -0.13 | -2.53 | 2.52 | 15.03 | -0.82 | 3.63 | -5.61 | 25.99 | 12.57 |
| 13 | --- | 35.33 | -4.80 | 10.35 | -4.98 | -7.45 | -7.91 | -6.47 | 3.78 | -0.83 | -4.68 | -3.84 | -9.54 | --- | --- |
| 14 | 1.62 | 44.02 | 0.91 | 16.05 | 1.80 | -2.56 | 1.09 | -4.49 | 3.94 | 5.30 | -0.19 | 8.15 | -5.85 | 5.21 | 0.66 |
| 15 | 2.25 | 36.02 | -2.44 | 10.00 | -0.22 | 0.37 | -2.20 | -2.11 | 2.41 | 1.84 | 3.23 | 2.78 | 2.51 | -2.19 | -4.62 |
| 16 | --- | 33.56 | -3.12 | 15.33 | 0.19 | -5.46 | -0.71 | -5.67 | 1.83 | 1.35 | -0.24 | -1.99 | -8.53 | --- | --- |
| 17 | --- | 35.02 | -4.92 | 16.87 | 1.78 | -2.20 | 0.34 | -2.12 | 3.07 | 1.17 | 0.98 | 0.80 | -2.14 | --- | --- |
| 18 | --- | 31.31 | -1.77 | 19.71 | -6.19 | -4.39 | -3.72 | -3.91 | 2.70 | 3.44 | -0.42 | -1.65 | -5.72 | --- | --- |
| 19 | --- | 50.00 | -2.93 | 9.92 | 2.01 | 9.54 | 10.19 | 2.60 | 11.44 | 9.84 | 7.96 | 9.17 | 3.37 | --- | --- |
| 20 | --- | 38.56 | -1.83 | 18.96 | 1.40 | 5.57 | 0.37 | 1.23 | 4.23 | 6.85 | 10.48 | 6.54 | 2.60 | --- | --- |
| 21 | --- | 36.74 | 1.67 | 11.59 | -5.60 | 6.23 | 0.59 | 6.00 | 6.99 | 5.11 | 3.12 | 3.73 | 3.44 | --- | --- |
| 22 | -2.71 | 40.50 | -2.45 | 12.91 | -1.39 | 6.77 | 1.56 | 4.97 | 1.68 | 2.93 | 18.10 | 8.41 | 8.06 | -2.35 | -4.93 |
| 23 | --- | 33.54 | -1.68 | 5.45 | -2.46 | 7.13 | 0.05 | -3.14 | 2.99 | 3.34 | 6.02 | 4.97 | -4.12 | --- | --- |

% Inhibition AKT

% Inhibition (+/- SD) of Phosphorylated PLCγ2 in
Anti-IgM Stimulated B-cells
by Antigen 3 and Antigen 2 Specific Fab-Kd-Fab and BYbe.

% Inhibition (+/- SD) of Phosphorylated Akt in Anti-IgM Stimulated B-cells, by Antigen 3 and Antigen 2 Specific Fab-Kd-Fab and BYbe.

% Inhibition of Anti-IgM Induced CD71 on B-cells,
by Antigen 3 and Antigen 2 Specific Fab-Kd-Fab and BYbe % Inhibition of Anti-IgM Induced CD86 on B-cells by Antigen 3 and Antigen 2 Specific BYbe and Fab-Kd-Fab

BISPECIFIC FORMAT SUITABLE FOR USE IN HIGH-THROUGH-PUT SCREENING

CROSS-REFERENCE TO RELATED APPLICATION

This application is the U.S. national stage application of International Patent Application No. PCT/EP2015/061819, filed May 28, 2015.

FIELD OF INVENTION

The present disclosure relates to a method, in particular an in vitro/ex vivo method, of detecting synergistic biological function in a heterodimerically-tethered bispecific protein complex, libraries/multiplexes of the bispecific protein complexes, and kits and compositions thereof. The disclosure further relates to said novel bispecific protein complexes and use of the same in therapy, research and experimental purposes (in particular in assays looking for synergistic biological function). The present disclosure also extends to methods of preparing said bispecific complexes.

BACKGROUND OF INVENTION

Biological mechanisms in vivo are extremely complicated cascades of signals, which are difficult to deconvolute and understand. An example of such signalling is that required to activate T-cells, see FIG. 1, from www.cellsignal.com. Activation of T cells requires at least two signals.

The recognition of the antigen by the T cell receptor is considered the first signal and the second signal arises from co-stimulation which results from the ligation of additional surface molecules on the T cell with additional molecules on an antigen presenting cell.

Thus T cell activation can be used to illustrate that the modulation of biological functions can require multiple signals. Other biological processes are equally complicated or more complicated. Whilst in vitro screening based on cells has and can assist with gaining insights into in vivo mechanisms the problem still arises of how to identify appropriate ligand pairs which modulate the biological function.

Bispecific antibodies are widely expected to play a major role in the next generation of biotherapeutics (D. Holmes, Nature Rev Drug Disc November 2011:10; 798). They have the potential to deliver superior, long term, broad efficacy in a greater proportion of patients.

This can be achieved by either co-engaging different antigens simultaneously within a common disease pathway, thereby reducing redundancy; or by targeting antigens from independent pathways to provide an additive or synergistic effect.

Bispecific antibodies facilitate access to novel biology such as:
1) cross-linking receptors on a cell,
2) inducing cell mediated effects,
3) localizing a cytokine to a cell to regulate signaling or locally block cytokine function,
4) engaging multiple epitopes simultaneously to generate "new activity", increase function or specificity, which may not be exhibited by a single monoclonal antibody or indeed mixtures of un-linked antibodies (poly-monoclonals').

Current strategies to engage dual targets are largely based on rational design of known mechanisms and include: cross-linking inhibitory receptors, co-engagement/clustering of receptors, blocking multiple stimulatory pathways, selective engagement of inhibitory receptors and blocking distinct pathways such as co-stimulation & cytokine signaling. However, the current state of the art in relation to known mechanisms and targets is a limiting factor to progress in this area.

Whilst bispecific antibodies have enormous potential as biological therapeutics they also present an increased set of challenges within discovery and development compared to monoclonal antibodies. Two key areas of difficulty are, 1) the development of a successful bispecific antibody format, and 2) selecting the pairs of targets to which the bispecific antibody will crosslink or co-engage.

Many promising bispecific antibody formats have now been developed that could potentially work as successful therapeutics including DVD-Ig (Abbvie), DuoBodies (Genmab), Knobs-in-Holes (Genentech), Common light chain (Merus). However, in each of these cases these formats are not ideally suited to high throughput target-dual-antigen discovery screening to enable the discovery of novel antigen pairs for crosslinking with bispecific antibodies.

Typically for a single bispecific antibody construct at least two variable regions need to be sub-cloned from the original source of discovery vectors (e.g. phage display, hybridoma or single B-cell cloning) into appropriate bispecific expression vectors, each arm of the bispecific has to be expressed and the resulting bispecific antibody purified. This cloning and subsequent expression effort quickly becomes a significant practical bottleneck if large numbers of pairs of variable regions are to be combined in an attempt to screen for the most efficacious combination of discovered variable regions or to discover novel antigen pairs.

For example, if 50 unique antibodies are discovered against a panel of 50 cell surface targets, then a total of 2500 bispecific antibodies could potentially be generated (envisaged as an X-by-Y grid). With the bispecific antibody formats described above this would require at least 100 individual cloning reactions (50-X and 50-Y) followed by 2500 antibody expression experiments. Increasing the number of starting monoclonal antibodies to 100 would increase the minimal number of cloning reactions to 200 (100-X and 100-Y) and the expression number to 10,000.

Generally the root cause of this 'expression bottleneck' is the fact that the formats described above require both protein chain 'halves' of the final bispecific construct to be expressed simultaneously within a single expression experiment in the same cell. Therefore, for many formats, to produce 2500 bispecific antibodies, 2500 expression experiments are required. The 'expression bottleneck' is further exacerbated if the bispecific antibody format is monocistronic (i.e. cloned and expressed as a single chain protein), for example single chain diabodies, as the number of cloning experiments would be 2500 and 10,000 respectively for the numbers given above.

Furthermore after expression, extensive purification may be required to isolate the desired construct.

Some bispecific approaches employ a common light chain in the bispecific constructs in order to reduce the amount of cloning, although this doesn't reduce the number of expression experiments. Furthermore, using a common chain, such as a common light chain, makes the challenge of antibody discovery harder as it is more difficult to find the starting antibody variable domains as the antibody needs to bind its antigen with a high enough affinity through one chain, such as the heavy chain, alone.

Accordingly the use of current bispecific formats in large scale and high throughput screening to identify novel antigen pairs is impractical and has led to the continued use of solely hypothesis driven approaches to bispecific antigen targeting.

We propose that rather than designing and testing a limited selection of bispecific antibodies that engage given epitopes on two known targets, the true potential of exploiting access to novel biology with bispecific antibodies can only be achieved through a broad functional screening effort with a large, diverse combinatorial panel of bispecific antibodies or protein ligands. To facilitate this screening a format and a method is required that enables the generation of large numbers of diverse bispecific proteins which can be readily constructed and screened for functional effects in a variety of functional screens. This approach allows for the serendipitous identification of synergistic pairs.

Thus it would be useful to generate and screen a large number of bispecific protein complexes present as combinations of various antigen specificities. In particular, it would be useful to be able to generate and screen a large number of different bispecific antibody complexes in a quick and efficient manner. There are a range of existing methods for manufacturing bispecific antibodies as already described above. However, each of these methods has its disadvantages, as do alternative methods as further described in more detail below.

The problem of how to efficiently identify targets for bispecific and multispecific constructs has not been adequately addressed in the art. For example WO2014/001326 employs chemical conjugation of a protein to a DNA fragment, wherein the DNA fragment hybridises to a complementary DNA sequence that links two such proteins together for generating tailor-made patient-specific multispecific molecules comprising at least two targeting entities. There are number of difficulties associated with this approach if it were to be applied to identifying new bispecific combinations, for example conjugation of the protein to the DNA can result in damage to the activity and/or structure of the protein. In particular protein-DNA hybrids are not naturally occurring thus there is a potential for interference. In addition the chemical conjugation required to join the protein and DNA adds complexity, time and expense to the process.

Coupling and conjugation techniques exist for generating antibody drug conjugates and in vivo targeting technologies. Traditional chemical cross-linking is labour intensive as the relevant species may need to be purified from homodimers and other undesirable by-products. In addition, the chemical modification steps can alter the integrity of the proteins, thus leading to poor stability or altered biological function. As a result, the production of bispecific antibodies by chemical cross-linking is often inefficient and can also lead to a loss of antibody activity.

Another method of manufacturing bispecific antibodies is by cell-fusion (e.g. hybrid hybridomas), wherein the engineered cells express two heavy and two light antibody chains that assemble randomly. Since there are 4 possible variants to choose from, this results in the generation of 10 possible bispecific antibody combinations, of which only some (in many cases, only one) combinations would be desired. Hence, generating bispecific antibodies by cell-fusion results in low production yields and also requires an additional purification step in order to isolate the desired bispecific antibodies from the other bispecific antibodies produced. These disadvantages increase manufacturing time and costs.

Recombinant DNA techniques have also been employed for generating bispecific antibodies. For example, recombinant DNA techniques have also been used to generate 'knob into hole' bispecific antibodies. The 'knob into hole' technique involves engineering sterically complementary mutations in multimerization domains at the CH3 domain interface (see e.g., Ridgway et al., Protein Eng. 9:617-621 (1996); Merchant et al., Nat. Biotechnol. 16(7): 677-81 (1998); see also U.S. Pat. Nos. 5,731,168 and 7,183,076). One constraint of this strategy is that the light chains of the two parent antibodies have to be identical to prevent mispairing and formation of undesired and/or inactive molecules when expressed in the same cell. Each bispecific (heavy and light chains thereof) must be expressed in a single cell and the protein product generally contains about 20% of homodimer, which is subsequently removed by purification.

Other approaches are based on the natural exchange of chains in full-length IgG4 molecules (Genmab Dubody). However, this approach also has difficulties because it does not allow a construct to be prepared without an Fc region. As the Fc region can contribute to biological activity it may be difficult to establish if an activity observed is based on the combination of variable regions, the Fc or both in bispecific molecules comprising an Fc. Furthermore, the exchange is a dynamic process and this may lead to difficulties in relation to what the entity tested actually is.

Thus there is a need for new methods of generating bispecific protein complexes to enable the more efficient and higher throughput screening of bispecific antibodies. In particular, there is a need for a format and a method wherein a selection of any two antibodies or antibody fragments from a pool of available antibodies or antibody fragments can be readily combined to efficiently produce a multiplex of different bispecific antibodies, whilst, for example avoiding or minimising the formation of homodimers. Assembling different bispecific antibodies efficiently is particularly important when screening for synergistic biological function for new combinations of antigen specificities, in particular where heterodimers are essential for discovering that function.

SUMMARY OF INVENTION

In one aspect there is provided a new bispecific format particularly suitable for use in screening because all of the components can be expressed from a cell as individual units, essentially without aggregation and the units can be assembled simply by mixing without employing conjugation or coupling chemistry and with minimal homodimerisation.

Thus there is provided a bispecific protein complex having the formula A-X:Y-B wherein:
  A-X is a first fusion protein;
  Y—B is a second fusion protein;
  X:Y is a heterodimeric-tether;
  : is a binding interaction between X and Y;
  A is a first protein component of the bispecific protein complex selected from a Fab or Fab' fragment;
  B is a second protein component of the bispecific protein complex selected from a Fab or Fab' fragment;
  X is a first binding partner of a binding pair independently selected from an antigen or an antibody or a binding fragment thereof; and
  Y is a second binding partner of the binding pair independently selected from an antigen or an antibody or a binding fragment thereof;
with the proviso that when X is an antigen Y is an antibody or binding fragment thereof specific to the antigen represented by X and when Y is an antigen X is an antibody or binding fragment thereof specific to the antigen represented by Y.

In one embodiment the variable X or Y is an antibody binding fragment such as a scFv, Fv, VH, VL or VHH and the other variable is a peptide.

In one embodiment the variable X or Y is a scFv or VHH and the other variable is a peptide.

Thus the bispecific format comprises two Fab arms with different specificities linked, for example via their C-terminal, by an antibody binding fragment (such as a scFv or a VHH) and peptide binding interaction. This type of arrangement is ideal for use in screening because there is no difficulty expressing the unit A-X or the unit B-Y. The Fab/Fab' fragment is very stable and is not susceptible to inappropriate dimerization. Thus the amount of purification required after expression of each unit (A-X or B-Y) is minimal or in fact, unnecessary. The bispecific complex can be formed in a 1:1 molar ratio by simply admixing the relevant units i.e. without recourse to conjugation and coupling chemistry. The constant regions in the Fab/Fab' fragment drive dimerization of the Fab/Fab' components and the binding partners X and Y drive the equilibrium further in favour of forming the requisite heterodimer bispecific complex. Again little or no purification is required after formation of the complex after heterodimerisation. Thus large number of A-X and B—Y can be readily prepared and combined.

The Fab/Fab' entities in the complex mean the binding domains are held in biologically relevant orientations which mimic classic antibody geometry and this may contribute to the success of translating the pairs of variable regions identified by the screening method described herein below into other bispecific therapeutic formats which retain activity. The ability to prepare and screen a bispecific complex lacking the Fc fragment CH2-CH3 also ensures that the biological activity observed is in fact due solely to the variable region pairs in the complex. The simplicity of the bispecific complex of the invention and the methods of preparing it are a huge advantage in the context of facilitating high-through-put screening of variable domain pairs to find new target antigen combinations and also to optimise variable region sequences for a given combination.

In one embodiment A is a Fab fragment. In one embodiment B is a Fab fragment. In one embodiment A and B are both a Fab fragment (also referred to herein as a Fab-Kd-Fab).

In one embodiment X is fused to the C-terminal of a heavy chain or light chain in the Fab or Fab' fragment, in particular the C-terminal of the heavy chain.

In one embodiment Y is fused to the C-terminal of a heavy chain or light chain in the Fab or Fab' fragment, in particular the C-terminal of the heavy chain.

In one embodiment X is independently selected from a scFv, a VHH and a peptide, with the proviso that when X is a peptide Y is an antibody or binding fragment thereof, such as a scFv or VHH and when X is a scFv or VHH then Y is an antigen, such as a peptide.

In one embodiment Y is independently selected from a scFv, a VHH and a peptide, with the proviso that Y is a peptide X is an antibody or binding fragment, such as a scFv or VHH and when Y is a scFv or a VHH then X is an antigen, such as a peptide.

In one embodiment the peptide (which is one of the binding partners) is in the range 5 to 25 amino acids in length.

In one embodiment the binding affinity between X and Y is 5 nM or stronger, for example the binding affinity of the heterodimeric tether is 900 pM or stronger, such as 800, 700, 600, 500, 400 or 300 pM.

In one embodiment X or Y is a scFv or VHH specific to the peptide GCN4, for example the scFv is 52SR4 (SEQ ID NO:3 or amino acids 1-243 of SEQ ID NO:3).

In one embodiment X or Y is a peptide GCN4 (SEQ ID NO:1 or amino acids 1-38 of SEQ ID NO:1).

In one embodiment A and/or B is specific for an antigen selected from the group comprising: cell surface receptors such as T cell or B cell signalling receptors, co-stimulatory molecules, checkpoint inhibitors, natural killer cell receptors, Immunolglobulin receptors, immunoglobulin-like receptors, matrix metalloproteases and membrane type matrix metalloproteases tissue inhibitors of metalloproteases, TNFR family receptors, B7 family receptors, adhesion molecules, integrins, cytokine/chemokine receptors, GPCRs, growth factor receptors, kinase receptors, tissue-specific antigens, cancer antigens (tumour associated antigens & peptides), pathogen recognition receptors, complement receptors, hormone receptors, scavenger receptors, or soluble molecules such as cytokines, chemokines, leukotrienes, growth factors, hormones or enzymes or ion channels, including post translationally modified version thereof, fragments thereof comprising at least one epitope.

In one embodiment there is provided a composition, for example a pharmaceutical composition comprising one or more bispecific complexes according to the present disclosure.

Furthermore, the present inventors have devised a method of detecting synergistic function in a heterodimerically-tethered bispecific protein complex of formula A-X:Y-B wherein X:Y is a heterodimeric-tether, for example where X and Y are unsuitable for forming homodimers,
A and B are components of the bispecific in the form of fusion proteins with X and Y respectively, said method comprising the steps of:
  (i) testing for activity in a functional assay for part or all of a multiplex comprising at least one heterodimerically-tethered bispecific protein; and
  (ii) analysing the readouts from the functional assay to identify synergistic biological function in the bispecific protein complex.

The method employs a novel bispecific protein complex format having the following formula A-X:Y-B wherein:
  A-X is a first fusion protein;
  Y—B is a second fusion protein;
  X:Y is a heterodimeric-tether;
  A is a first protein component of the bispecific;
  B is a second protein component of the bispecific;
  X is a first binding partner of a binding pair;
  Y is a second binding partner of the binding pair; and
  : is an interaction (for example a binding interaction) between X and Y, in particular the interaction is sufficient to form the complex and retain the fusion proteins in a complexed form.

In particular, the heterodimerically-tethered bispecific protein complex is prepared by mixing A-X and B-Y in vitro. Thus in one embodiment the method comprises an in vitro mixing step bringing A-X and B-Y into contact.

Thus generally the fusion proteins A-X and B—Y are not co-expressed in the same cell. This is advantageous because it allows, for example 100 fusion proteins to expressed and optionally purified and the subsequent mixing of the 100 fusion proteins in the various permutations can provide 10,000 heterodimerically-tethered bispecific protein complexes, of which 5,000 are unique pairs.

In contrast certain prior art methods require co-expression of bispecifics and thus for 10,000 complexes, 10,000 transfections, expressions and purifications are required.

However, if desired the A-X and B—Y may be expressed in the same cell.

The binding partners X and Y have affinity for each other and act as biological equivalent of VELCRO® or a bar and magnet and hold the complex together. Advantageously, this means that the fusion proteins A-X and Y—B can be readily assembled into a bispecific protein complex simply by mixing the fusion proteins together. Thus the bispecific protein complex of the present disclosure has a modular structure which allows for two different proteins to be easily assembled in order to produce large panels of permutations of bispecific protein complexes with different combinations of antigen specificities in, for example a grid-like fashion. This allows for the efficient and systematic screening of a large number of bispecific protein complexes in order to detect additive, synergistic or novel biological function.

Given X and Y are specific for each other this significantly reduces the ability to form homodimers. X and Y are collectively referred to herein as a binding pair or binding partners. In one embodiment X does not have high affinity for other Xs. In one embodiment Y does not have high affinity for other Ys. Advantageously, when X and Y do not form homodimers, this prevents the formation of undesired monospecific protein complexes, increases yield of the desired bispecific protein complexes, and removes the need for onerous purification steps to remove the monospecific protein complexes.

This allows rapid assembly of bispecific protein complexes with a yield and/or purity which cannot be obtained efficiently by most prior art methods, in particular prior art methods generally require extensive purification steps. The yield of bispecific complex is typically 75% or higher in the present invention.

Further advantageously, the bispecific protein complexes allow for the screening of complexes wherein the constituent proteins (including antigens bound by the constituent proteins) do not have a known relationship or are in different potentially unrelated pathways, such as, two proteins which function in two distinct pathways and, for example which the skilled person would not normally expect to come into contact with each other can be tested in a bispecific protein complex to identify additive, synergistic and/or novel function.

Furthermore multiple binding regions (such as variable regions) to a given antigen or epitope can be investigated in parallel to identify nuances in biological function. This allows combinations of variable region sequences directed to a given pair of antigens to be investigated and optimised.

The present method allows the science to show the results and does not rely on pre-conceived ideas and technical prejudice about the biological function. This approach is potentially very powerful.

Advantageously the X and Y components allow a multiplex comprising bispecific protein complexes made up of different permutations of fusion proteins to be assembled rapidly and easily.

In one embodiment the proteins A and B are antibodies or antibody fragments. When the antibody or antibody fragments are held together as a complex via X and Y, this forms a bispecific antibody complex.

Filled area=[anti-antigen 5 Fab-peptide 'GCN4']: [anti-antigen 6 Fab-peptide 'GCN4']: [biotinylated-antigen 6]: [FITC-STREP]. No complex formation control.

Thin line=[anti-antigen 5 Fab-scFv '52SR4']: [anti-antigen 6 Fab-peptide 'GCN4']: [biotinylated-antigen 6]: [FITC-STREP]

Thick line=[anti-antigen 5 Fab-peptide 'GCN4']: [anti-antigen 6 Fab-scFv '52SR4']: [biotinylated-antigen 6]: [FITC-STREP]

Figure 6:
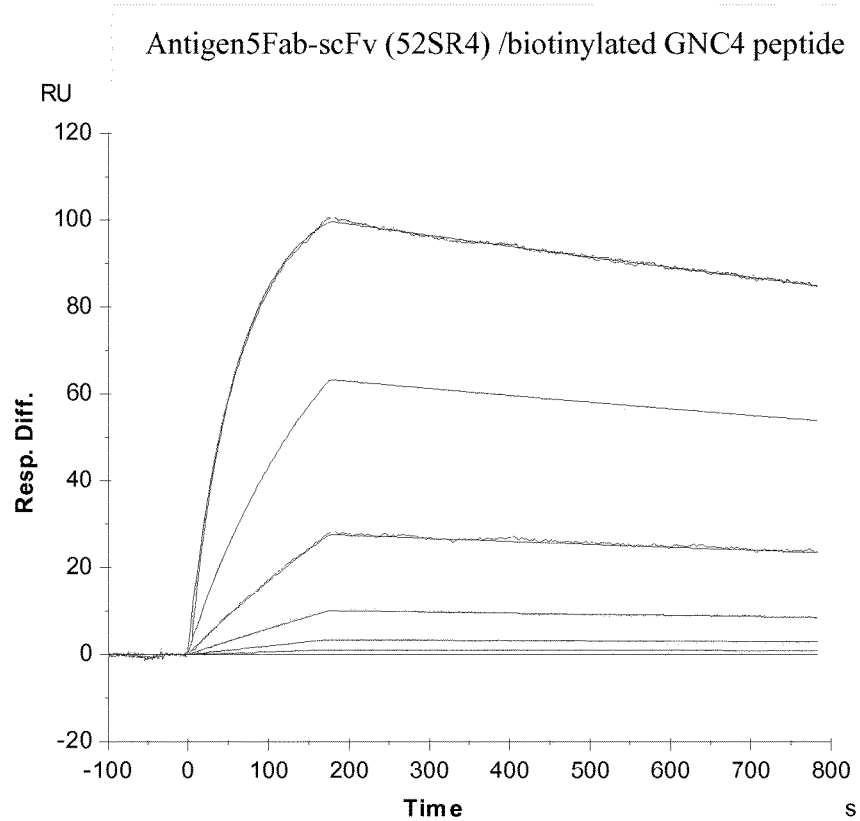

FIG. 6 is a graph and a table showing a BIAcore trace, which demonstrates the high affinity of the binding partners for each other. Fab A-scFv '52SR4' binding is detected to peptide 'GCN4' on the chip.

Figure 7:
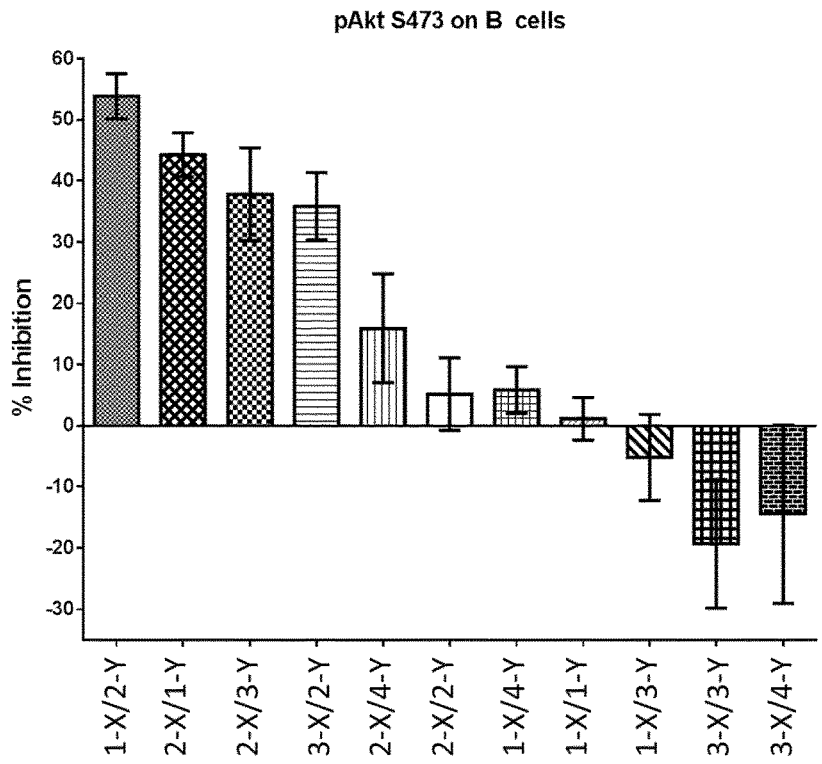

FIG. 7 is a bar chart of the relative potency of inhibition of phosphorylated Akt for bispecific and bivalent combinations of antibodies with specificity for antigen 3, antigen 1, antigen 4 and antigen 2.

Figure 8:
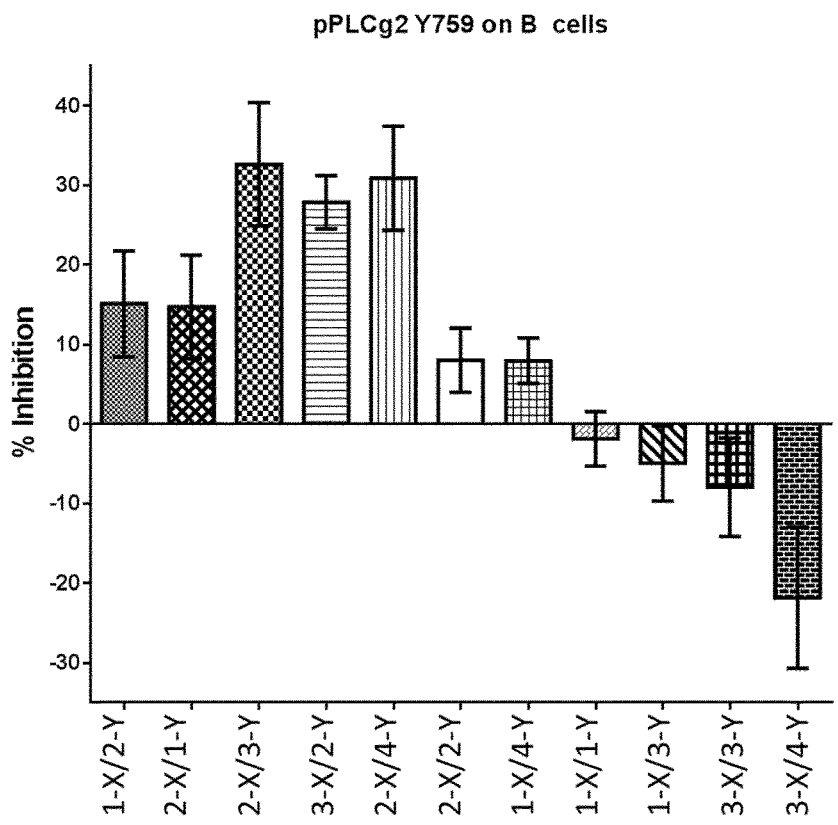

FIG. 8 is a bar chart of the relative potency of inhibition of phosphorylated PLCg2 for bispecific and bivalent combinations of antibodies with specificity for antigen 3, antigen 1, antigen 4 and antigen 2.

Figure 9:
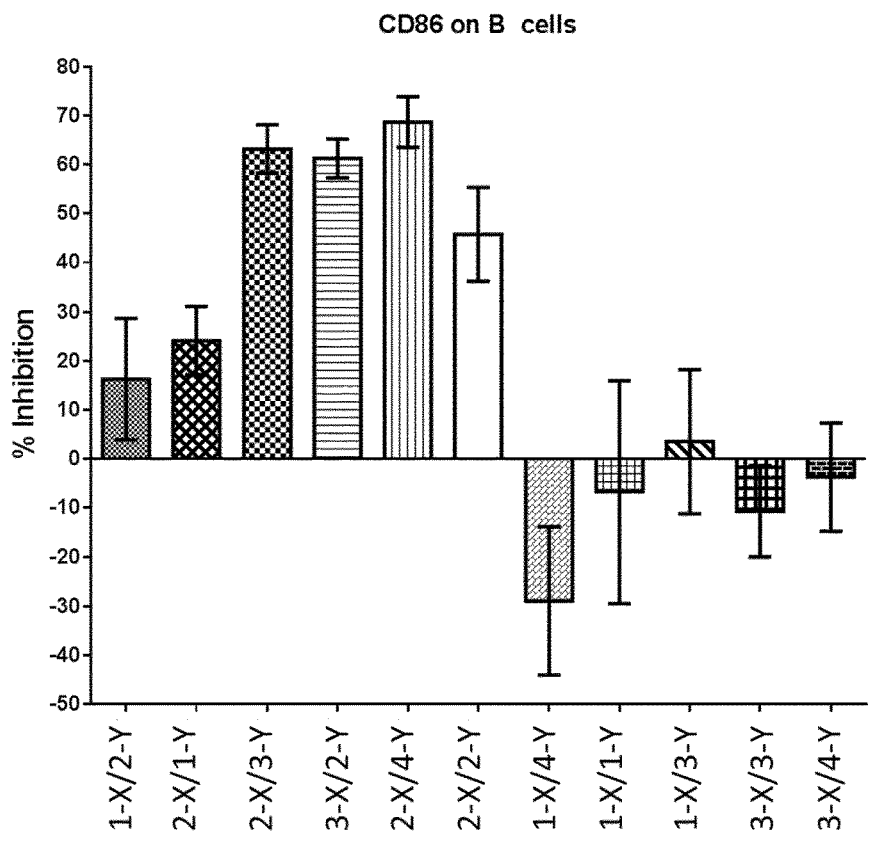

FIG. 9 is a bar chart of the relative potency of inhibition of CD86 expression for bispecific and bivalent combinations of antibodies with specificity for antigen 3, antigen 1, antigen 4 and antigen 2.

Figure 10:
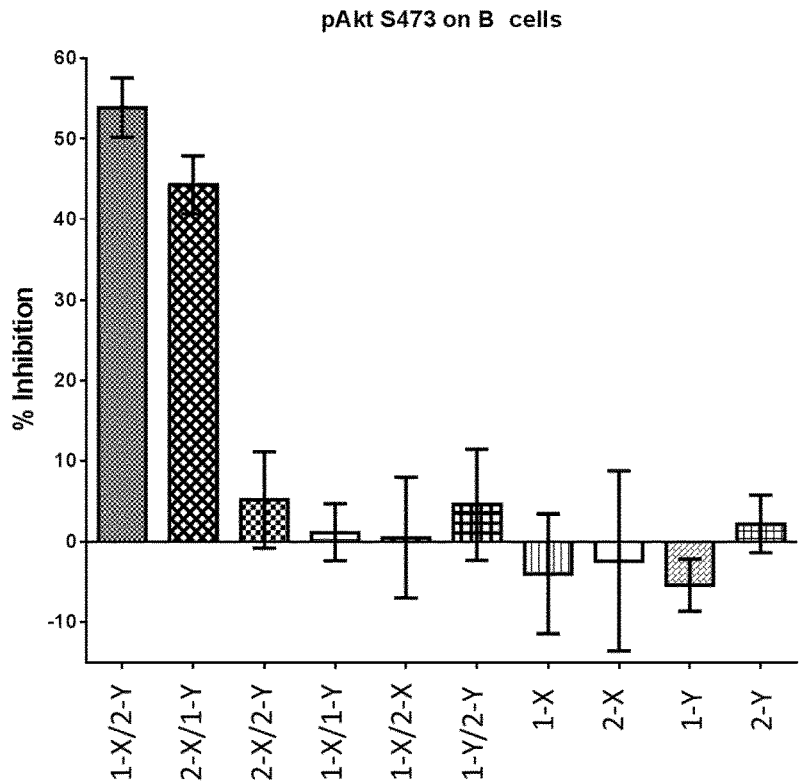

FIG. 10 is a bar chart of the relative potency of inhibition of phosphorylated Akt for bispecific, bivalent or mixtures of antibodies with specificity for antigen 1 and antigen 2 as well as single Fab' controls.

Figure 11:
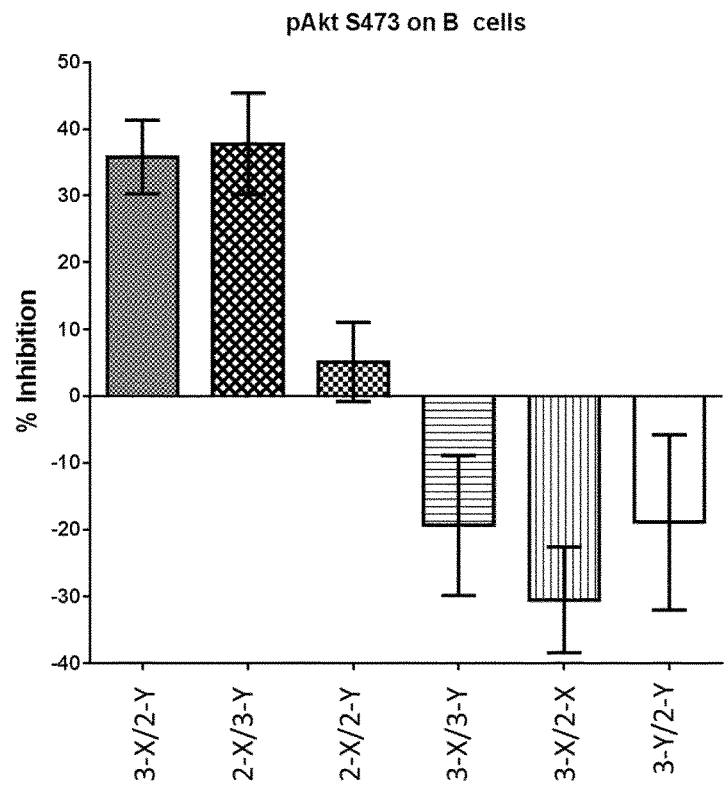

FIG. 11 is a bar chart of the relative potency of inhibition of phosphorylated Akt for bispecific, bivalent or mixtures of antibodies with specificity for antigen 3 and antigen 2.

Figure 12:
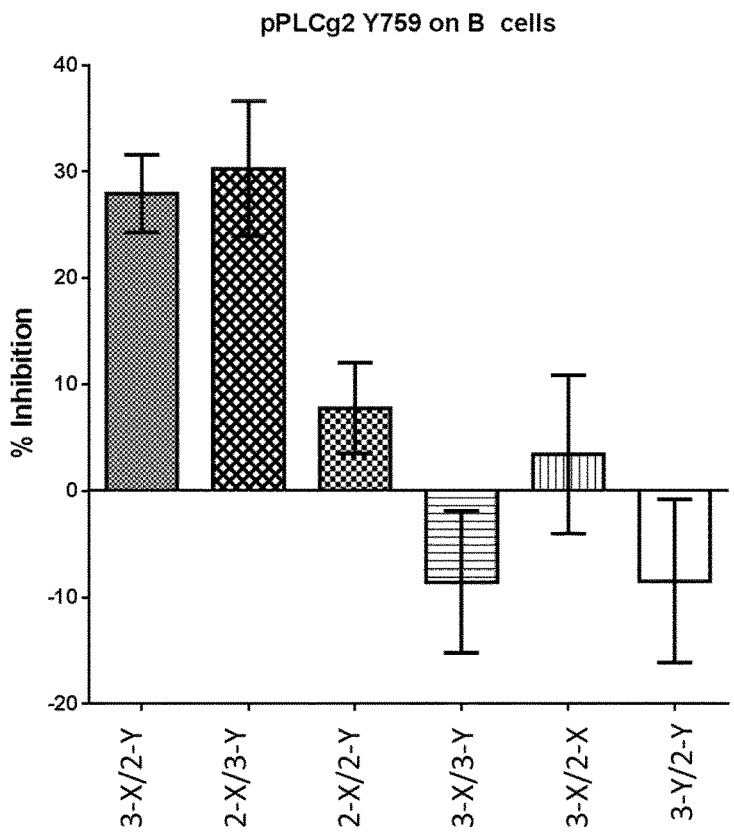

FIG. 12 is a bar chart of the relative potency of inhibition of phosphorylated PLCg2 for bispecific, bivalent or mixtures of antibodies with specificity for antigen 3 and antigen 2.

Figure 13:
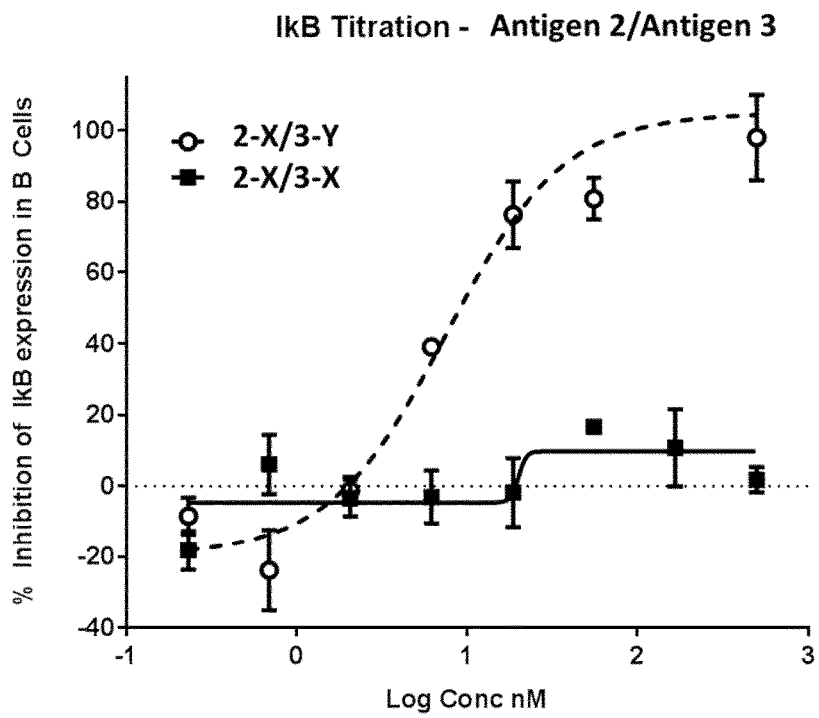

FIG. 13 is a graph showing the titration of the effect of the bispecific combination of anti-antigen 3 and anti-antigen 2 on total IkB levels in anti-IgM stimulated B cells.

Figure 14:
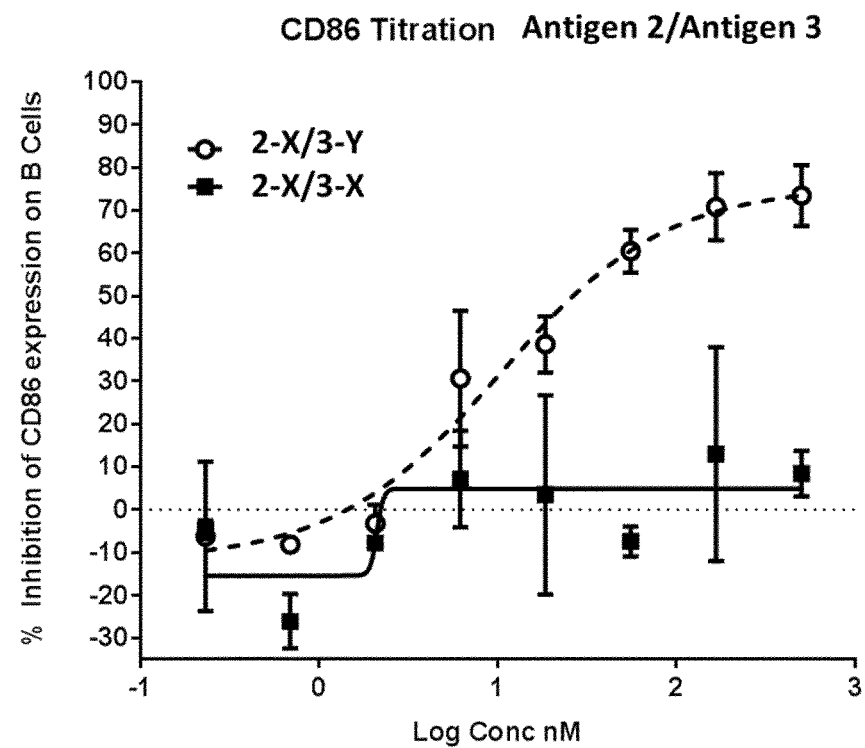

FIG. 14 is a graph showing the titration of the effect of the bispecific combination of antigen 3 and antigen 2 on CD86 expression on anti-IgM stimulated B cells.

Figure 15:
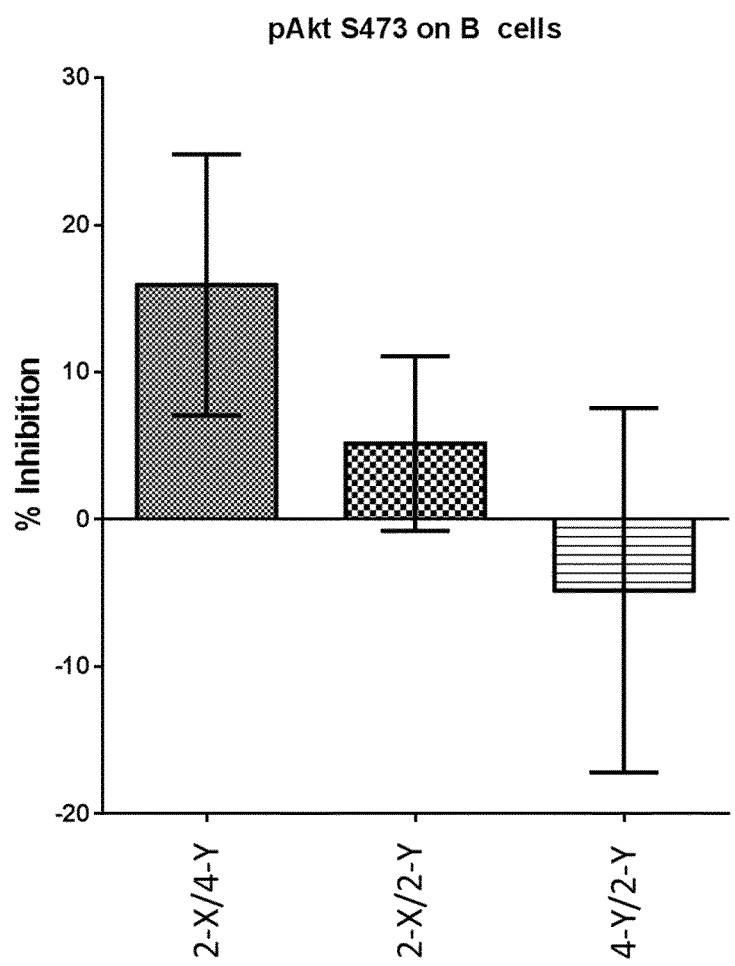

FIG. 15 is a bar chart of the relative potency of inhibition of phosphorylated Akt for bispecific, bivalent or mixtures of antibodies with specificity for antigen 4 and antigen 2.

Figure 16:
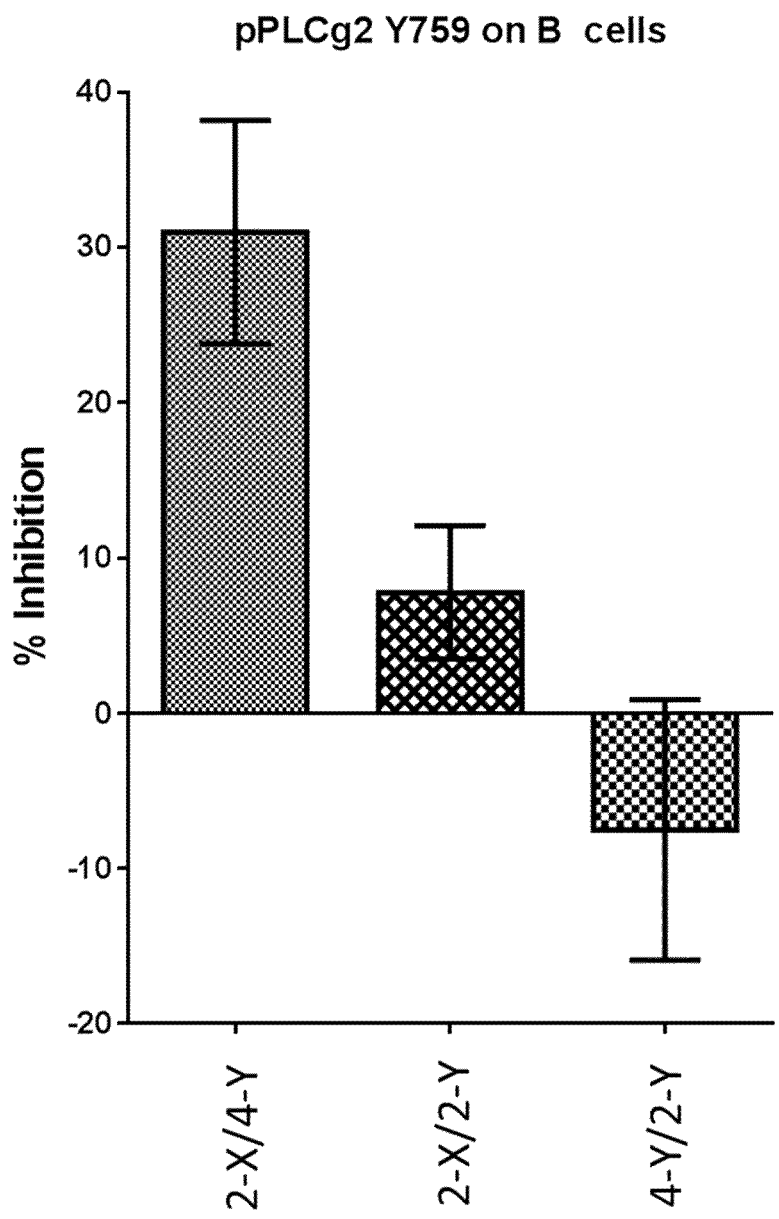

FIG. 16 is a bar chart of the relative potency of inhibition of phosphorylated PLCg2 for bispecific, bivalent or mixtures of antibodies with specificity for antigen 4 and antigen 2.

Figure 17:
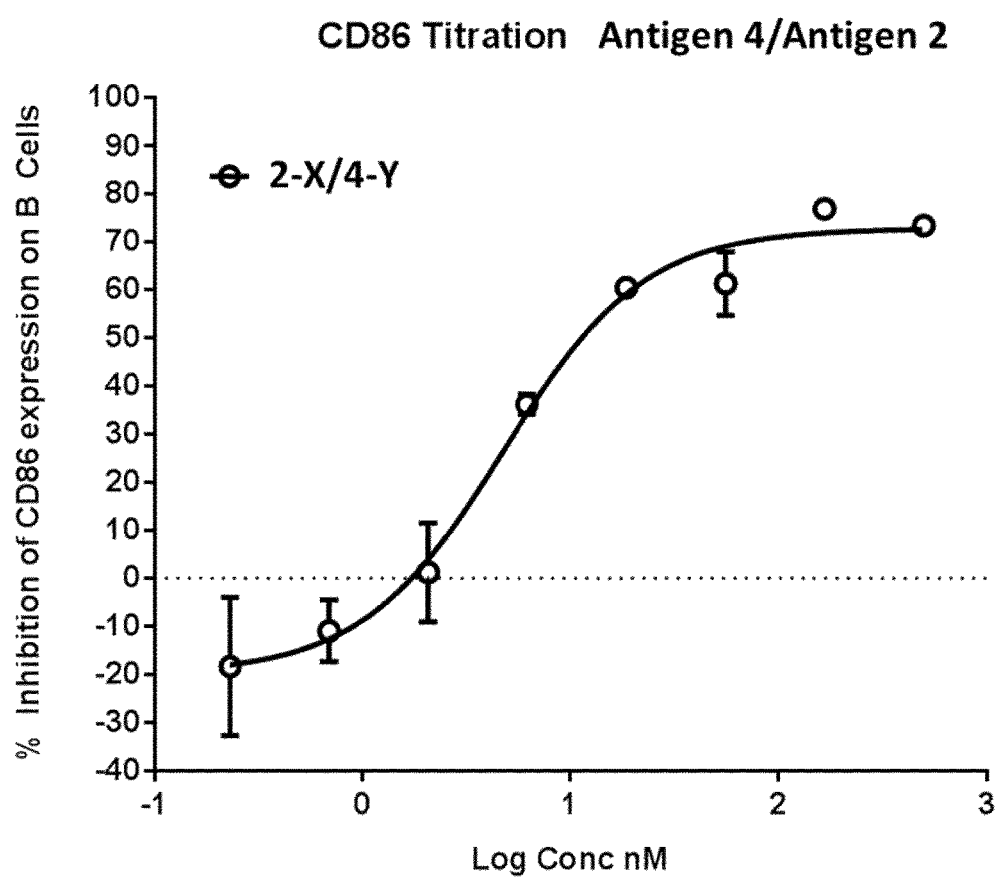

FIG. 17 is a graph showing the titration of the effect of the bispecific combination of antigen 4 and antigen 2 on CD86 expression on anti-IgM stimulated B cells.

Figure 18:
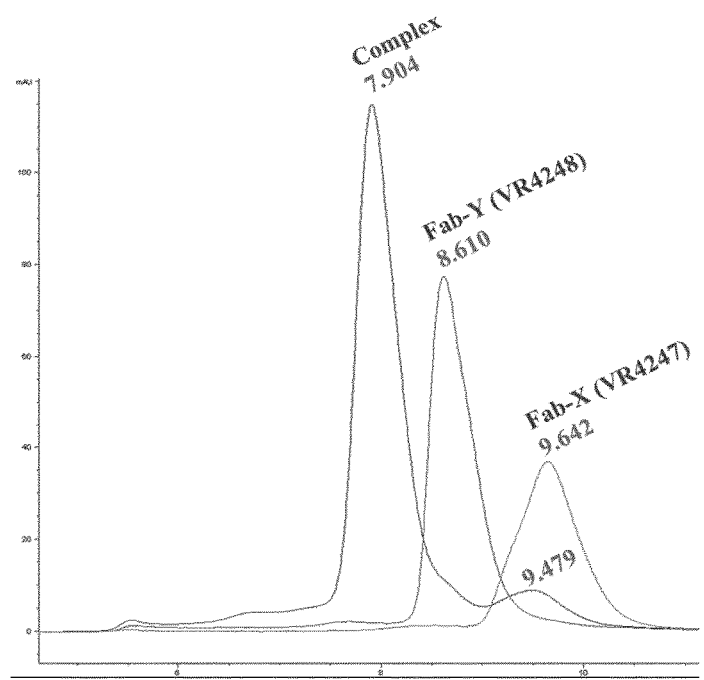

FIG. 18 is a graph showing the overlaid size exclusion A280 signal traces from experiment 1 of Example 11. The traces shown are: Fab-X (VR4247) control, Fab-Y (VR4248) control and 1 to 1 molar ratio mixture at 500 µg/ml of Fab-X (VR4247) and Fab-Y (VR4248) complex. Peaks were detected at an absorbance of 280 nm.

Figure 19:
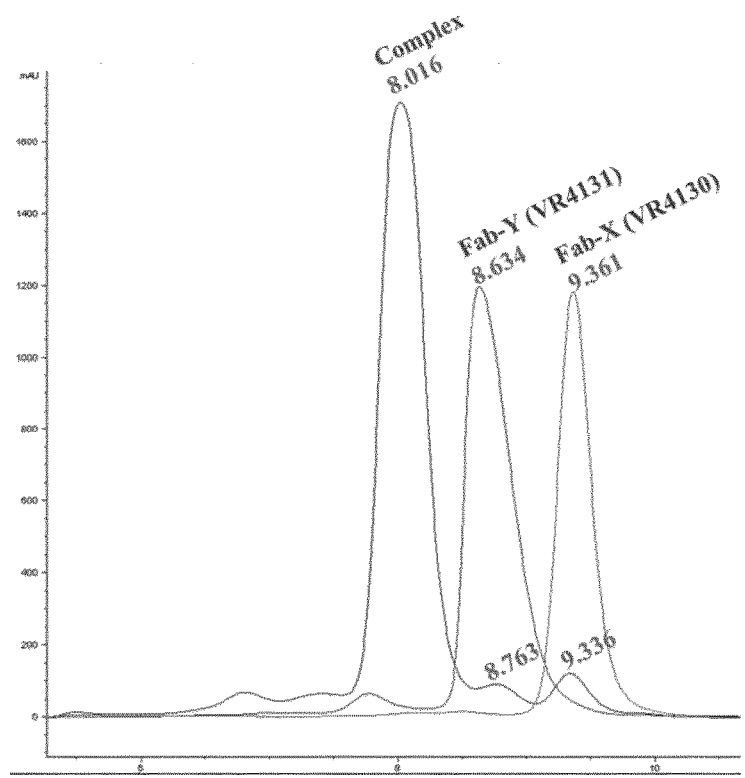

FIG. 19 is a graph showing the overlaid size exclusion A214 signal traces from experiment 2 of Example 11. The traces shown are: Fab-X (VR4130) control, Fab-Y (VR4131) control and 1 to 1 molar ratio mixture at 500 µg/ml of Fab-X (VR4130) and Fab-Y (VR4131) complex. Peaks were detected at an absorbance of 214 nm.

Figure 20:
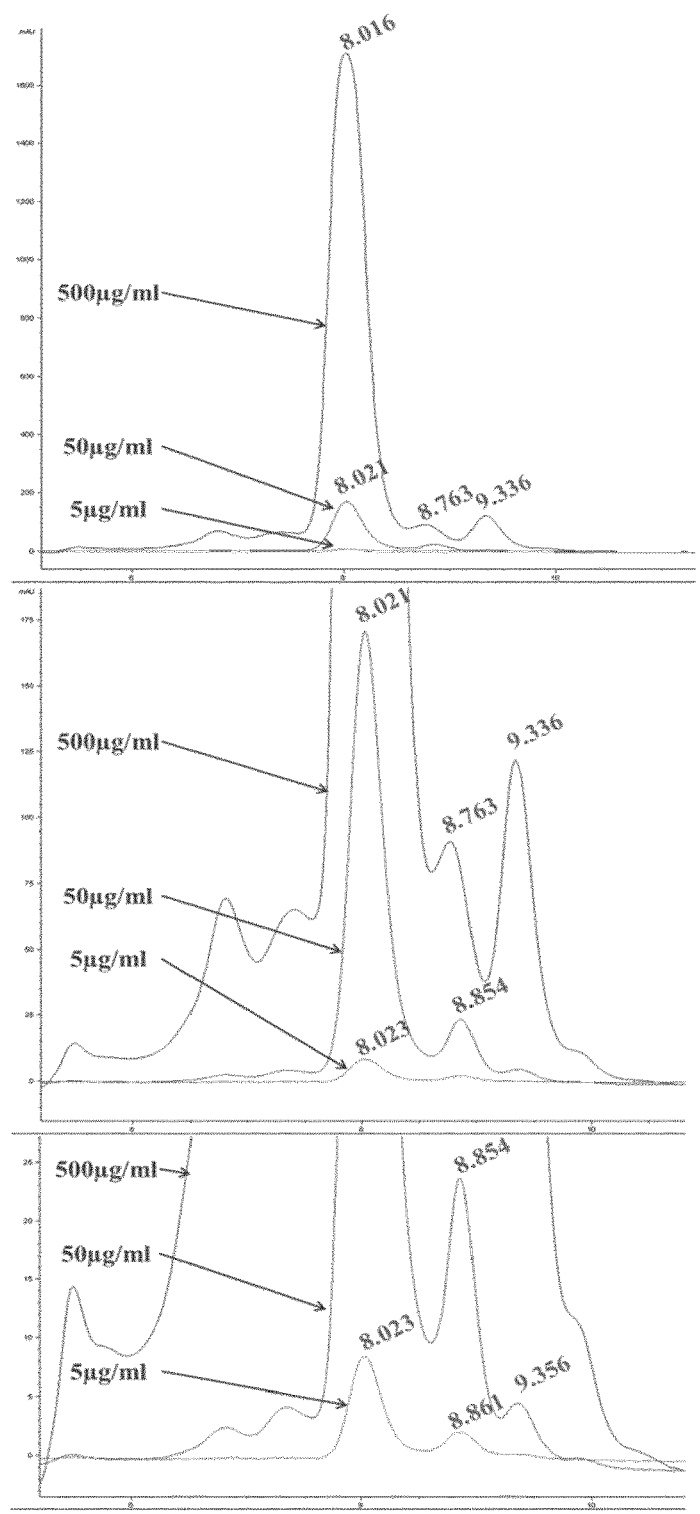

FIG. 20 is a graph showing the overlaid size exclusion A214 signal traces from experiment 2 of Example 11. The traces shown are all Fab-X (VR4130)/Fab-Y (VR4131) 1 to 1 molar ratio mixtures at 500 µg/ml, 50 µg/ml and 5 µg/ml as indicated. Peaks were detected at an absorbance of 214 nm.

Figure 21:
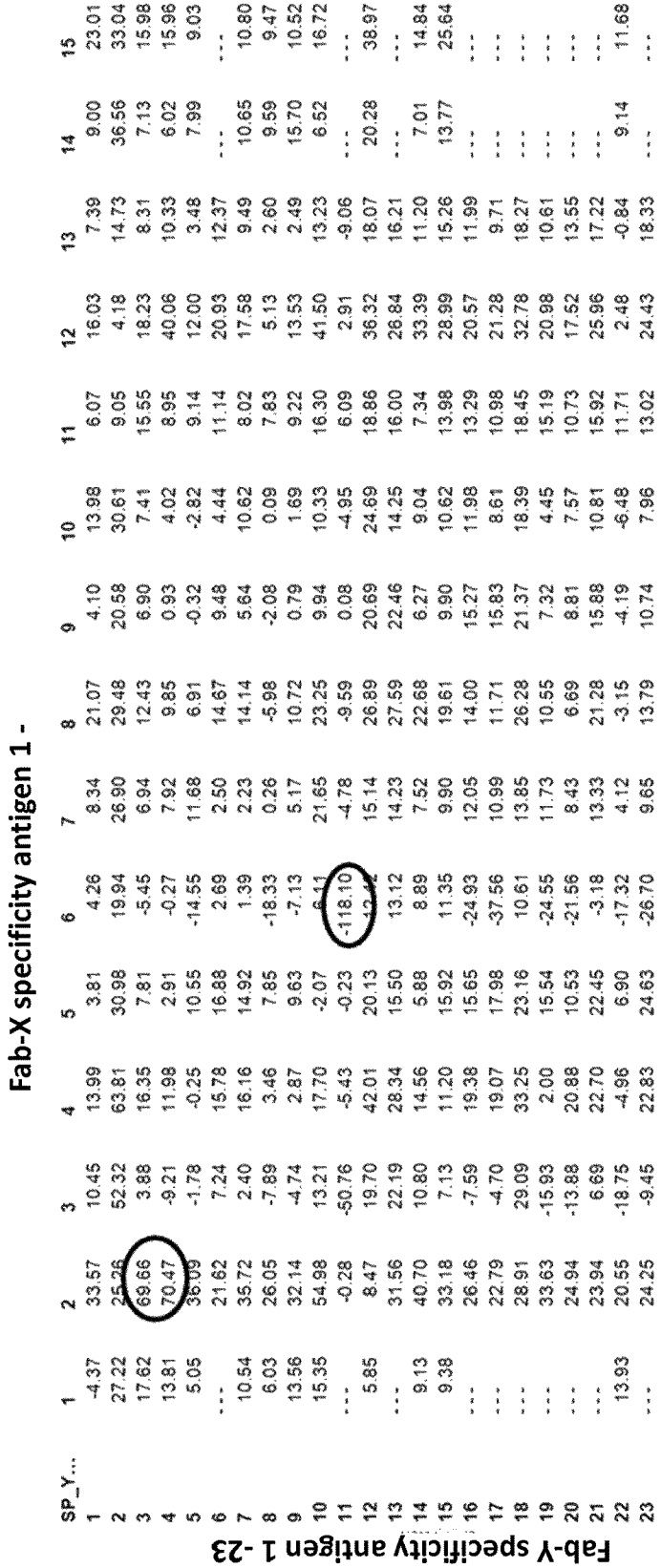

FIG. 21 is a table showing the data for the antigen grid cross specificities. Values are percentage inhibition (negative value for activation) of phosphorlylation of Syk & represent the mean of multiple V region combinations evaluated.

FIG. 22 is a table showing the data for the antigen grid cross specificities. Values are percentage inhibition (negative value for activation) of phosphorlylation of PLCg2 & represent the mean of multiple V-region combinations evaluated.

FIG. 23 is a table showing the data for the antigen grid cross specificities. Values are percentage inhibition (negative value for activation) of phosphorlylation of AKT & represent the mean of multiple V region combinations evaluated.

Figure 24:
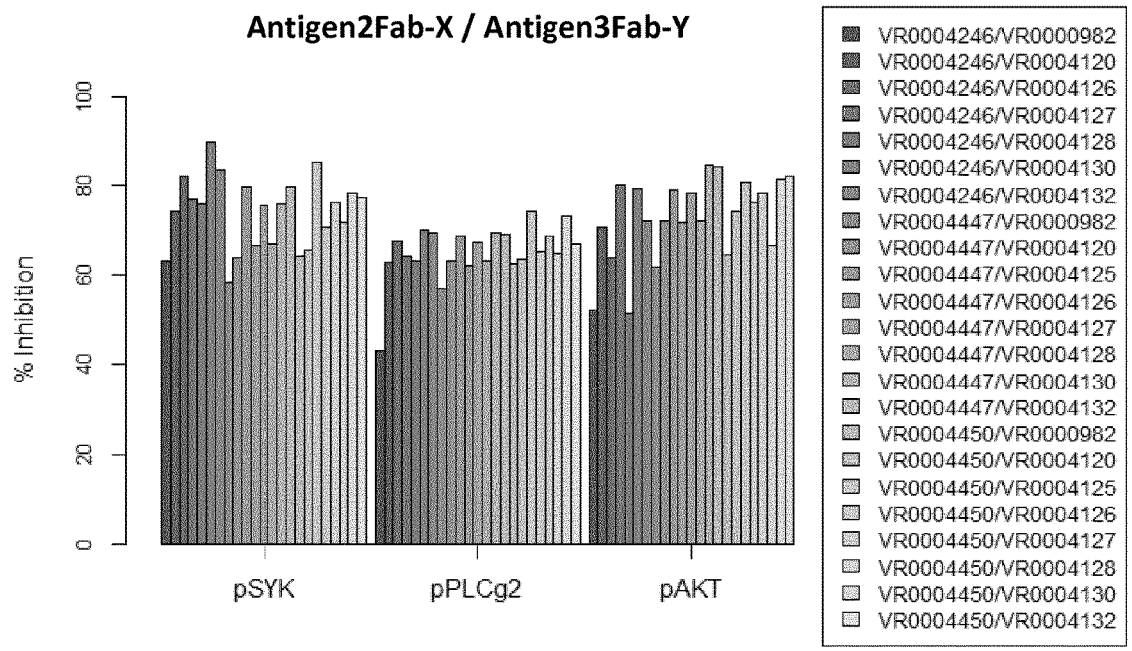
Figure 25:
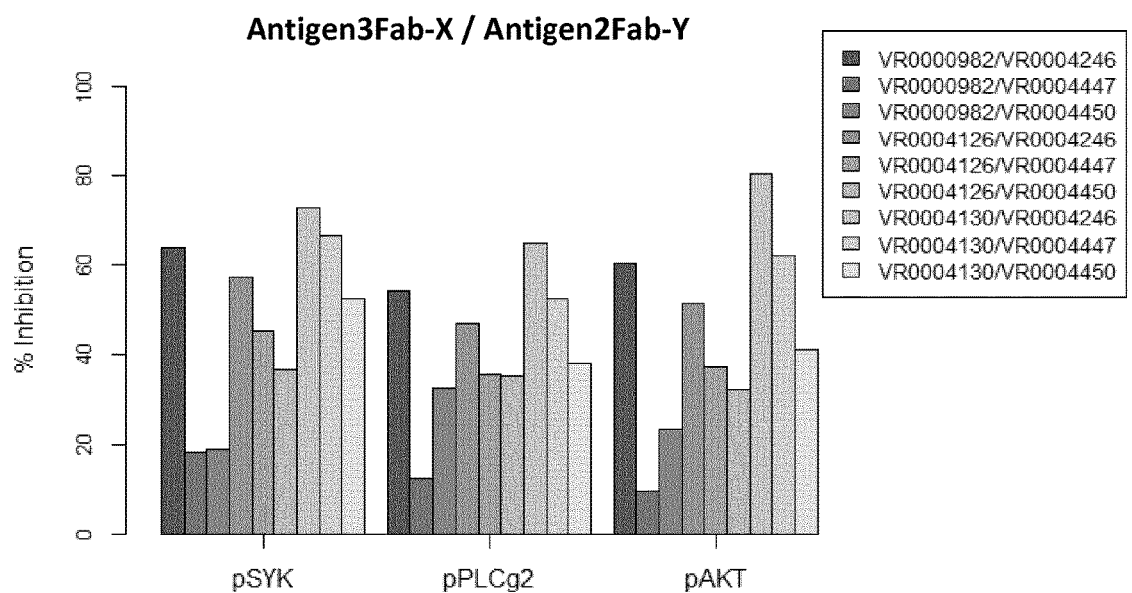

FIG. 24 is a graph showing the percentage inhibition of the phosphorlylation of Syk, PLCg2 & AKT for each V-region combination for antigen 2 in Fab-X combined with antigen 3 in Fab-Y FIG. 25 is a graph showing the percentage inhibition of the phosphorlylation of Syk, PLCg2 & AKT of the phosphorlylation of Syk, PLCg2 & AKT for each V-region combination for antigen 3 in Fab-X combined with antigen 2 in Fab-Y.

Figure 26:
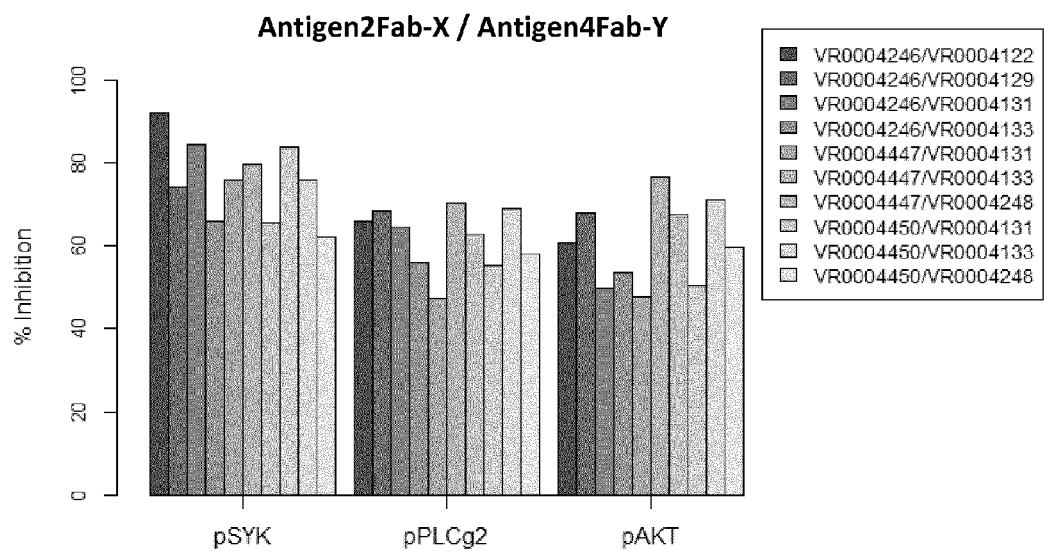

FIG. 26 is a graph showing the percentage inhibition of the phosphorlylation of Syk, PLCg2 & AKT for each V region combination for antigen 2 in Fab-X combined with antigen 4 in Fab-Y.

Figure 27:
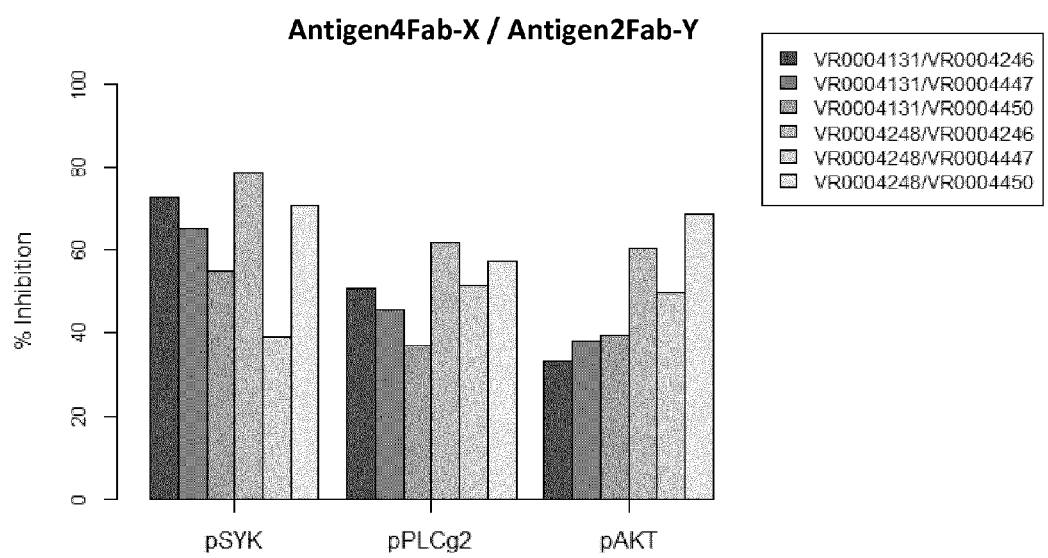

FIG. 27 is a graph showing the percentage inhibition of the phosphorlylation of Syk, PLCg2 & AKT for each V region combination for antigen 4 in Fab-X combined with antigen 2 in Fab-Y.

Figure 28:
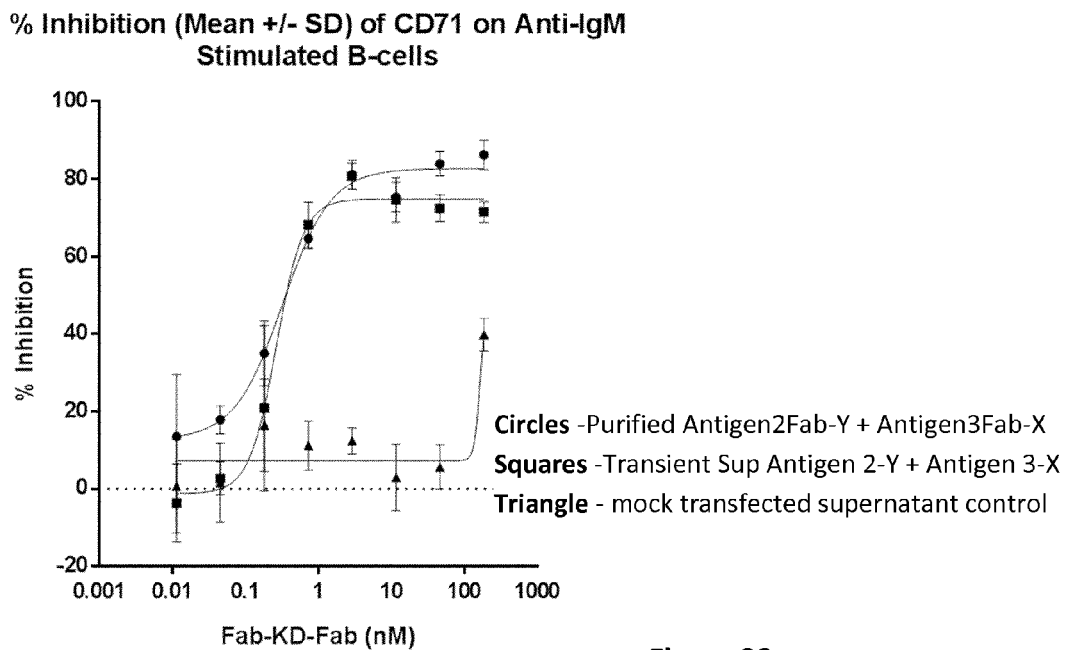

FIG. 28 is a graph showing the data for the percentage inhibition of anti-IgM induced CD71 expression on B-cells, by antigen3Fab'-X and antigen2-Fab'-Y when combination as either purified Fab' or from transient supernatant.

Circles—Purified Antigen2Fab-Y+Antigen3Fab-X $IC_{50}$ 0.3224 nM

Squares—Transient Sup Antigen2-Y+Antigen3-X $IC_{50}$ 0.2640 nM

Triangle—Mock transfected supernatant control

Figure 29:
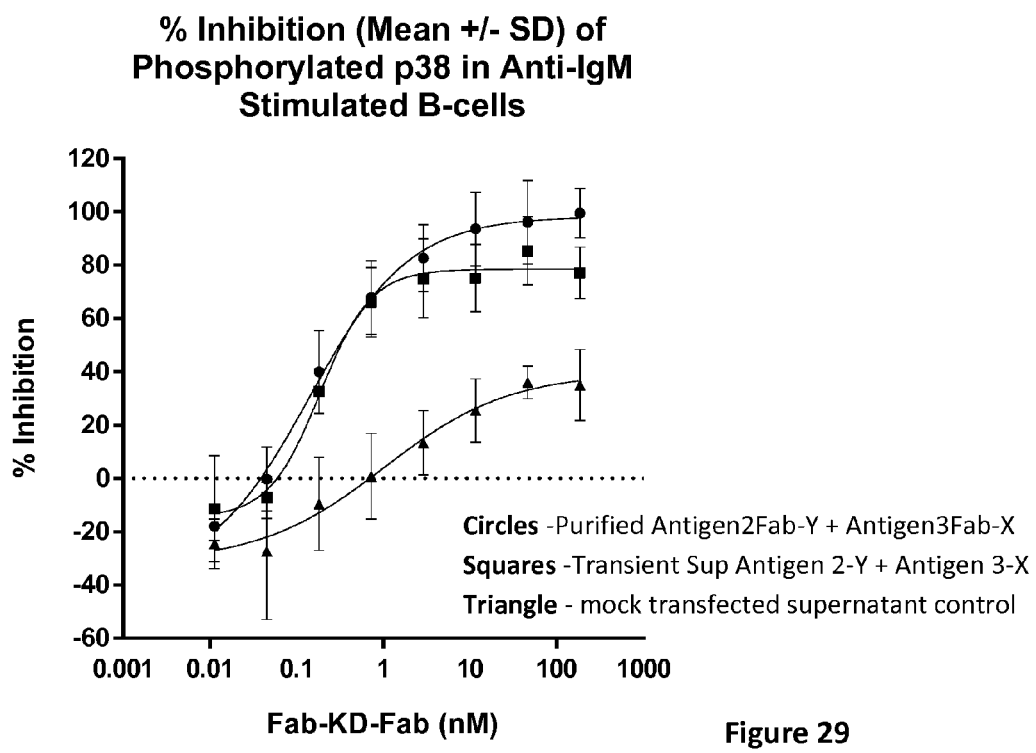

FIG. 29 is a graph showing the data for the percentage inhibition of anti-IgM induced phosphorylation of p38 in B-cells, by antigen3-Fab'-X and antigen 2-Fab'-Y when combination as either purified Fab' or from transient supernatant.

Circles—Purified Antigen2Fab-Y+Antigen3Fab-X $IC_{50}$ 0.1413 nM

Squares—Transient Sup Antigen 2-Y+Antigen 3-X $IC_{50}$ 0.1861 nM

Triangle—Mock transfected supernatant control

Key for FIGS. 30 to 33

Figure 30:
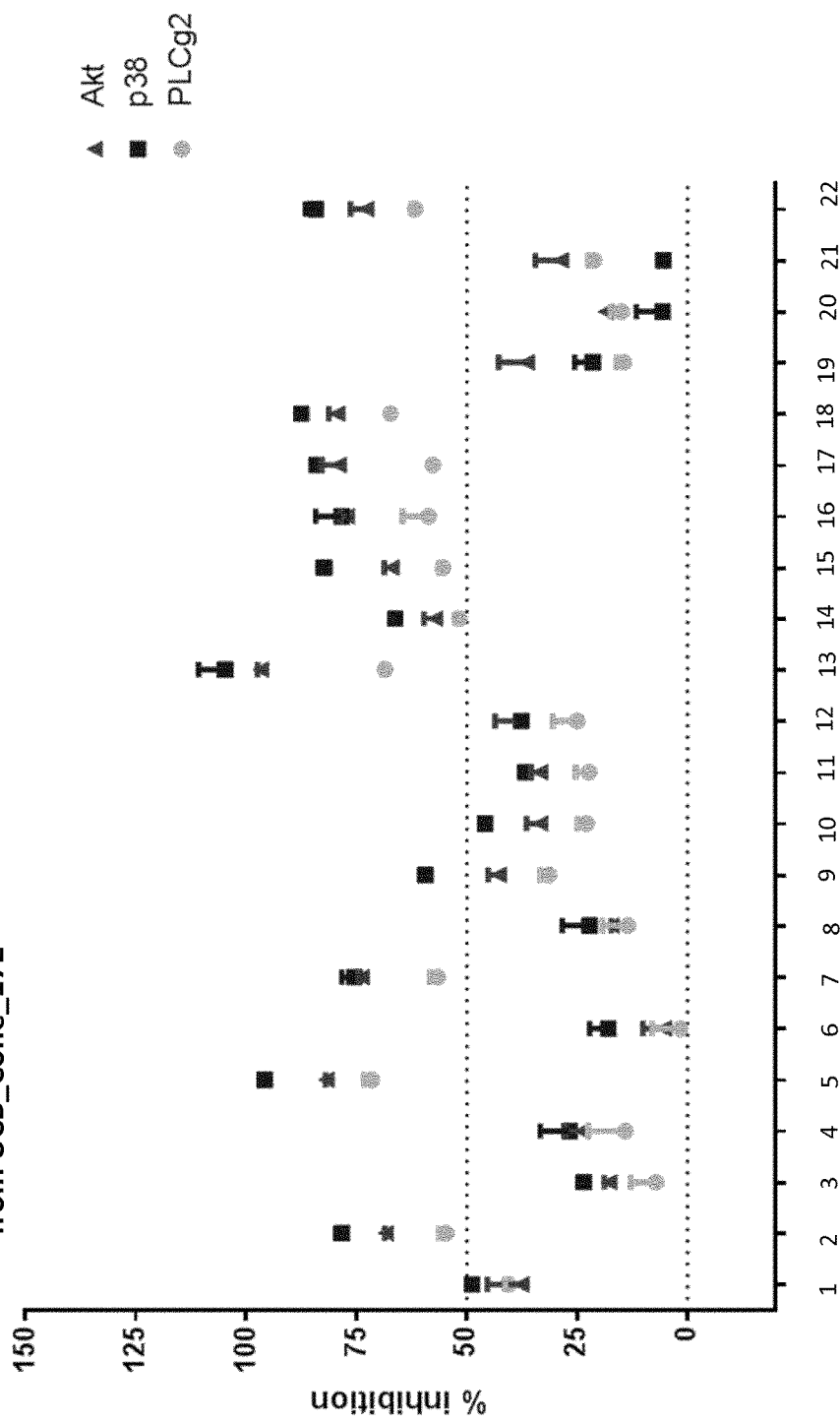

1. Antigen2Fab-Y (VR4447)+Antigen3Fab-X (VR6066); 2. Antigen2Fab-Y (VR4447)+Antigen3Fab-X (VR6078); 3. Antigen2Fab-Y (VR4447)+Antigen3Fab-X (VR6079); 4. Antigen2Fab-Y (VR4447)+Antigen3Fab-X (VR6080); 5. Antigen2Fab-Y (VR4447)+Antigen3Fab-X (VR6082); 6. Antigen2Fab-Y (VR4447)+Antigen3Fab-X (VR6067); 7. Antigen2Fab-Y (VR4447)+Antigen3Fab-X (VR6068); 8. Antigen2Fab-Y (VR4447)+Antigen3Fab-X (VR6070); 9. Antigen2Fab-Y (VR4447)+Antigen3Fab-X (VR6071); 10. Antigen2Fab-Y (VR4447)+Antigen3Fab-X (VR6073); 11. Antigen2Fab-Y (VR4447)+Antigen3Fab-X (VR6075); 12. Antigen2Fab-Y (VR4447)+Antigen3Fab-X (VR6076); 13. Antigen2Fab-Y (VR4447)+Antigen3Fab-X (VR6077); 14. Antigen2Fab-Y (VR4447)+Antigen3Fab-X (VR6069); 15. Antigen2Fab-Y (VR4447)+Antigen3Fab-X (VR6072); 16. Antigen2Fab-Y (VR4447)+Antigen3Fab-X (VR6074); 17. Antigen2Fab-Y (VR4447)+Antigen3Fab-X (VR6081); 18. Antigen2Fab-Y (VR4447)+Antigen3Fab-X (TSUP-24117); 19. Antigen2Fab-Y (VR4447)+Antigen3Fab-X (TSUP-24432); 20. Mock supe 1; 21. Mock supe 2; 22. Antigen2Fab-Y (VR4447)+Antigen3Fab-X (4126) purified FIG. 30 is a graph showing the inhibition of phospho readouts by purified antigen2-specific Fab-Y (VR4447) combined with antigen3-specific Fab-X transients on IgM stimulated B-cells from UCB_Cone 172.

Figure 31:
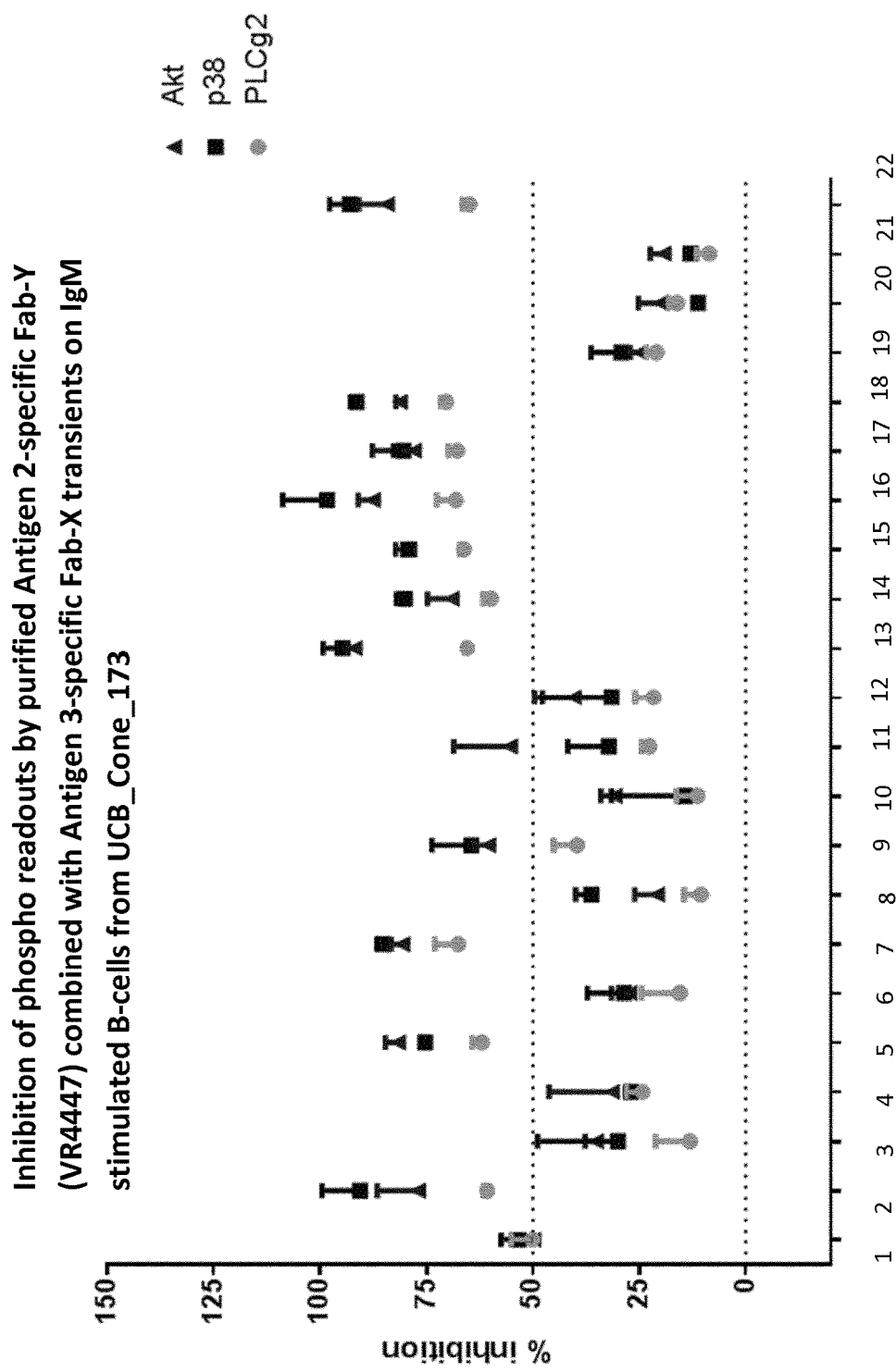

FIG. 31 is a graph showing the inhibition of phosphor readouts by purified antigen 2-specific Fab-Y (VR4447) combined with antigen 3-specific Fab-X transients on IgM stimulated B-cells from UCB_Cone 173

Figure 32:
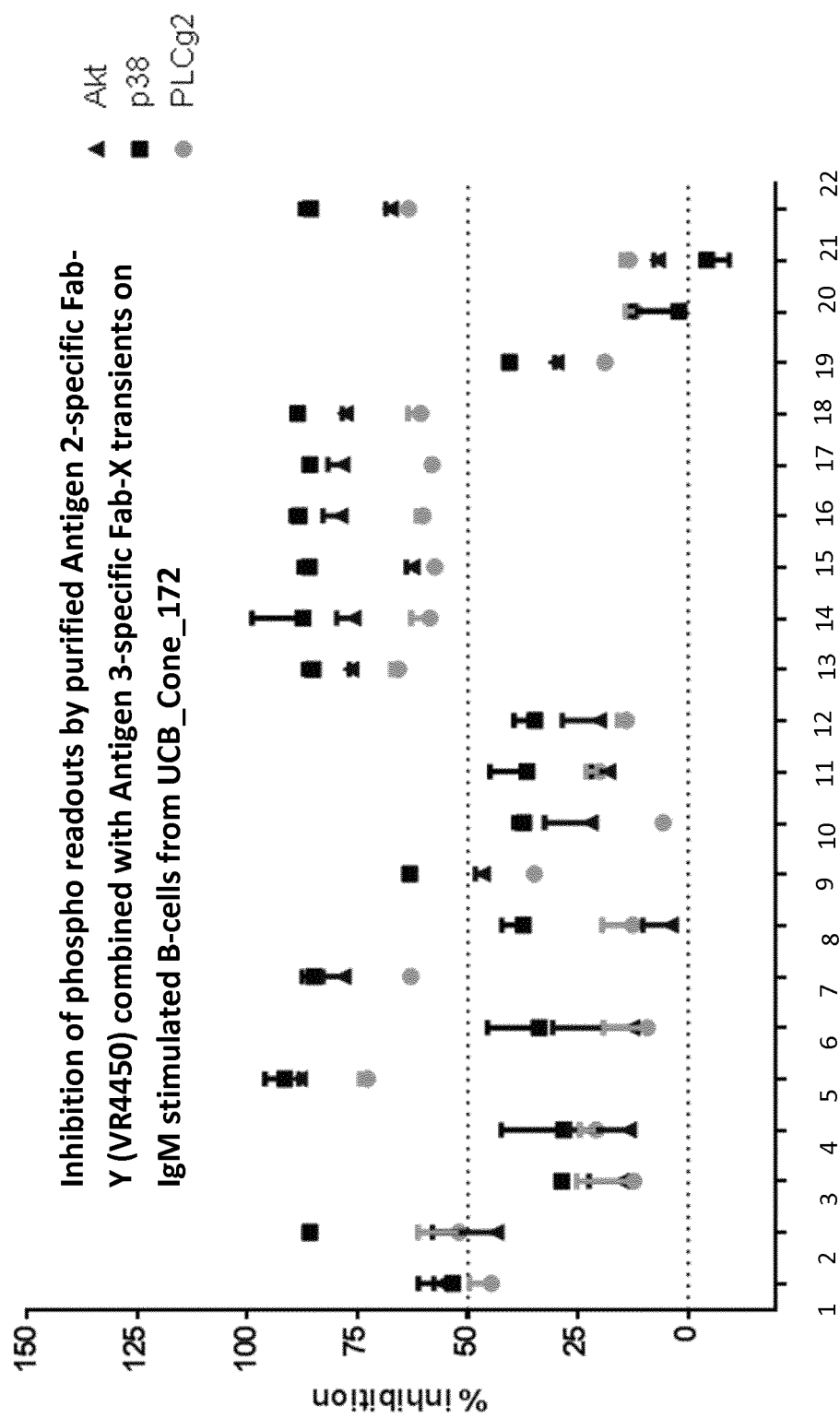

FIG. 32 Inhibition of phospho readouts by purified antigen 2-specific Fab-Y (VR4450) combined with antigen 3-specific Fab-X transients on IgM stimulated B-cells from UCB_Cone 172

Figure 33:
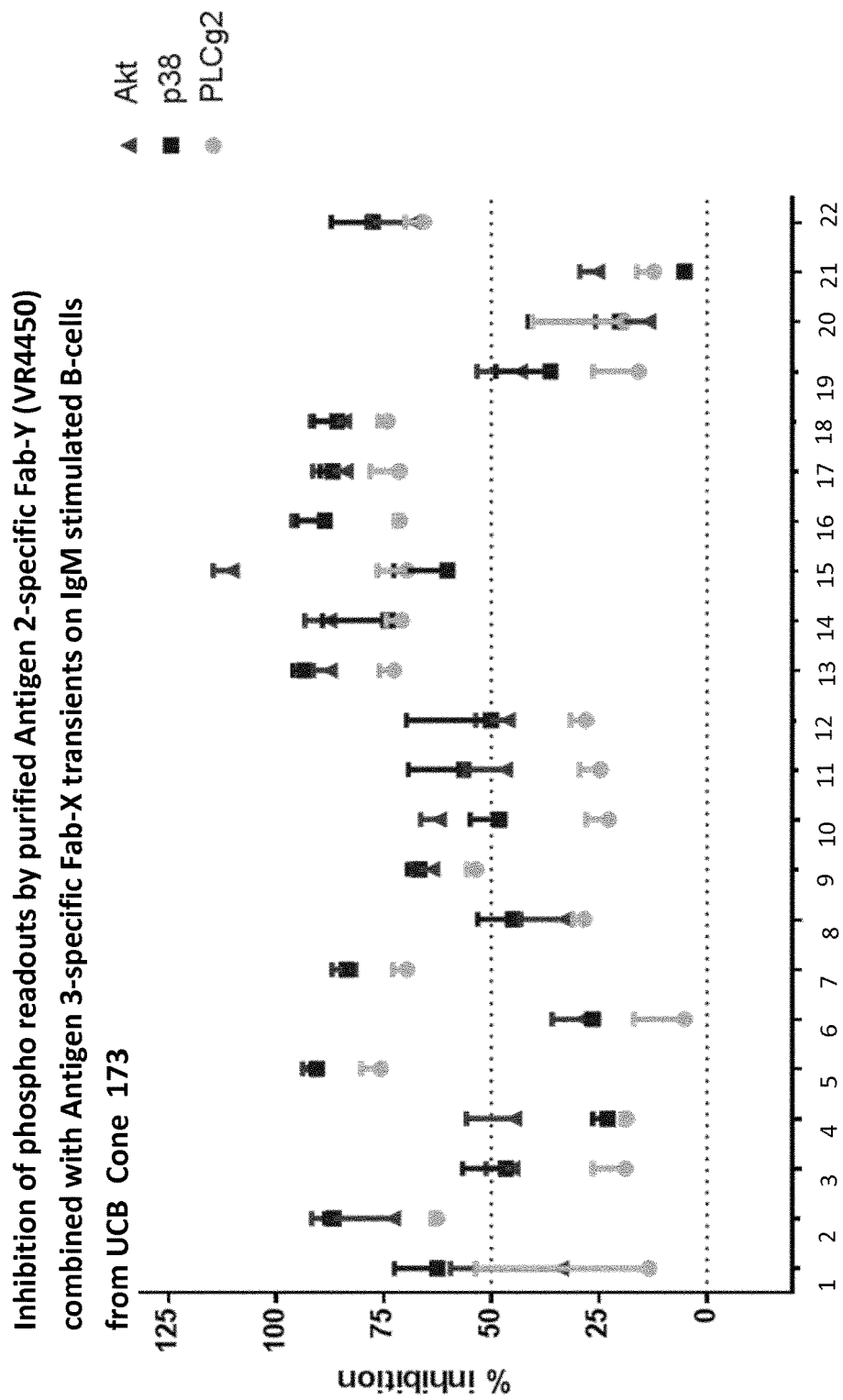

FIG. 33 Inhibition of phospho readouts by purified antigen 2-specific Fab-Y (VR4450) combined with antigen 3-specific Fab-X transients on IgM stimulated B-cells from UCB_Cone 173

Figure 34:
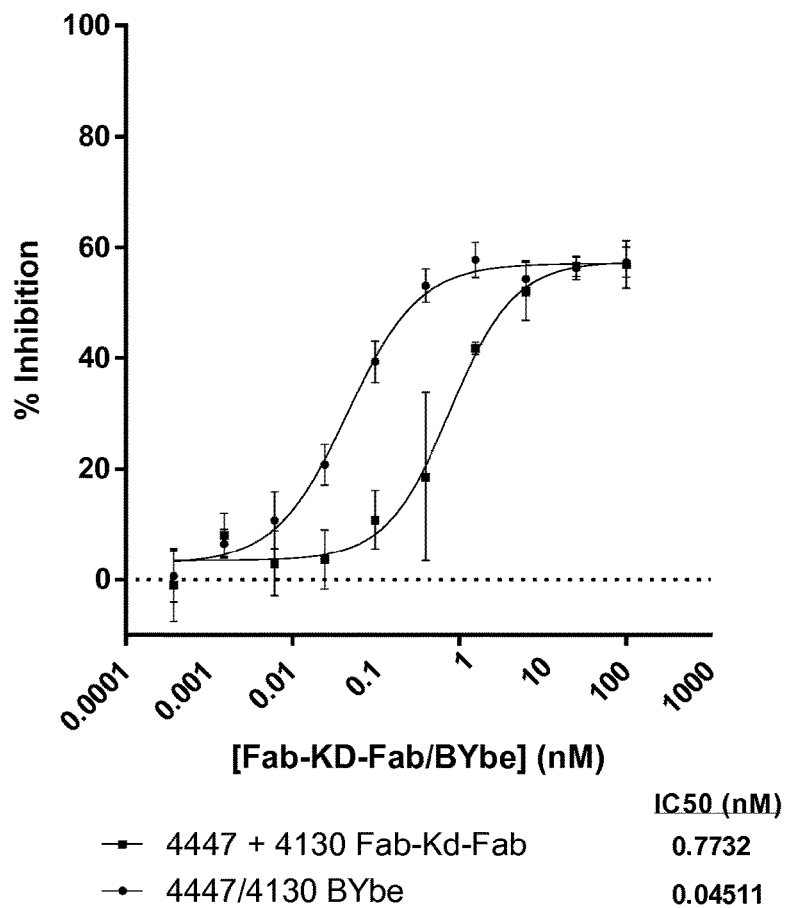
Figure 35:
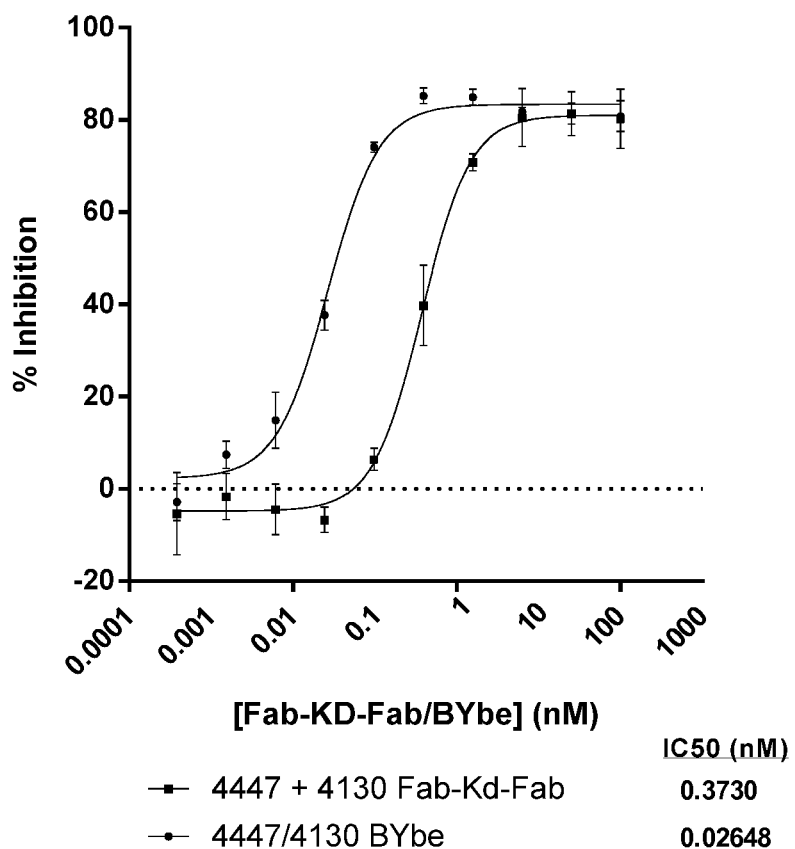
Figure 36:
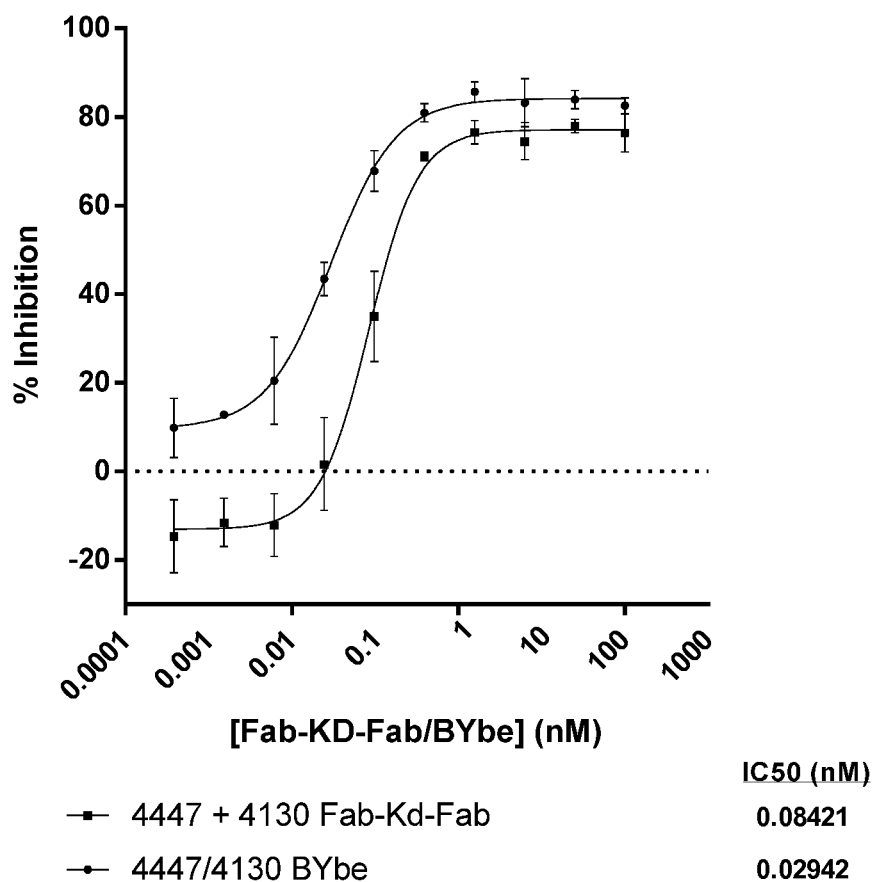
Figure 37:
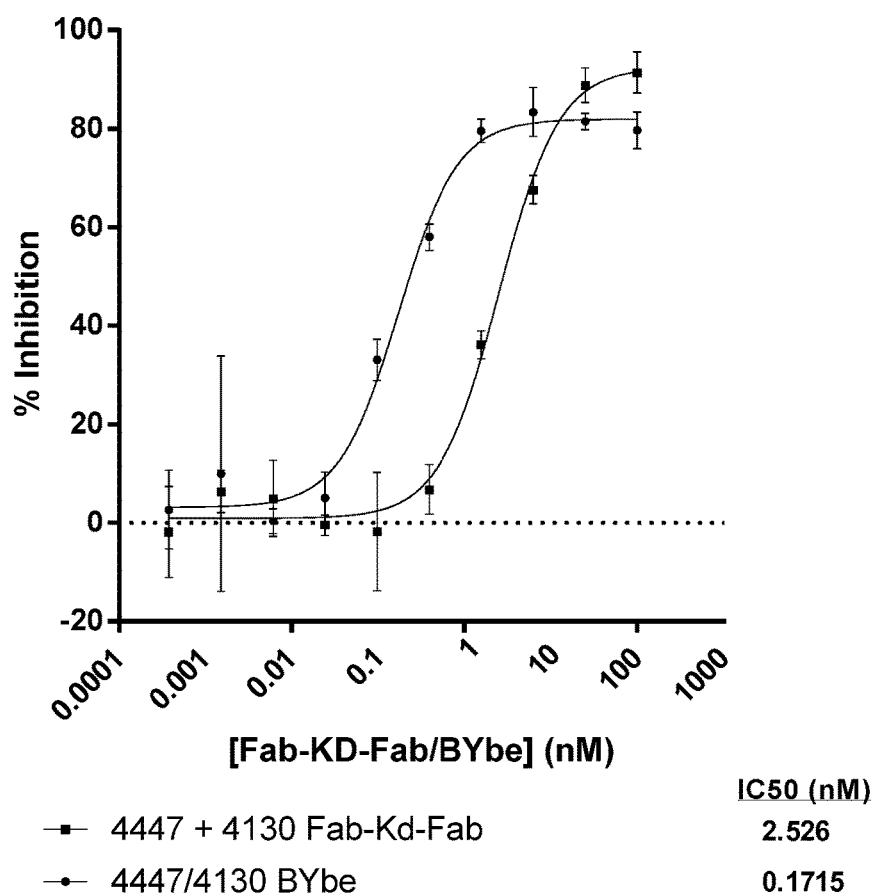
Figure 38:
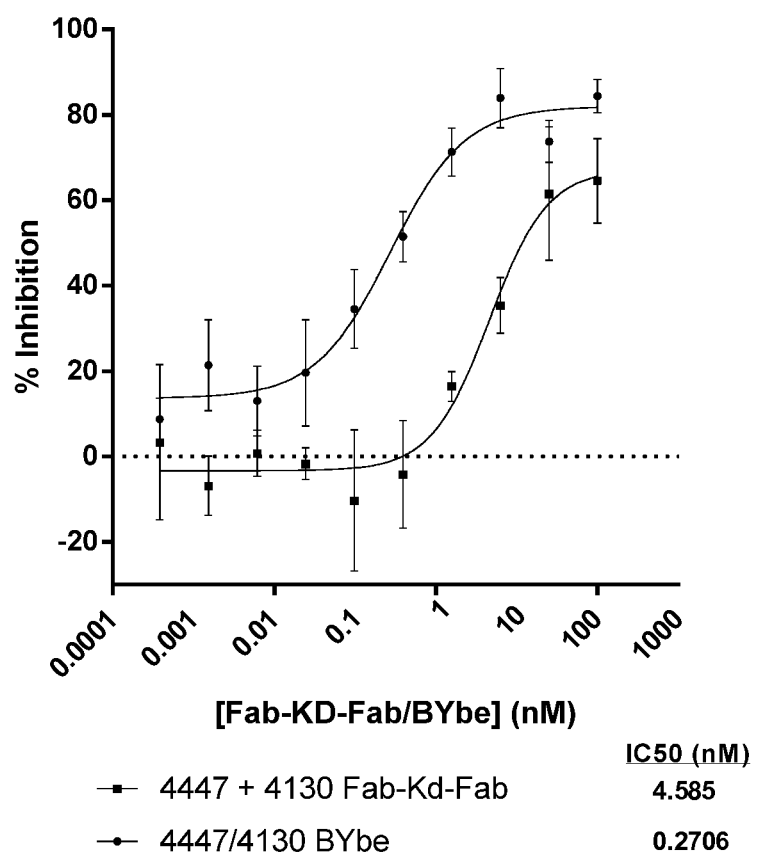

FIG. 34 shows data for the percentage inhibition of anti-IgM induced phosphorylated PLCγ2 in B-cells, by antigen 3 and antigen 2 specific Fab-Kd-Fab or BYbe FIG. 35 shows data for the percentage inhibition of anti-IgM induced phosphorylated P38 in B-cells, by antigen 3 and antigen 2 specific Fab-Kd-Fab or BYbe FIG. 36 shows data for the percentage inhibition of anti-IgM induced phosphorylated Akt in B-cells, by antigen 3 and antigen 2 specific Fab-Kd-Fab or BYbe FIG. 37 shows data for the percentage inhibition of anti-IgM induced CD71 expression on B-cells, by antigen 3 and antigen 2 specific Fab-Kd-Fab or BYbe FIG. 38 shows data for the percentage inhibition of anti-IgM induced CD40 expression on B-cells, by antigen 3 and antigen 2 specific Fab-Kd-Fab or BYbe.

Figure 39:
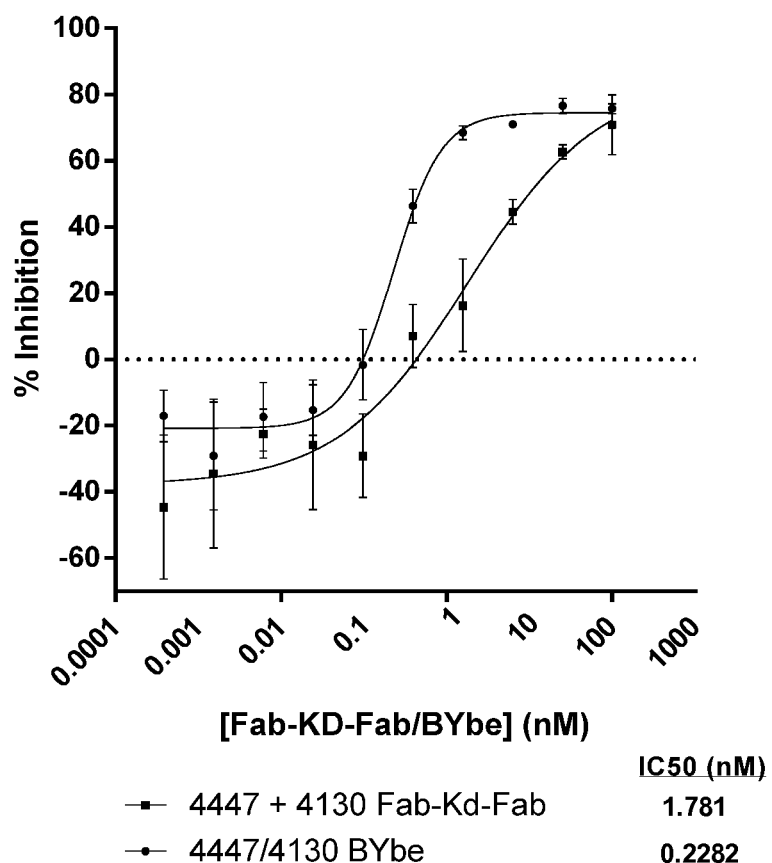
Figure 40:
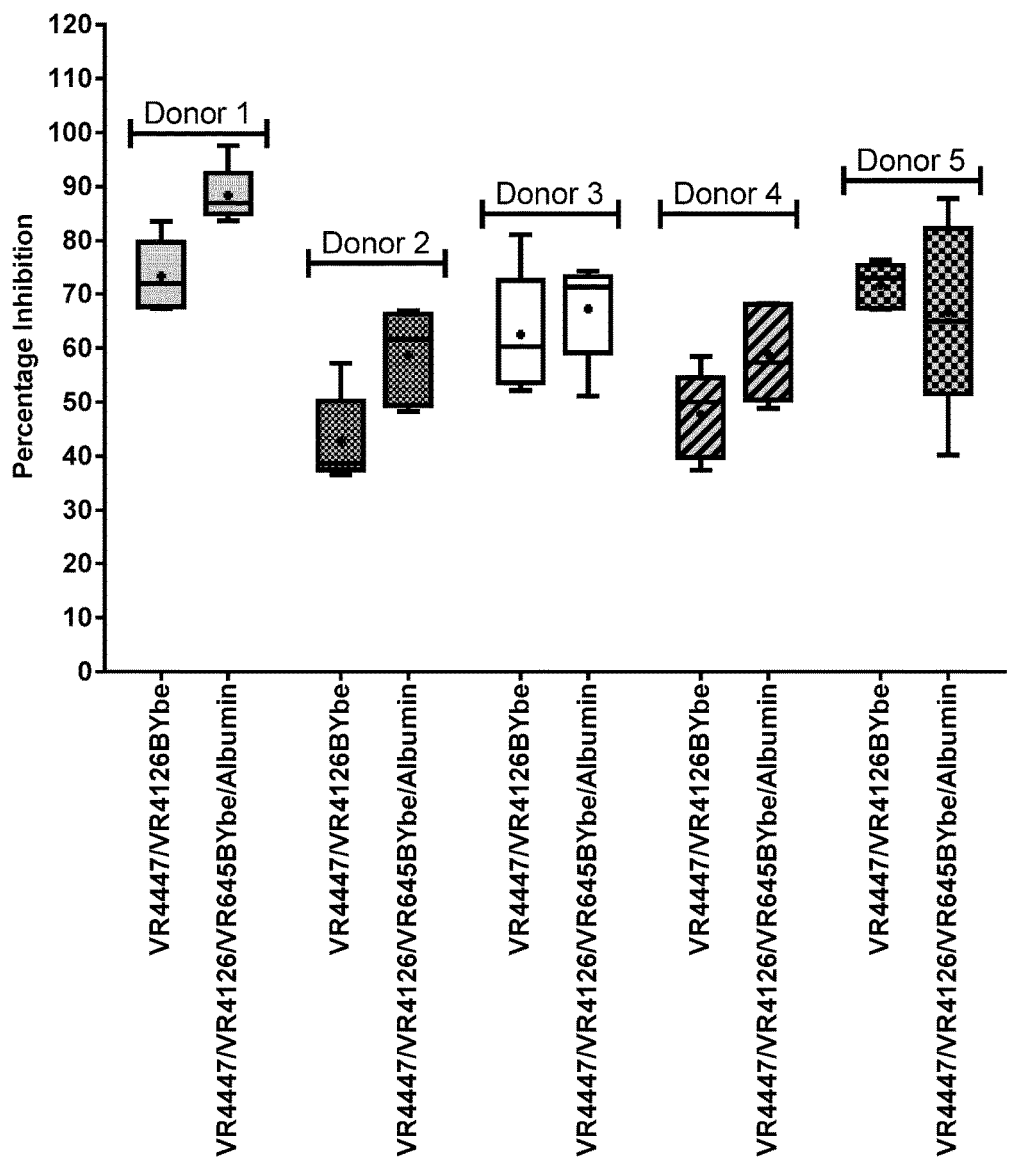
Figure 41:
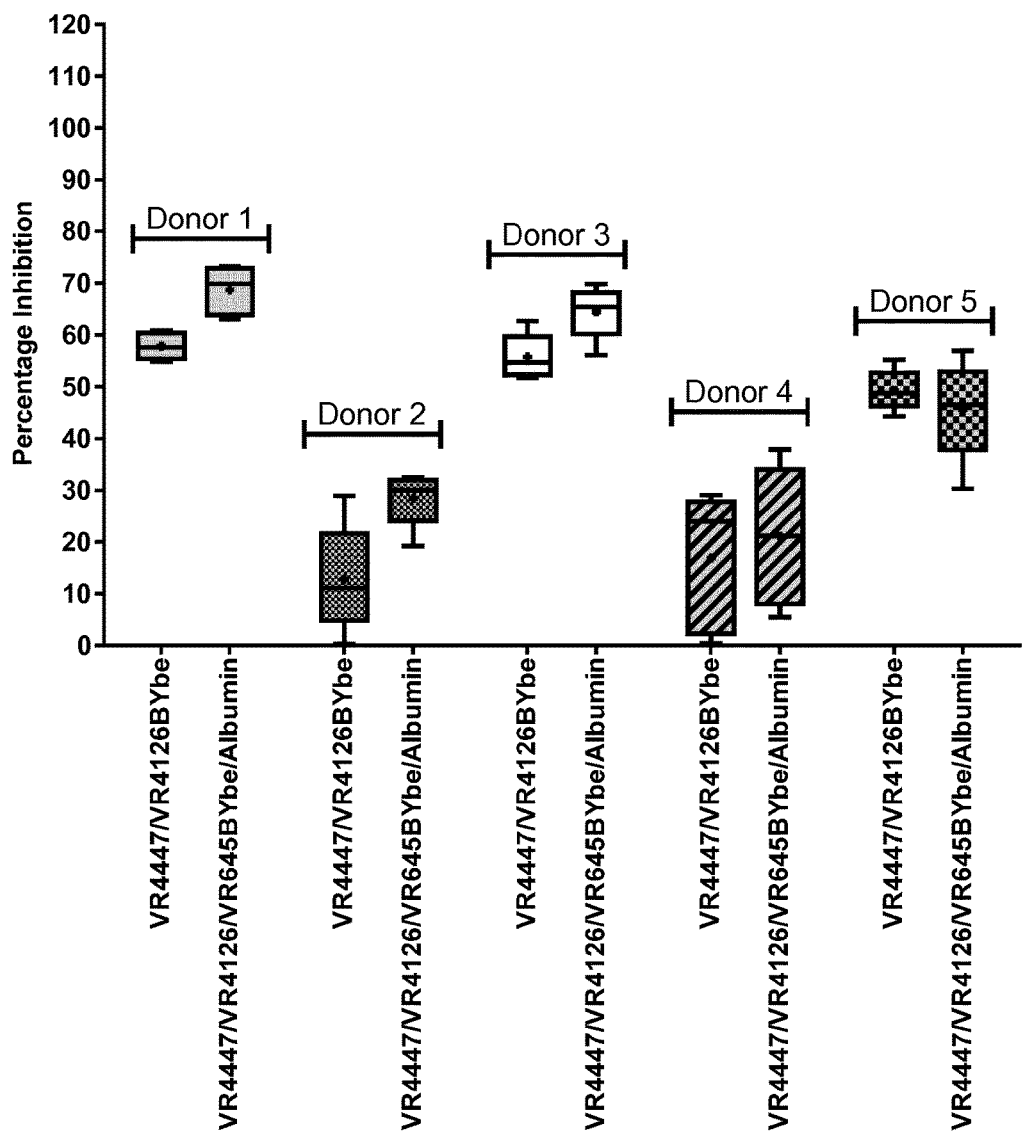
Figure 42:
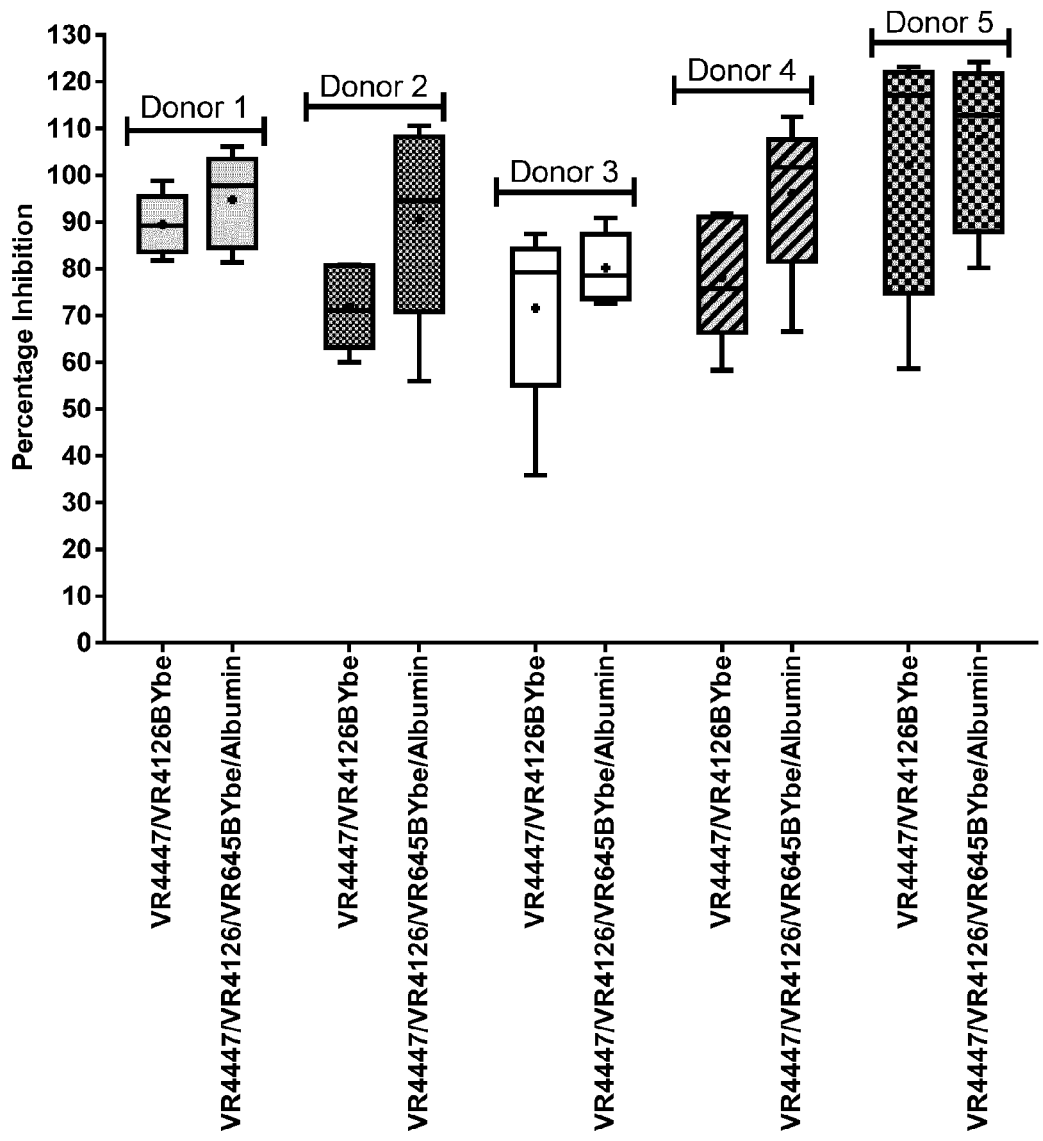
Figure 43:
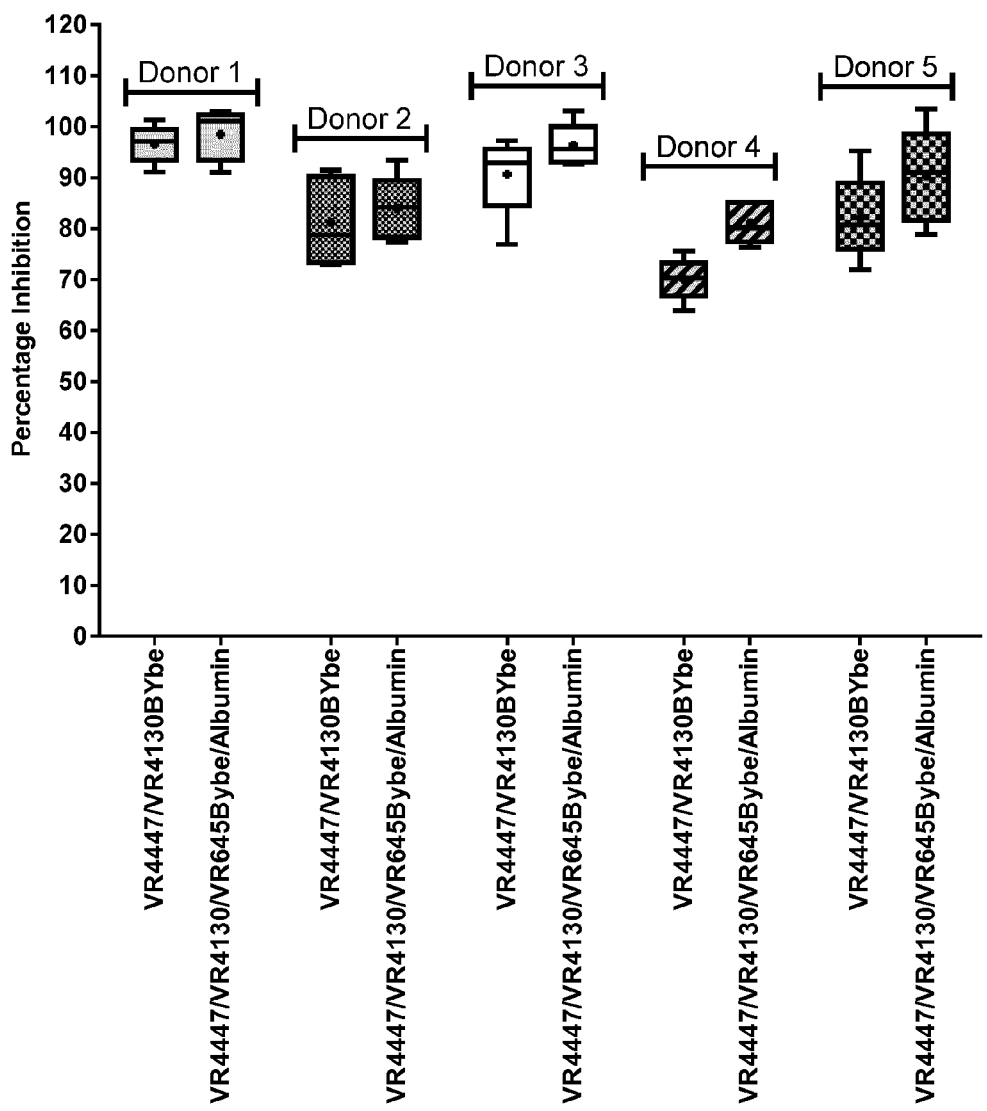
Figure 44:
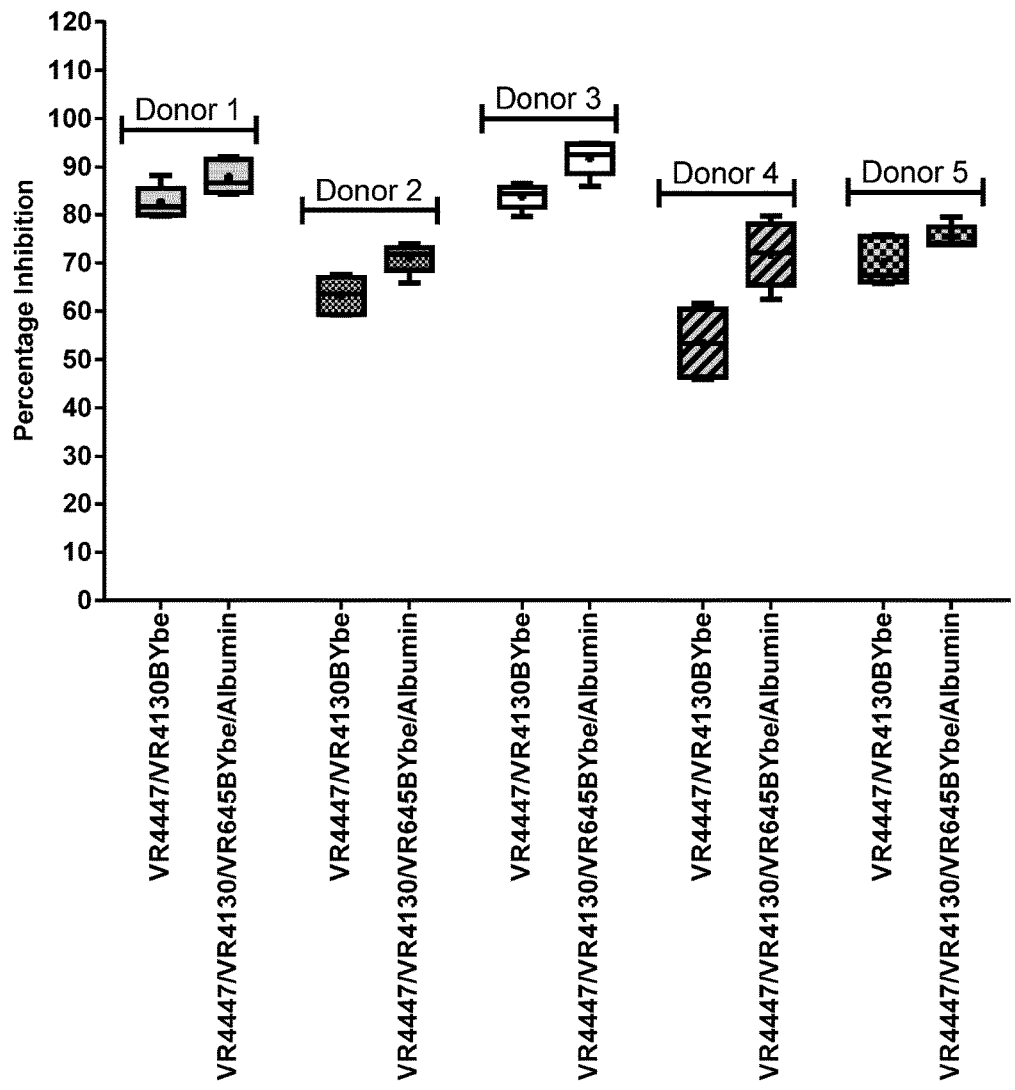
Figure 45:
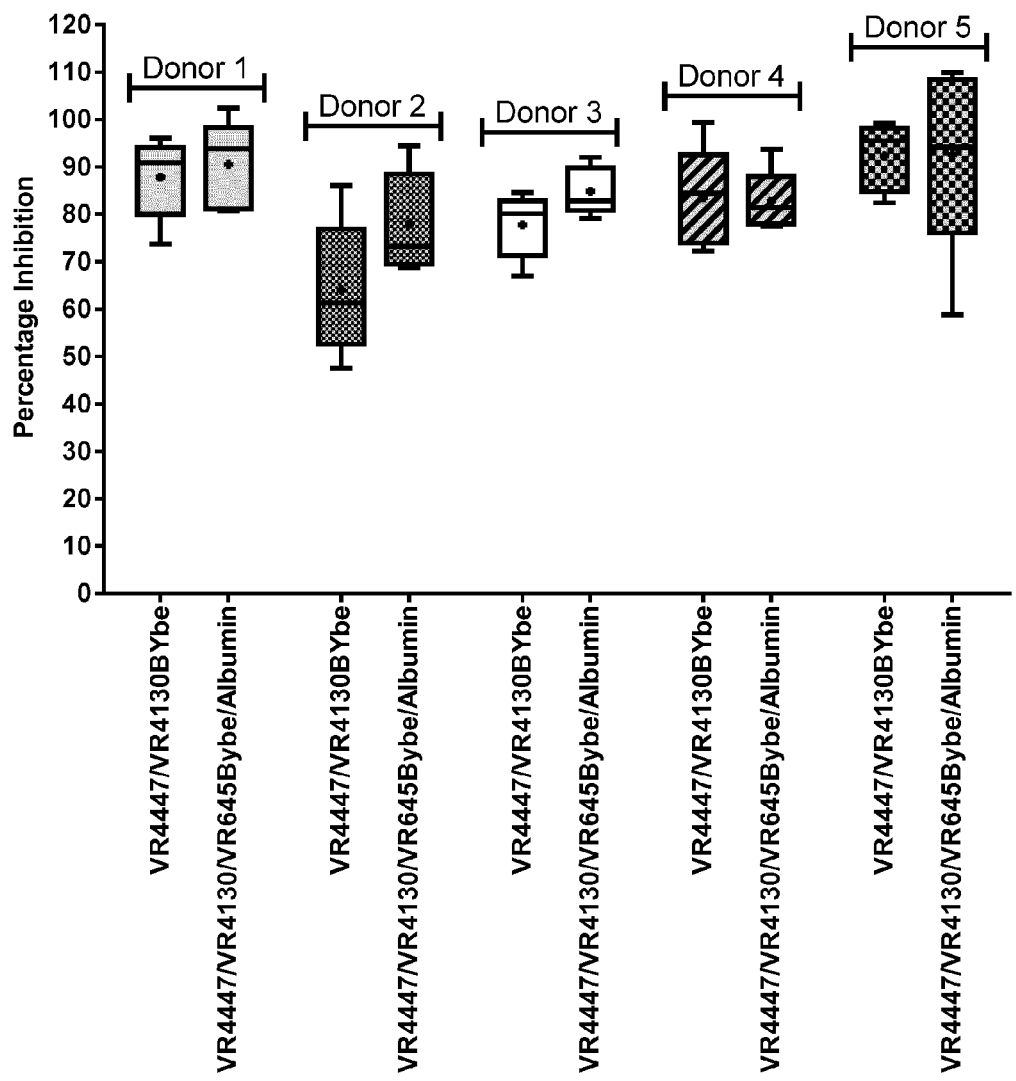

FIG. 39 shows data for the percentage inhibition of anti-IgM induced CD86 expression on B-cells, by antigen 3 and antigen 2 specific Fab-Kd-Fab or BYbe FIG. 40 shows the inhibition of CD27 expression on B cells by VR4447NR4126 BYbe and VR4447/VR4126/VR645 BYbe/Albumin FIG. 41 shows the inhibition of CD71 expression on B cells by VR4447NR4126 BYbe and VR4447/VR4126/VR645 BYbe/Albumin FIG. 42 shows the inhibition of CD86 expression on B cells by VR4447NR4126 BYbe and VR4447/VR4126/VR645 BYbe/Albumin FIG. 43 shows the inhibition of CD27 expression on B cells by VR4447NR4130 BYbe and VR4447/VR4130/VR645 BYbe/Albumin FIG. 44 shows the inhibition of CD71 expression on B cells by VR4447NR4130 BYbe and VR4447/VR4130/VR645 BYbe/Albumin FIG. 45 shows the inhibition of CD86 expression on B cells by VR4447NR4130 BYbe and VR4447/VR4130/VR645 BYbe/Albumin

DETAILED DESCRIPTION

"Bispecific protein complex" as used herein refers to a molecule comprising two proteins (A and B referred to herein as bispecific components also referred to herein as the first protein component and second protein component, respectively of the bispecific) which are retained together by a heterodimeric-tether. In one embodiment one or both of the proteins have a binding domain, for example one or both of the proteins are antibodies or fragments thereof (in particular a Fab or Fab' fragment, such complexes are also referred to as Fab-Kd-Fab).

"Fusion proteins" as employed herein comprise a protein component A or B fused to a binding partner X or Y (as appropriate). In one embodiment the fusion protein is a translational protein expressed by recombinant techniques from a genetic construct, for example expressed in a host from a DNA construct. In the context of the present disclosure one of the key characteristics of a fusion protein is that it can be expressed as a "single protein/unit" from a cell (of course in the case of fusion proteins comprising a Fab/Fab' fragment there will be two chains but this will be considered a single protein for the purpose of the present specification with one chain, typically the heavy chain fused at its C-terminus to X or Y as appropriate, optionally via a linker as described herein below).

The function of the heterodimeric tether X:Y is to retain the proteins A and B in proximity to each other so that synergistic function of A and B can be effected or identified, for example employing the method described herein.

"heterodimeric-tether" as used herein refers to a tether comprising two different binding partners X and Y which form an interaction: (such as a binding) between each other which has an overall affinity that is sufficient to retain the two binding partners together. In one embodiment X and/or Y are unsuitable for forming homodimers.

Heterodimerically-tethered and heterodimeric-tether are used interchangeably herein.

In one embodiment "unsuitable for forming homodimers" as employed herein refers to formation of the heterodimers of X-Y are more preferable, for example more stable, such as thermodynamically stable, once formed than homodimers. In one embodiment the binding interaction between X and Y is monovalent.

In one embodiment the X-Y interaction is more favourable than the X-X or Y-Y interaction. This reduces the formation of homodimers X-X or Y-Y when the fusion proteins A-X and B—Y are mixed. Typically greater than 75% heterodimer is formed following 1:1 molar ratio mixing.

If desired, a purification step (in particular a one-step purification), such as column chromatography may be employed, for example to purify the fusion protein units and/or bispecific protein complexes according to the present disclosure.

In one embodiment a purification step is provided after expression of the or each fusion protein, although typically aggregate levels are low. Thus in one embodiment prior to in vitro mixing, the fusion protein(s) is/are provided in substantially pure form. Substantially pure form as employed herein refers to wherein the fusion protein is 90, 91, 92, 93, 94, 95, 96, 97, 98, 99 or 100% monomer.

In one embodiment no purification of the fusion protein or proteins is performed.

In one embodiment each fusion protein unit is expressed in a different expression experiment/run.

In one embodiment no purification of the fusion protein or proteins is performed before mixing to generate a bispecific protein complex. In one embodiment no purification of the fusion protein or proteins is performed before and/or after mixing.

In one embodiment no purification is required after the bispecific protein complex formation. In one embodiment after mixing, and generally without further purification, at least 50% of the composition is the desired bispecific protein complex, for example at least 60, 65, 70, 75, 80% of the composition is the required bispecific protein complex.

In one embodiment the ratio of fusion proteins employed in the in vitro mixing step of the present method is A-X to B-Y 0.8:1 to 3:1, such as 1.5:1 or 2:1.

In one embodiment the ratio of fusion proteins employed in the in vitro mixing step of the present method is B-Y to A-X 0.8:1 to 3:1, such as 1.5:1 or 2:1, in a particular a molar ratio.

In one embodiment the ratio of A-X to B-Y employed in the in vitro mixing step is 1:1, in particular a 1:1 molar ratio.

The present disclosure also extends to a method of preparing a bispecific complex according to the present disclosure comprising admixing a fusion protein A-X and B-Y, for example in a 1:1 molar ratio.

In one embodiment the mixing occurs in vitro.

In one embodiment mixing occurs in a cell, for example a host cell.

In one embodiment, the mixing occurs in vivo, i.e. the fusion proteins A-X and B-Y interact with each other within a subject's body to form the heterodimeric-tether and in consequence, the bispecific protein complex.

In one embodiment, X and Y are completely specific for each other and do not bind to any other peptides/proteins in a cell or within a subject's body. This can be achieved for example by ensuring that X and Y are not naturally present in the target cell or in the target subject's body. This can be achieved, for example by selecting X or Y to be from a species or entity which is different to the subject (e.g. a yeast protein) and ensuring the other variable is specific to it.

Advantageously, this prevents the binding of the fusion proteins A-X and/or B-Y to an undesired target, thereby generating unwanted off-target effects.

In one embodiment one (or at least one) of the binding partners is incapable of forming a homodimer, for example an amino acid sequence of the binding partner is mutated to eliminate or minimise the formation of homodimers.

In one embodiment both of the binding partners are incapable of forming a homodimer, for example an amino acid sequence of the peptide binding partner is mutated to eliminate or minimise the formation of homodimers and a VHH specific thereto is employed.

Incapable of forming homodimers or aggregates as employed herein, refers to a low or zero propensity to form homodimers or aggregate. Low as employed herein refers to 5% or less, such as 4, 3, 2, 1, 0.5% or less aggregate, for example after mixing or expression or purification.

Small amounts of aggregate in the fusion proteins or residual in the heterodimerically-tethered bispecific protein complex generally has minimal effect on the screening method of the present disclosure. Therefore, in one embodiment no purification of fusion protein(s) and/or bispecific protein complex(es) is/are employed in the method, in particular after the mixing step.

In one embodiment: is a binding interaction based on attractive forces, for example Van der Waals forces, such as hydrogen bonding and electrostatic interactions, in particular, based on antibody specificity for an antigen (such as a peptide).

In one embodiment: is a covalent bond formed from a specific chemical interaction, such as click chemistry. In one embodiment: is not a covalent bond. In one embodiment conjugation/coupling chemistry is not employed to prepare the bispecific protein complexes of the present disclosure.

"Form the complex" as employed herein refers to an interaction, including a binding interaction or a chemical reaction, which is sufficiently specific and strong when the fusion protein components A-X and B—Y are brought into contact under appropriate conditions that the complex is assembled and the fusion proteins are retained together.

"Retained together" as employed herein refers to the holding of the components (the fusion proteins) in the proximity of each other, such that after X:Y binding the complex can be handled as if it were one molecule, and in many instances behaves and acts like a single molecule. In one embodiment the retention renders the complex suitable for use in the method disclosed herein, i.e. suitable for use in at least one functional screen.

Specificity as employed herein refers to where, for example the partners in the interaction e.g. X:Y or A and antigen or B and antigen only recognise each other or have significantly higher affinity for each other in comparison to non-partners, for example at least 2, 3, 4, 5, 6, 7, 8, 9, 10 times higher affinity, than for example a background level of binding to an unrelated non partner protein.

Specificity in relation to X and Y as employed herein refers to where the binding partners X and Y in the interaction only recognise each other or have significantly higher affinity for each other in comparison to non-partners, for example at least 2, 3, 4, 5, 6, 7, 8, 9, 10 times higher affinity.

In one embodiment the binding interaction is reversible. In one embodiment the binding interaction is essentially irreversible.

Essentially irreversible as employed herein refers to a slow off rate (dissociation constant) of the antibody or binding fragment.

In one embodiment, the binding interaction between X and Y has a low dissociation constant. Examples of a low dissociation constant include $1\text{-}9\times10^{-2}\text{s}^{-1}$ or less, for example $1\text{-}9\times10^{-3}\text{s}^{-1}$, $1\text{-}9\times10^{-4}\text{s}^{-1}$, $1\text{-}9\times10^{-5}\text{s}^{-1}$, $1\text{-}9\times10^{-6}\text{s}^{-1}$ or $1\text{-}9\times10^{-7}\text{s}^{-1}$. Particularly suitable dissociation constants include $2\times10^{-4}\text{s}^{-1}$ or less, for example $1\times10^{-5}\text{s}^{-1}$, $1\times10^{-6}\text{s}^{-1}$ or $1\times10^{-7}\text{s}^{-1}$.

Whilst not wishing to be bound by theory it is thought that the low dissociation constant (also referred to as off rate) allows the molecules to be sufficiently stable to render the bispecific protein complex useful, in particular in functional screening assays.

In one embodiment, the affinity of X and Y for each other is 5 nM or stronger, for example 4 nM, 3 nM, 2 nM, 1 nM or stronger.

In one embodiment, the affinity of X and Y for each other is 900 pM or stronger, such as 800, 700, 600, 500, 400, 300, 200, 100 or 50 pM or stronger.

In another embodiment, the affinity of X and Y for each other is 10 pM or stronger, for example 9, 8, 7, 6 or 5 pM.

Affinity is a value calculated from the on and off rate of the entity. The term "affinity" as used herein refers to the strength of the sum total of non-covalent interactions between a single binding site of a molecule (e.g. an antibody) and its binding partner (e.g. a peptide). The affinity of a molecule for its binding partner can generally be represented by the dissociation constant (KD). Affinity can be measured by common methods known in the art, including those described herein, such as surface plasmon resonance methods, in particular BIAcore.

However, the ability to hold the complex together is not just about affinity. Whilst not wishing to be bound by theory, we hypothesise that in fact there are three significant components: the on-rate, off-rate and the affinity. The calculation for affinity is based on on-rate and off-rate. So if the on-rate is low and the off-rate is fast, then the affinity will be low and that will not be sufficient to hold the bispecific protein complex together. However, a slow on-rate could be compensated for by a slow off-rate giving an overall suitable affinity. In some embodiments a high on-rate may be sufficient to hold the complex together.

If the binding partners (X and Y) employed in the complex have a slow on-rate then additional time may be required after mixing the components to allow the complex to form.

If the affinity between the binding partners is sufficiently high, it may be possible for the bispecific protein complex to perform its desired biological function even if the affinity of the proteins (A and B) of the bispecific protein complex only bind weakly to their targets. Conversely, if the proteins (A and B) are able to bind strongly to their targets, it may be possible to achieve the same biological function even if the affinity of the binding partners (X and Y) for each other is lower. In other words, a 'trinity' relationship exists such that a higher affinity between the binding partners can compensate for a lower affinity for the targets and vice versa.

In one embodiment the affinity of protein A for its ligand or antigen is about 100 nM or stronger such as about 50 nM, 20 nM, 10 nM, 1 nM, 500 pM, 250 pM, 200 pM, 100 pM or stronger, in particular a binding affinity of 50 pM or stronger.

In one embodiment the affinity of protein B for its ligand or antigen is about 100 nM or stronger such as about 50 nM, 20 nM, 10 nM, 1 nM, 500 pM, 250 pM, 200 pM, 100 pM or stronger, in particular a binding affinity of 50 pM or stronger.

In one embodiment an interaction between a constant domain in a heavy chain, such as CH1 and a constant domain in a light chain, such as CKappa contribute to the formation and/or stability of a bispecific complex according to the present disclosure. Thus employing Fab or Fab' fragments in the bispecific complexes of the present disclosure is beneficial.

In one embodiment the bispecific complex of the present disclosure does not comprise a component with an effector function, for example the complex does not comprise a constant domain other than a CH1 and CKappa or CLambda, in particular does not comprise constant domains independently selected from the group comprising CH2, CH3, CH4 and combinations thereof. In one embodiment the bispecific complex of the present disclosure lacks an Fc region.

In one embodiment the method herein is employed to screen a naïve phage library by preparing fusion proteins of the disclosure from the library.

The bispecific protein complexes of the present invention may be used in any suitable application, including functional screening. This novel format is particularly useful in multiplex functional screening to identify protein targets based on function, and optimal epitopes on those target proteins, which could be targeted by bispecific therapies. Furthermore where proteins A and B are antibodies or binding fragments thereof the bispecific protein complexes may also be used for multiplex functional screening to identify optimal variable region pairs for use in bispecific antibody therapeutics.

"Multiplex" as employed herein is a population of entities for testing comprising:
- at least two component fusion proteins (A-X and Y-B) combined to generate at least one heterodimerically-tethered bispecific protein complex and at least one relevant biological comparator in the same or a different format, or
- at least two heterodimerically-tethered bispecific protein complexes with optionally at least one relevant biological comparator in the same or a different format.

Clearly to be useful, the different format employed as the comparator must be suitable for testing in a functional in vitro assay employed in the disclosure. In one example the comparator in the multiplex is a monovalent mixture of A-X and B-X or a bivalent monospecific complex of A-X-Y-A.

In one embodiment the multiplex comprises 1 to hundreds of thousands of heterodimerically-tethered bispecific protein complexes, for example 2 to 500,000 of said complexes, such as 2 to 100,000 or 2 to 10,000, in particular generated from mixing in a grid 2 to 100s of first and second fusion proteins (A-X and B-Y). In one embodiment the multiplex comprises for example 2 to 1,000, such as 2 to 900, 2 to 800, 2 to 700, 2 to 600, 2 to 500, 2 to 400, 2 to 300, 2 to 200, 2 to 100, 2 to 90, 3 to 80, 4 to 70, 5 to 60, 6 to 50, 7 to 40, 8 to 30, 9 to 25, 10 to 20 or 15 bispecific protein complexes. See FIG. 3 for an example of such a grid.

In one embodiment the number of heterodimerically-tethered bispecific proteins in this multiplex is $n^2$ where n is 1, 2, 3, 4, 5, 6, 7, 8, 9, 10, 11, 12, 13, 14, 15 or more.

The multiplex may be in the form of an array, for example a microtitre plate, wherein each well of the microplate may contain a different bispecific protein complex. The bispecific protein complexes may be tethered to a solid substrate surface, for example attached to a bead, or they may be suspended in a liquid (e.g. a solution or media) form, for example within a well or within a droplet.

In one embodiment every 'A' in the multiplex is a different protein, preferably an antibody or binding fragment thereof that binds to a target antigen and every 'B' is a different protein preferably an antibody or binding fragment thereof that binds to a target antigen.

In one embodiment the multiplex is provided in a grid as discussed below, for example an 8×8, 16×16 or 16×20, which equates to 64, 256 or 320 samples respectively.

"Grid" as employed herein refers to a two dimensional plot or array where one variable, such a protein A (in A-X) is varied along one axis, such as the X-axis (horizontal axis) and another variable such as protein B (in B-Y) is varied along the other axis, such as the Y axis (vertical axis). This arrangement assists in systematically evaluating the various combinations (permutations) of the variables.

In one embodiment the multiplex is provided on 96 well plates and the samples analysed may be multiples thereof i.e. 96, 192, 384 etc.

Figure 1:
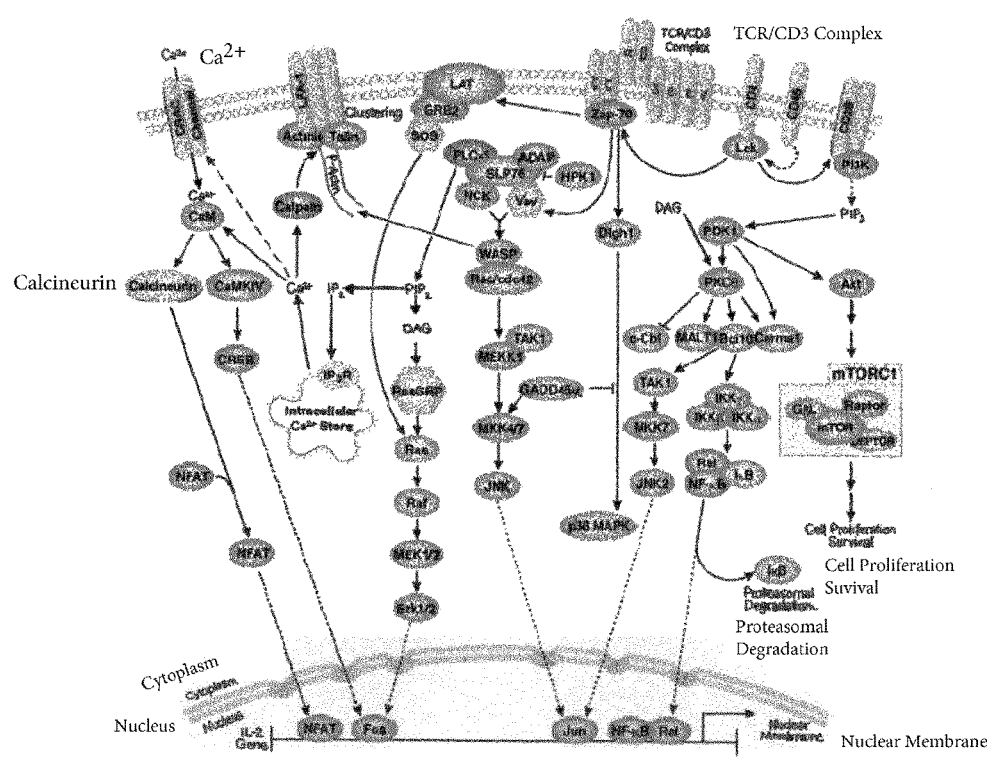
FIG. 1 is a schematic diagram showing the main cell signalling pathways involved in the activation of T cells.
Figures 2, 3:
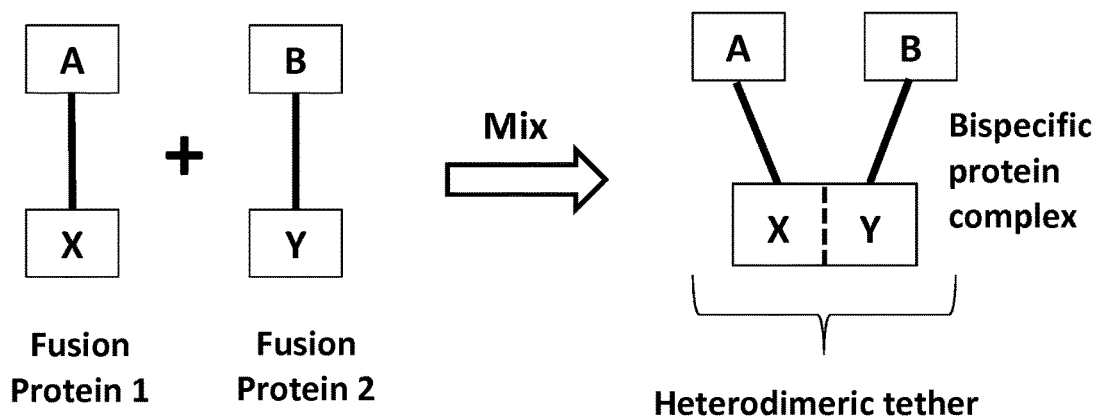
FIG. 2 is a schematic diagram showing the structure and assembly of a bispecific protein complex of the present disclosure.
FIG. 3 is a table showing an example 4×4 grid for functional screening using the bispecific antibody of the present invention. Using this grid, 16 different bispecific protein complexes can be assembled and efficiently screened for synergistic function.

Advantageously, a grid arrangement is particularly advantageous for efficiently screening the biological function of bispecific protein complexes according to the present disclosure. FIG. 3 shows an example of such a grid, whereby 4 first fusion proteins can be readily combined with 4 second fusion proteins to produce 16 bispecific protein complexes.

Other variations of a screening grid will be apparent to the skilled addressee, for example the first protein (A) in the first fusion protein (A-X) may be kept constant whilst the second protein (B) in the second fusion protein (B-X) is varied. This may be useful for quickly screening a large number of different second proteins for synergistic function with the pre-selected first protein.

In another embodiment, protein A is varied along one axis by changing the antibody variable regions of protein A such that each antibody variant is specific for the same antigen but has a different combination of variable regions. Protein B may either be kept constant or may also be varied in the same fashion or varied such that the antigen specificity changes (across or down the grid) for the B proteins.

Advantageously, such a screening grid may potentially allow for the detection of small differences in synergistic function when the bispecific protein complexes are specific for the same antigens but with different combinations of variable regions.

In one embodiment, a "common" first fusion protein (A-X) according to the present disclosure may be present within each well. A range of different second fusion proteins (B-Y) according to the present disclosure may then be dispensed into each well. Subsequently, the specific binding interaction of the two binding partners (X and Y) physically brings the two fusion proteins together to form the bispecific protein complexes. This results in a multiplex comprising bispecific protein complexes which all bind to a common first target antigen (bound by A) but are also capable of binding to a second target antigen (bound by B) which may be different for each bispecific protein complex.

In one embodiment the B-Y fusion proteins comprise different variable regions to the same target antigen to allow optimisation of the variable regions and/or epitopes of the given target antigen bound by B when combined with the variable regions in A-X.

"Common" first fusion protein as employed herein refers to fusions proteins wherein the A or B component thereof, bind the same proteins or epitope, in particular where the A or B component have complete identity in the common fusion protein i.e. the common first fusion protein always comprises the same variable region sequence.

The skilled person is also aware of different variations of the above, such that the desired specificities of the bispecific protein complexes at each position in the multiplex can be readily controlled. This allows for the efficient screening of different combinations of bispecific protein complexes when such multiplexes are used in functional assays. In one embodiment factorial design is employed to define the variables employed in the grid.

In one embodiment the method of the present disclosure is conducive to high-throughput analysis.

In one embodiment, multiple bispecific protein complexes are tested in parallel or essentially simultaneously.

Simultaneously as employed herein refers to the where the samples/molecules/complexes are analysed in the same analysis, for example in the same "run". This may be advantageous as generally the reagents employed for a given sample run will be the same batch, concentration, cell source etc and therefore have the same properties. Furthermore the environmental conditions under which the analysis is performed, such as temperature and humidity are likely to be similar.

In one embodiment simultaneously refers to concomitant analysis where the signal output is analysed by an instrument at essentially the same time. This signal may require deconvolution to interpret the results obtained.

Advantageously, testing multiple bispecific protein complexes allows for more efficient screening of a large number of bispecific protein complexes and the identification of new and interesting relationships.

In one embodiment, the multiple bispecific protein complexes are tested by using a multiplex as defined above and subjecting the same to one or more functional assays. Accordingly the present invention provides a method for detecting synergistic biological function in a heterodimerically-tethered bispecific protein complex of formula A-X:Y-B
wherein X:Y is a heterodimeric-tether
: is a binding interaction between X and Y,
A and B are protein components of the bispecific in the form of fusion proteins with X and Y respectively, said method comprising the steps of:
  (i) testing for activity in a functional assay for part or all of a multiplex comprising at least one heterodimerically-tethered bispecific protein complex; and
  (ii) analysing the readout(s) from the functional assay to identify or detect synergistic biological function in the heterodimerically-tethered bispecific protein complex; and
wherein Y is an antigen and X is an antibody or binding fragment thereof specific to Y or X is an antigen and Y is an antibody or binding fragment thereof specific to X.

The term "biological function" as used herein refers to an activity that is natural to or the purpose of, the biological entity being tested, for example a natural activity of a cell, protein or similar. Ideally the presence of the biological function can be tested using an in vitro functional assay, including assays employing mammalian cells, such as living cells, such as B or T cells, or tissue ex vivo. Natural function as employed herein also includes aberrant function, such as functions associated with diseases, such as cancers.

A relevant "biological comparator" as employed herein refers to a suitable entity for assessing activity, in the same assay as that employed for the bispecific protein complex, to establish if there is any change or novel activity or function. Suitable comparators for A-X:Y-B may include a purified protein (including recombinant proteins) in a natural form or presented in the same format as the bispecific e.g. where A and B are the same entity, such as A-X:Y-A or B-X:Y-B i.e. a bivalent monospecific complex. Alternatively the fusion protein A-X or B-Y in an uncomplexed form may be employed as a comparator alone or as an uncomplexed mixture such as A-X and B-X together or A-Y and B-Y together. Alternatively, multiple comparators of different formats (in particular as described herein) may be employed. The person skilled in the art is able to identify and include a suitable control/comparator based on common general knowledge or information that is found in the literature.

The term "synergistic function" or "synergistic biological function" as used herein refers to a biological activity or level of biological activity or an effect on a biological function or activity that:
  is not observed with individual fusion protein components until a bispecific is employed (and may include activity observed with a combination of antibodies to the said antigens, which are not in an bispecific format, but in particular refers to activity only observed when the two binding domains are linked in a bispecific format) or
  higher or lower activity in comparison to the activity observed when the first and second proteins of a bispecific protein complex of the present disclosure are employed individually, for example activity which is only observed in a bispecific form.

Therefore, "synergistic" includes novel biological function or novel activity. Synergistic function as employed herein does not generally include simple targeting i.e. based only on binding but will generally involve some inhibition, activation, signalling or similar after binding.

Novel biological function or novel activity as employed herein refers to a biological function or activity which is not apparent or is absent until the two or more synergistic entities (protein A and protein B) are brought together (as a bispecific or otherwise) or a previously unidentified function.

Higher as employed herein refers to an increase in activity including an increase from zero e.g. some activity in the bispecific where the individual uncomplexed bispecific component or components has/have no activity in the relevant functional assay, also referred to herein as new activity or novel biological function. Higher as employed herein also includes a greater than additive function in the bispecific in a relevant functional assay in comparison to the individual uncomplexed bispecific components (tested alone or in combination with being linked), for example 10, 20, 30, 40, 50, 60, 70, 80, 90, 100, 200, 300% or more increase in a relevant activity.

In one embodiment the uncomplexed proteins together have the same activity as the bispecific and this activity or function was previously unknown. This is also a novel synergistic function in the context of the present specification.

In one embodiment the synergistic function is a higher function.

In one embodiment the synergistic function is a lower function.

Lower function as employed herein refers to where the bispecific in the relevant functional assay has less or no activity in comparison to the individual uncomplexed bispecific component (s) which has/have activity in the relevant functional assay, also referred to herein as new activity or novel biological function (such as a natural protein i.e. a recombinant isolated protein which is not in a fusion protein nor part of any other complex other than one in which occurs in vivo-including an active domain or fragment of said protein) analysed as an individual protein or analysed as a mixture of proteins under the same conditions, for example 10, 20, 30, 40, 50, 60, 70, 80, 90, 100, 200, 300% or more decrease in a relevant activity. Greater than 100% decrease in activity refers to a gain in positive activity in a different direction, for example where an entity is an agonist decrease in activity over 100% may render the entity an antagonist and vice versa.

In one embodiment the activity of the bispecific complex is lower than the sum of the known function of protein A and protein B.

In some embodiments the bispecific protein complexes of the present disclosure have simply additive biological function. Additive biological function as employed herein refers to function, which is the same as the sum of each of the components A and B individually, when tested under the same conditions. An additive function may be a novel function if the activity or function was previously unknown or unidentified.

Screening is performed using any suitable assay known in the art, depending on the desired function to be identified.

In one embodiment, the functional assay employed in a method of the present disclosure is an in vitro or ex. vivo assay.

A "functional assay," as used herein, is an assay that can be used to determine one or more desired properties or activities of the bispecific protein complexes, antibody complexes or the mixture of antibodies subject to the assay conditions. Suitable functional assays may be binding assays, apoptosis assays, antibody-dependent cellular cytotoxicity (ADCC) assays, complement-dependent cytotoxicity (CDC) assays, inhibition of cell growth or proliferation (cytostatic effect) assays, cell-killing (cytotoxic effect) assays, cell-signalling assays, cytokine production assays, antibody production and isotype switching, cellular differentiation assays, colony forming assays, chemotaxis assays, cell adhesion assays, cell migration assays, cell cycle assays, metabolic assays (whole cell and organelle function), assays for measuring inhibition of binding of pathogen to target cell, assays to measure the secretion of vascular endothelial growth factor (VEGF) or other secreted molecules, assays for bacteriostasis, bactericidal activity, neutralization of viruses, assays to measure the attraction of components of the immune system to the site where antibodies are bound, including in situ hybridization methods, labeling methods, and the like.

In one embodiment in vivo assays, such as animal models, including mouse tumor models, models of auto-immune disease, virus-infected or bacteria-infected rodent or primate models, and the like, may be employed.

The skilled person is well able to select a suitable functional assay based on the target/proteins being investigated. However, the complexes may be subject to a panel of "standard" assays without preselecting assays thought to be relevant in an attempt identify new functionality.

In the context of bispecific antibody complexes, the efficacy of bispecific antibody complexes according to the present disclosure can be compared to individual antibodies or mixtures of antibodies (or fragments) in such models by methods generally known to one of ordinary skill in the art.

For example, the bispecific antibody complexes may be tested for the ability to inhibit proliferation, affect viability or metabolic activity of cells (for example with a stain such as allamar blue or by monitoring luminescence due to luciferase expressed by the cells), or cause apoptosis of cancer cells, which are biological functions that include properties other than binding to an antigen.

By choosing functional assays closely related to a particular disease of interest, the methods of the disclosure make it possible to identify potentially therapeutic antibodies that bind to known or unknown target molecules. It is thus possible to identify new target molecules and/or to directly identify potentially therapeutic antibodies using the methods of the disclosure. Advantageously, the present method is not limited to any particular assay(s) and provides the user with complete flexibility to select the most appropriate functional assay depending on the requirements.

When screening the bispecific antibody complexes for desired biological function, various strategies may be employed. For example, medium containing the antibodies can be directly screened for the biological activity. Alternatively, the antibodies can be bound to beads coated or to microtiter plates prior to screening for biological activity. Alternatively a fusion protein maybe purified via a His tag in a nickel capture purification step. Such strategies may increase local concentrations of the antibodies leading to clearer results from the functional assays.

The functional assays may be repeated a number of times as necessary with or without different samples of a particular bispecific antibody complex to enhance the reliability of the results. Various statistical tests known to the skilled person can be employed to identify statistically significant results and thus identify bispecific antibody complexes with biological functions.

When establishing a functional assay for screening the skilled person can set a suitable threshold over which an identified activity is deemed a chit'. Where more than one functional assay is used the threshold for each assay may be set at a suitable level to establish a manageable hit rate. In one example the hit rate may be 3-5%. In one example the criteria set when searching for pairs of antigens that inhibit B cell function may be at least 30% inhibition of at least two phospho-readouts in a B cell activation assay.

In the bispecific protein complexes of the present invention the following protein and peptide components may be used.

In one embodiment, at least one of the first binding partner, X, and the second binding partner, Y, of the binding pair are independently selected from a peptide and a protein; for example the first binding partner or second binding partner is a peptide.

Suitable peptides include the group comprising GCN4, Fos/Jun (human and murine Fos have a Uniprot number P01100 and P01101 respectively and human and murine jun have a Uniprot number 05412 and 05627 respectively), HA-tag which correspond to amino acids 98 to 106 of human influenza hemagglutinin, polyhistidine (His), c-myc and FLAG. Other peptides are also contemplated as suitable for use in the present disclosure and particularly suitable peptides are affinity tags for protein purification because such peptides have a tendency to bind with high affinity to their respective binding partners.

In one embodiment the peptide is not E5B9.

The term "peptide" as used herein refers to a short polymer of amino acids linked by peptide bonds, wherein the peptide contains in the range of 2 to 100 amino acids, for example 5 to 99, such as 6 to 98, 7 to 97, 8 to 96 or 5 to 25. In one embodiment a peptide employed in the present disclosure is an amino acid sequence of 50 amino acid residues or less, for example 40, 30, 20, 10 or less. The peptides used in the present disclosure are of a sufficient length to be fit for purpose, for example if the peptide is a linker, it needs to be suitably long to allow the fragment which it links to perform its biological function; alternatively if the peptide is a binding partner, it must be capable of binding specifically to another entity such as an antibody.

In one embodiment, the other binding partner of the binding pair (the alternative first or second binding partner) is a protein.

Protein as employed herein refers to an amino acid sequence of 100 amino acids or more. In one embodiment a "protein" as employed herein refers to an amino acid sequence with a secondary or tertiary structure.

Polypeptide and protein are employed interchangeably herein. However, polypeptide will generally be a protein with a simple structure, for example little secondary and/or tertiary structure.

In one embodiment the distinction between a peptide and a protein is based on the presence or absence of secondary structure and/or tertiary structure, where a peptide has no secondary structure and amino acids with secondary structure and/or tertiary structure are considered a protein.

In one embodiment, the protein is an antibody or an antibody fragment.

The term "antibody" as used herein refers to an immunoglobulin molecule capable of specific binding to a target antigen, such as a carbohydrate, polynucleotide, lipid, polypeptide, peptide etc., via at least one antigen recognition site (also referred to as a binding site herein), located in the variable region of the immunoglobulin molecule.

As used herein "antibody molecule" includes antibodies and binding fragments thereof.

"Antibody fragments" as employed herein refer to antibody binding fragments including but not limited to Fab, modified Fab, Fab', modified Fab', F(ab')2, Fv, single domain antibodies, scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216:165-181). Other antibody fragments for use in the present disclosure include the Fab and Fab' fragments described in International patent applications WO05/003169, WO05/003170 and WO05/003171. Multivalent antibodies may comprise multiple specificities e.g. bispecific or may be monospecific (see for example WO92/22853, WO05/113605, WO2009/040562 and WO2010/035012).

A "binding fragment" as employed herein refers to a fragment capable of binding a target peptide or antigen with sufficient affinity to characterise the fragment as specific for the peptide or antigen.

The term "Fab fragment" as used herein refers to an antibody fragment comprising a light chain fragment comprising a VL (variable light) domain and a constant domain of a light chain (CL), and a VH (variable heavy) domain and a first constant domain (CH1) of a heavy chain. In one example the heavy chain sequences of the Fab fragment "terminates" at the interchain cysteine of CH1. In one embodiment the Fab fragment employed in a fusion protein of the present disclosure, such as A-X and/or B—Y is monovalent.

A Fab' fragment as employed herein refers to a Fab fragment further comprising all or part of a hinge region. In one embodiment the Fab' fragment employed in a fusion protein of the present disclosure, such as A-X and/or B—Y is monovalent.

The term "single-chain Fv" or abbreviated as "scFv", as used herein refers to an antibody fragment that comprises VH and VL antibody domains linked (for example by a peptide linker) to form a single polypeptide chain. The constant regions of the heavy and light chain are omitted in this format. Single-chain Fv as employed herein includes disulfide stabilised versions thereof wherein in addition to the peptide linker a disulfide bond is present between the variable regions.

Disulfide stabilised scFv may eliminate the propensity of some variable regions to dynamically breath, which relates to variable regions separating and coming together again.

The term "single domain antibody" as used herein refers to an antibody fragment consisting of a single monomeric variable antibody domain. Examples of single domain antibodies include VH or VL or VHH.

In one embodiment the antibody binding fragment and/or the bispecific antibody complex does not comprise an Fc region. "Does not comprise an Fc region" as employed herein refers to the lower constant domains, such as CH2, CH3 and CH4 which are absent. However, constant domains such as CH1, CKappa/CLambda may be present.

In one embodiment, the antibody heavy chain comprises a CH1 domain and the antibody light chain comprises a CL domain, either kappa or lambda.

In one embodiment, the antibody heavy chain comprises a CH1 domain, a CH2 domain and a $CH_3$ domain and the antibody light chain comprises a CL domain, either kappa or lambda.

In one embodiment, the first protein, A, and/or second protein, B, of the bispecific protein complex is an antibody or antibody fragment. Such a bispecific protein complex may be referred to as a bispecific antibody complex.

"Bispecific antibody complex" as employed herein refers to a bispecific protein complex comprising at least two antibody binding sites wherein the component antibodies, fragments or both are complexed together by a heterodimeric-tether.

A bispecific antibody complex usually refers to a molecule comprising at least two antigen binding sites, wherein the binding sites have non-identical specificity.

In one embodiment, the two proteins (for example antibodies, fragments or a combination of an antibody and a fragment) target the same antigen, for example binding to two different epitopes on the same target antigen, also referred to herein as a biparatopic bispecific.

In another embodiment, the two proteins (for example antibodies, fragments or a combination of an antibody and a fragment) may have different antigen specificities, for example binding to two different target antigens.

In yet another embodiment, the two proteins are identical, i.e. binding to the same epitope on the same target antigen and the complex is therefore monospecific.

In one embodiment each antibody or fragment employed in the bispecific antibody complex of the disclosure comprises one binding site i.e. each binding site is monovalent for each target antigen.

The full length antibody or antibody fragment employed in the fusion proteins (A-X or B-Y) may be monospecific, monovalent, multivalent or bispecific.

Advantageously, the use of two bispecific antibody or antibody fragments allows the bispecific antibody complex of the present disclosure to potentially be specific for up to 4 different antigens (i.e. the complex may be tetraspecific). This allows avidity type effects to be investigated.

In one embodiment, the antibody or antibody fragment employed in the first fusion protein (A-X) is a monospecific antibody or antibody fragment, in particular a monovalent Fab, Fab', scFv, Fv, VHH or similar.

In one embodiment, the antibody or antibody fragment employed in the second fusion protein (B-Y) is a monospecific antibody or antibody fragment, in particular a monovalent Fab, Fab', scFv or similar.

"Monospecific" as employed herein refers to the ability to bind only one target antigen.

"Monovalent" as employed herein refers to the antibody or antibody fragment having a single binding site and therefore only binding the target antigen only once.

In one embodiment, the antibody or antibody fragment employed in the first fusion protein (A-X) is multivalent, that is has two or more binding domains.

In one embodiment, the antibody or antibody fragment employed in the second fusion protein (B-Y) is multivalent, that is has two or more binding domains.

In one embodiment, the antibody or antibody fragment employed in the first fusion protein (A-X) is monovalent and the antibody or antibody fragment employed in the second fusion protein (B-X) is monovalent.

In one embodiment, the antibody or antibody fragment employed in the first fusion protein (A-X) is monovalent and the antibody or antibody fragment employed in the second fusion protein (B-Y) is multivalent.

In one embodiment, the antibody or antibody fragment employed in the first fusion protein (A-X) is multivalent and the antibody or antibody fragment employed in the second fusion protein (B-Y) is monovalent.

In one embodiment, the antibody or antibody fragment employed in the first fusion protein (A-X) is multivalent and the antibody or antibody fragment employed in the second fusion protein (B-Y) is multivalent.

In one embodiment A-X or B—Y is not a fusion protein comprising two scFvs one specific to the antigen CD33 and one specific to the antigen CD3 or alternatively a bispecific complex format specific to these two antigens.

In one embodiment the A-X or B—Y is not a fusion protein comprising a scFv (or alternatively another antibody format) specific to CD3 linked to a peptide E5B9.

A "binding domain or site" as employed herein is the part of the antibody that contacts the antigen/epitope and participates in a binding interaction therewith. In one embodiment the binding domain contains at least one variable domain or a derivative thereof, for example a pair of variable domains or derivatives thereof, such as a cognate pair of variable domains or a derivative thereof.

In one embodiment the binding domain comprises 3 CDRs, in particular where the binding domain is a domain antibody such as a VH, VL or VHH. In one embodiment the binding domain comprises two variable domains and 6 CDRs and a framework and together these elements contribute to the specificity of the binding interaction of the antibody or binding fragment with the antigen/epitope.

A "cognate pair" as employed herein refers to a heavy and light chain pair isolated from a host as a pre-formed couple. This definition does not include variable domains isolated from a library, wherein the original pairings from a host is not retained. Cognate pairs may be advantageous because they are often affinity matured in the host and therefore may have high affinity for the antigen to which they are specific.

A "derivative of a naturally occurring domain" as employed herein is intended to refer to where one, two, three, four or five amino acids in a naturally occurring sequence have been replaced or deleted, for example to optimize the properties of the domain such as by eliminating undesirable properties but wherein the characterizing feature(s) of the domain is/are retained. Examples of modifications are those to remove glycosylation sites, GPI anchors, or solvent exposed lysines. These modifications can be achieved by replacing the relevant amino acid residues with a conservative amino acid substitution.

In one embodiment, the bispecific antibody complexes of the present disclosure or antibody/fragment components thereof are processed to provide improved affinity for a target antigen or antigens. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In one embodiment, the first antibody or antibody fragment (A) is specific to a first antigen and the second antibody or antibody fragment (B) is specific to a second antigen, wherein the first and second antigens are different. Advantageously, the bispecfic antibody complex may be specific for two different antigens. This presents the possibility of the antibody complex binding to two different antigens, each located on a different entity, thereby bringing the two entities into close physical proximity with each other.

Alternatively, the first antibody or antibody fragment (A) may be specific for a first epitope and the second antibody or antibody fragment (B) may be specific for a second epitope, wherein the first and second epitopes are both on the same antigen. This can greatly enhance the avidity of the bispecific antibody complex for the antigen due to the multiple interactions between the antigen and bispecific antibody complex.

In one embodiment, the first antibody (A) or second antibody (B) or both the first and second antibody of a bispecific antibody complex of the present disclosure may be an IgG, optionally with an inactive or active Fc region.

In one embodiment, the first (A) or second (B) antibody fragment is selected from the group consisting of: a fragment antigen binding (Fab), a Fab', a single chain variable fragment (scFv) and a single domain antibody (sdAb), such as a VHH.

In one embodiment, the first antibody/fragment (A), second antibody/fragment (B) or both the first and second antibody/fragment of the bispecific antibody complex of the present disclosure may be a Fab.

In one embodiment, the first antibody/fragment (A), second antibody/fragment (B) or both the first and second antibody/fragment of the bispecific antibody complex of the present disclosure may be a Fab'.

In one embodiment, the first antibody/fragment (A), second antibody/fragment (B) or both the first and second antibody/fragment of the bispecific antibody complex of the present disclosure may be a scFv.

In one embodiment, the first (A) or second (B) antibody/fragment or both the first and second antibody/fragment of the bispecific antibody complex of the present disclosure is/are a VHH.

For convenience bispecific protein complexes of the present disclosure are referred to herein as A-X:Y-B. However, this nomenclature is not intended to limit how the fusion protein A-X and B—Y are designed because our experiments indicate that binding partners X and Y can be reversed i.e. A-Y and B-X without adversely impacting on the method. Thus A and B and X and Y are nominal labels referred to for assisting the explanation of the present technology.

"Attached" as employed herein refers to connected or joined directly or indirectly via a linker, such as a peptide linker examples of which are discussed below. Directly connected includes fused together (for example a peptide bond) or conjugated chemically.

"Binding partner" as employed herein refers to one component part of a binding pair. In one embodiment, the affinity of the binding partners is high, 5 nM or stronger, such as 900, 800, 700, 600, 500, 400, 300 pM or stronger.

"Binding pair" as employed herein refers to two binding partners which specifically bind to each other. Examples of a binding pair include a peptide and an antibody or binding fragment specific thereto, or an enzyme and ligand, or an enzyme and an inhibitor of that enzyme.

In one embodiment, the first binding partner (X) is selected from the group comprising: a full length antibody, a Fab, a Fab', Fv, dsFv, a scFv and a sdAb, wherein examples of a sdAb include VH or VL or VHH.

When X is an antibody or binding fragment thereof then Y is a protein or peptide, in particular a peptide.

In one embodiment, the second partner (Y) is selected from the group comprising: a full length antibody, a Fab, a Fab', Fv, dsFv, a scFv and a sdAb, wherein examples of a sdAb include VH or VL or $V_HH$.

When Y is an antibody or binding fragment thereof then X is a protein or peptide, in particular a peptide.

In one embodiment, where A is an antibody or fragment thereof the first binding partner (X) is attached to the C-terminal of the heavy or light chain of the first antibody or antibody fragment, for example, the first binding partner (X) is attached to the C-terminal of the heavy chain of the first antibody or antibody fragment (A).

In another embodiment, where B is an antibody or fragment thereof the second binding partner (Y) is attached to the C-terminal of the heavy or light chain of the second antibody or antibody fragment, for example the second binding partner (Y) is attached to the C-terminal of the heavy chain of the second antibody or antibody fragment (B).

In one embodiment X is attached to the C-terminal of the heavy chain of the antibody or fragment (protein A) and Y is attached to the C-terminal of the heavy chain of the antibody or fragment (protein B).

In one embodiment X is attached via a linker (such as ASGGGG SEQ ID NO: 71 or ASGGGGSG SEQ ID NO: 72) or any other suitable linker known in the art or described herein below, to the C-terminal of the heavy chain of the antibody or fragment (protein A) and Y is attached via a linker (such as ASGGGG SEQ ID NO: 71 or ASGGGGSG SEQ ID NO: 72) to the C-terminal of the heavy chain of the antibody or fragment (protein B).

Examples of a suitable binding pair (X or Y) may include GCN4 (SEQ ID NO: 1 or lacking the HIS tag, amino acids 1-38 of SEQ ID NO: 1) or a variant thereof and 52SR4 (SEQ ID NO: 3 or lacking the HIS tag amino acids 1 to 243 of SEQ ID NO:3) or a variant thereof, which is a scFv specific for GCN4.

In a one embodiment, the first binding partner (nominally X) is GCN4 (for example as shown in SEQ ID NO: 1) or a fragment or variant thereof (for example without the His tag) and the second binding partner (nominally Y) is a scFv or VHH specific for GCN4 (for example as shown in SEQ ID NO: 3) or a variant thereof.

In one embodiment, the first binding partner (nominally X) is a sFv or VHH specific for GCN4 (for example as shown in SEQ ID NO: 3) or a variant thereof and the second binding partner (nominally Y) is GCN4 (for example as shown in SEQ ID NO: 1) or a fragment or variant thereof.

GCN4 variants include an amino acid sequence with at least 80%, 85%, 90%, 91%, 92%, 93%, 94% 95%, 96%, 97% or 98%, or 99% identity to SEQ ID NO: 1. GCN4 variants also include an amino acid having at least 80%, 85%, 90%, 91%, 92%, 93%, 94%, 95%, 96%, 97%, 98%, or 99% to a sequence encoded by a nucleotide sequence SEQ ID NO: 2, or a sequence encoded by a nucleotide sequence which hybridises to SEQ ID NO: 2 under stringent conditions.

A suitable scFv specific to GCN4 is 52SR4 (SEQ ID NO: 3) or a variant thereof. Variants of 52SR4 include an amino acid sequence with at least 80%, or 85%, or 90%, or 95%, or 98%, or 99% identity to SEQ ID NO: 3. 52SR4 variants also include an amino acid sequence having at least at least 80%, or 85%, or 90%, or 95%, or 98%, or 99% to a sequence encoded by a nucleotide sequence SEQ ID NO: 4, or a sequence encoded by a nucleotide sequence which hybridises to SEQ ID NO: 4 under stringent conditions.

The present inventors have found that the single chain antibody 52SR4 and peptide GCN4, are a binding pair suitable for use in the bispecific protein complexes of the present disclosure.

Alternatively, any suitable antibody/fragment and antigen (such as a peptide) may be employed as X and Y. Preferably such an X and Y pair result in greater than 75% heterodimer when A-X and Y—B are combined in a 1:1 molar ratio.

In one embodiment, the first binding partner (X) and the second binding partner (Y) are a protein.

In one embodiment, the first binding partner (X) is an enzyme or an active fragment thereof and the second binding partner (Y) is a ligand or vice versa.

In one embodiment, the first binding partner (X) is an enzyme or an active fragment thereof and the second binding partner (Y) is an inhibitor of that enzyme or vice versa.

"Active fragment" as employed herein refers to an amino acid fragment, which is less than the whole amino acid sequence for the entity and retains essentially the same biological activity or a relevant biological activity, for example greater than 50% activity such as 60%, 70%, 80%, 85%, 90%, 91%, 92%, 93%, 94%, 95%, 96%, 97%, 98%, 99% or 100%.

In another embodiment, the first binding partner X is glutathione (GSH) and the second binding partner Y is glutathione-S-transferase (GST) or vice versa.

In another embodiment, X is Fos and Y is Jun or vice versa.

In another embodiment, X is His and Y is anti-His or vice versa.

In another embodiment, the binding pair is clamodulin binding peptide and Y is calmodulin or vice versa.

In another embodiment, X is maltose-binding protein and Y is an anti-maltose binding protein or fragment thereof or vice versa.

Other enzyme-ligand combinations are also contemplated for use in binding partners. Also suitable are affinity tags known in the art for protein purification because these have a tendency to bind with high affinity to their respective binding partners.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains).

Degrees of identity and similarity can be readily calculated (Computational Molecular Biology, Lesk, A.M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656,).

In one embodiment, the first or second binding partner (X or Y) is a protein or peptide.

In one embodiment, the first and second fusion proteins comprise one or more peptide linkers. The linkers may be incorporated at various locations in the fusion proteins. For example, a linker may be introduced between a binding partner and the protein attached thereto.

In one embodiment, the linker is a peptide linker.

The term "peptide linker" as used herein refers to a peptide with an amino acid sequence. A range of suitable peptide linkers will be known to the person of skill in the art.

In one embodiment, the binding partners of the bispecific protein complexes are joined to their respective proteins via peptide linkers.

In one embodiment the fusion proteins are a translational fusion, that is a fusion protein expressed in a host cell comprising a genetic construct from which the fusion protein is expressed.

In one embodiment the fusion protein is prepared by fusing the heavy chain of A to X and/or the heavy chain of B to Y optionally via a peptide linker.

In one embodiment, the peptide linker is 50 amino acids in length or less, for example 20 amino acids or less.

Generally it will be more efficient to express the fusion protein recombinantly and therefore a direct peptide bond or a peptide linker that can be expressed by a host cell may be advantageous.

In one embodiment, the linker is selected from a sequence shown in sequence 5 to 72 or PPP.

TABLE 1

Hinge linker sequences

| SEQ ID NO: | SEQUENCE |
|---|---|
| 5 | DKTHTCAA |
| 6 | DKTHTCPPCPA |

TABLE 1-continued

Hinge linker sequences

| SEQ ID NO: | SEQUENCE |
|---|---|
| 7 | DKTHTCPPCPATCPPCPA |
| 8 | DKTHTCPPCPATCPPCPATCPPCPA |
| 9 | DKTHTCPPCPAGKPTLYNSLVMSDTAGTCY |
| 10 | DKTHTCPPCPAGKPTHVNVSVVMAEVDGTCY |
| 11 | DKTHTCCVECPPCPA |
| 12 | DKTHTCPRCPEPKSCDTPPPCPRCPA |
| 13 | DKTHTCPSCPA |

TABLE 2

Flexible linker sequences

| SEQ ID NO: | SEQUENCE |
|---|---|
| 14 | SGGGGSE |
| 15 | DKTHTS |
| 16 | (S)GGGGS |
| 17 | (S)GGGGSGGGGS |
| 18 | (S)GGGGSGGGGSGGGGS |
| 19 | (S)GGGGSGGGGSGGGGSGGGGS |
| 20 | (S)GGGGSGGGGSGGGGSGGGGSGGGGS |
| 21 | AAAGSG-GASAS |
| 22 | AAAGSG-XGGGS-GASAS |
| 23 | AAAGSG-XGGGSXGGGS-GASAS |
| 24 | AAAGSG-XGGGSXGGGSXGGGS-GASAS |
| 25 | AAAGSG-XGGGSXGGGSXGGGSXGGGS-GASAS |
| 26 | AAAGSG-XS-GASAS |
| 27 | PGGNRGTTTTRRPATTTGSSPGPTQSHY |
| 28 | ATTTGSSPGPT |
| 29 | ATTTGS |
| 30 | GS |
| 31 | EPSGPISTINSPPSKESHKSP |
| 32 | GTVAAPSVFIFPPSD |
| 33 | GGGGIAPSMVGGGGS |
| 34 | GGGGKVEGAGGGGGS |
| 35 | GGGGSMKSHDGGGGS |
| 36 | GGGGNLITIVGGGGS |
| 37 | GGGGVVPSLPGGGGS |
| 38 | GGEKSIPGGGGS |
| 39 | RPLSYRPPFPFGFPSVRP |

TABLE 2-continued

Flexible linker sequences

| SEQ ID NO: | SEQUENCE |
|---|---|
| 40 | YPRSIYIRRRHPSPSLTT |
| 41 | TPSHLSHILPSFGLPTFN |
| 42 | RPVSPFTFPRLSNSWLPA |
| 43 | SPAAHFPRSIPRPGPIRT |
| 44 | APGPSAPSHRSLPSRAFG |
| 45 | PRNSIHFLHPLLVAPLGA |
| 46 | MPSLSGVLQVRYLSPPDL |
| 47 | SPQYPSPLTLTLPPHPSL |
| 48 | NPSLNPPSYLHRAPSRIS |
| 49 | LPWRTSLLPSLPLRRRP |
| 50 | PPLFAKGPVGLLSRSFPP |
| 51 | VPPAPVVSLRSAHARPPY |
| 52 | LRPTPPRVRSYTCCPTP- |
| 53 | PNVAHVLPLLTVPWDNLR |
| 54 | CNPLLPLCARSPAVRTFP |

(S) is optional in sequences 17 to 20.

Examples of rigid linkers include the peptide sequences GAPAPAAPAPA (SEQ ID NO: 69), PPPP (SEQ ID NO: 70) and PPP.

Other linkers are shown in Table 3:

| SEQ ID NO: | SEQUENCE |
|---|---|
| 55 | DLCLRDWGCLW |
| 56 | DICLPRWGCLW |
| 57 | MEDICLPRWGCLWGD |
| 58 | QRLMEDICLPRWGCLWEDDE |
| 59 | QGLIGDICLPRWGCLWGRSV |
| 60 | QGLIGDICLPRWGCLWGRSVK |
| 61 | EDICLPRWGCLWEDD |
| 62 | RLMEDICLPRWGCLWEDD |
| 63 | MEDICLPRWGCLWEDD |
| 64 | MEDICLPRWGCLWED |
| 65 | RLMEDICLARWGCLWEDD |
| 66 | EVRSFCTRWPAEKSCKPLRG |
| 67 | RAPESFVCYWETICFERSEQ |
| 68 | EMCYFPGICWM |

In one aspect, there is provided a method of producing a bispecific protein complex of the present disclosure, comprising the steps of:

(a) producing a first fusion protein (A-X), comprising a first protein (A), attached to a first binding partner (X) of a binding pair;
(b) producing a second fusion protein (B-Y), comprising a second protein (B), attached to a second binding partner (Y) of a binding pair; and
(c) mixing the first (A-X) and second fusion proteins (B-Y) prepared in step a) and b) together.

Typically the mixing of A-X and B-Y in step (c) is in a 1:1 molar ratio.

In one embodiment each fusion proteins employed in the complexes of the present disclosure are produced by expression in a host cell or host cells in an expression experiment.

In one aspect, there is provided a method of preparing a bispecific protein complex of the present disclosure, comprising the steps of:

(a) expressing a first fusion protein (A-X), comprising a first protein (A), attached to a first binding partner (X) of a binding pair;
(b) expressing a second fusion protein (B-Y), comprising a second protein (B), attached to a second binding partner (Y) of a binding pair;

wherein fusion protein A-X and B—Y are expressed from the same host cell or distinct host cells.

Distinct host cells as employed herein refers to individual cells, including cells of the same type (even same clonal type).

In one embodiment the expression is transient expression. The use of transient expression is highly advantageous when combined with the ability to generate bispecific complexes without recourse to purification. This results in a rapid method to generate bispecific protein complexes as transient transfection is much simpler and less resource intensive than stable transfection.

In one embodiment the expression is stable expression i.e. wherein the DNA encoding the fusion protein in question is stably integrated into the host cell genome.

In one embodiment a polynucleotide encoding A-X and a polynucleotide encoding B-Y on the same or different polynucleotide sequences are transfected into a cell as part of a functional assay, wherein the proteins are expressed in the cell and/or released therefrom. In particular the polynucleotides are transiently transfected on the same of different plasmids.

The mixing of A-X and B—Y is generally effected in conditions where the X and Y can interact. In one embodiment, the fusion proteins are incubated in cell culture media under cell culturing conditions, for example the fusion proteins are incubated for 90 minutes in a 37° C./5% $CO_2$ environment.

In one embodiment the fusion proteins of the present disclosure are mixed in an aqueous environment, for example one fusion protein may be bound to a solid surface such as a bead or a plate and the other fusion protein can be introduced thereto in an aqueous solution/suspension. The solid phase allows excess components and reagents to be washed away readily. In one embodiment neither fusion is attached a solid phase and are simply mixed in a liquid/solution/medium. Thus in one embodiment A-X and B—Y are mixed as free proteins in an aqueous media.

Advantageously, the method of the present disclosure can be employed to prepare complexes formed between heterogenous pairs (i.e. between the first fusion protein [A-X] and second fusion protein [B-Y]) wherein interactions between homogenous pairs (i.e. between two first fusion proteins [A-X] or two second fusion proteins [B-Y]) are minimised. Thus the present method allows large numbers of bispecific protein complexes to be prepared, with minimal or no contamination with homodimeric complexes. An advantage of the constructs and method of the present disclosure is that the ratio of A-X to B-Y is controlled by the properties of the A-X and B—Y and in particular a molar ratio of 1:1 can be achieved. This element of control is a significant improvement over the certain prior art methods.

In one embodiment a method of the present disclosure comprises a further step of transferring a pair variable regions (in particular two pairs of variable regions) identified as having synergistic activity into an alternative bispecific format, optionally humanising said variable regions if necessary beforehand, which is an alternative therapeutic format and/or a format having an extended half-life suitable for testing in assays with a longer duration (for example which run a week or more).

Multivalent formats include those known in the art and those described herein, such as DVD-Igs, FabFvs for example as disclosed in WO2009/040562 and WO2010/035012, diabodies, triabodies, tetrabodies etc.

Other examples of bi and multispecific formats (including therapeutic formats) include a diabody, triabody, tetrabody, tandem scFv, tandem scFv-Fc, FabFv, Fab'Fv, FabdsFv, Fab-scFv, Fab'-scFv, diFab, diFab', scdiabody, scdiabody-Fc, ScFv-Fc-scFv, scdiabody-CH$_3$, IgG-scFv, scFv-IgG, V-IgG, IgG-V, DVD-Ig, and DuoBody.

Diabody as employed herein refers to two Fv pairs: VH/VL and a further VH/VL pair which have two inter-Fv linkers, such that the VH of a first Fv is linked to the VL of the second Fv and the VL of the first Fv is linked to the VH of the second Fv.

Triabody as employed herein refers to a format similar to the diabody comprising three Fv pairs and three inter-Fv linkers.

Tetrabody as employed herein refers to a format similar to the diabody comprising fours Fv pairs and four inter-Fv linkers.

Tandem scFv as employed herein refers to two scFvs (each comprising a linker is the usual manner) linked to each other via a single linker such that there is a single inter-Fv linker.

Tandem scFv-Fc as employed herein refers to two tandem scFvs, wherein each one is appended to the N-terminus of a CH2 domain, for example via a hinge, of constant region fragment —CH2CH3.

FabFv as employed herein refers to a Fab fragment with a variable region appended to the C-terminal of each of the following, the CH1 of the heavy chain and CL of the light chain. The format may be provided as a PEGylated version thereof.

Fab'Fv as employed herein is similar to FabFv, wherein the Fab portion is replaced by a Fab'. The format may be provided as a PEGylated version thereof.

FabdsFv as employed herein refers to a FabFv wherein an intra-Fv disulfide bond stabilises the appended C-terminal variable regions. The format may be provided as a PEGylated version thereof.

Fab-scFv as employed herein is a Fab molecule with a scFv appended on the C-terminal of the light or heavy chain.

Fab'-scFv as employed herein is a Fab' molecule with a scFv appended on the C-terminal of the light or heavy chain.

DiFab as employed herein refers to two Fab molecules linked via their C-terminus of the heavy chains.

DiFab' as employed herein refers to two Fab' molecules linked via one or more disulfide bonds in the hinge region thereof.

As employed herein scdiabody is a diabody comprising an intra-Fv linker, such that the molecule comprises three linkers and forms a normal scFv whose VH and VL terminals are each linked to a one of the variable regions of a further Fv pair.

Scdiabody-Fc as employed herein is two scdiabodies, wherein each one is appended to the N-terminus of a CH2 domain, for example via a hinge, of constant region fragment —CH2CH3. ScFv-Fc-scFv as employed herein refers to four scFvs, wherein one of each is appended to the N-terminus and the C-terminus of both the heavy and light chain of a —CH2CH3 fragment. Scdiabody-CH3 as employed herein refers to two scdiabody molecules each linked, for example via a hinge to a CH3 domain.

IgG-scFv as employed herein is a full length antibody with a scFv on the C-terminal of each of the heavy chains or each of the light chains.

scFv-IgG as employed herein is a full length antibody with a scFv on the N-terminal of each of the heavy chains or each of the light chains.

V-IgG as employed herein is a full length antibody with a variable domain on the N-terminal of each of the heavy chains or each of the light chains.

IgG-V as employed herein is a full length antibody with a variable domain on the C-terminal of each of the heavy chains or each of the light chains DVD-Ig (also known as dual V domain IgG) is a full length antibody with 4 additional variable domains, one on the N-terminus of each heavy and each light chain.

Duobody or 'Fab-arm exchange' as employed herein is a bispecific IgG antibody format where matched and complementary engineered amino acid changes in the constant domains (typically CH3) of two different monoclonal antibodies lead, upon mixing, to the formation of heterodimers. A heavy/light chain pair from the first antibody will, as a result of the residue engineering, prefer to associate with a heavy:light chain pair of a second antibody.

If present constant region domains of a bispecific antibody complex or antibody molecule of the present disclosure, if present, may be selected having regard to the proposed function of the complex or antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant region domains may also be used. For example IgG4 molecules in which the serine at position 241 has been changed to proline as described in Angal et al., 1993, Molecular Immunology, 1993, 30:105-108 may be used. Accordingly, in the embodiment where the antibody is an IgG4 antibody, the antibody may include the mutation S241P.

It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, RJ. Journal of Chromatography 705: 129-134, 1995). Accordingly, the C-terminal lysine of the antibody heavy chain may be absent.

The present disclosure also provides a composition comprising one or more bispecific protein complexes as described above, wherein the composition predominantly comprises heterodimeric bispecific complexes according to the present disclosure, for example with minimal or no contamination with homodimeric complexes.

In one embodiment, at least 60%, at least 65%, at least 70%, at least 75%, at least 80%, at least 90%, or at least 95% of the fusion proteins in the composition are in a bispecific protein complex form.

In one embodiment, at least 60% of the fusion proteins in the composition are in a bispecific protein complex form.

In one embodiment the complexes formed require no further purification steps and thus the compositions comprise unpurified bispecific complexes.

In one embodiment the complexes formed require one purification step, for example column chromatography.

In one embodiment the method further comprises at least one purification step, for example after expression of a fusion protein according to the present disclosure and before mixing the fusion proteins.

In one aspect the present disclosure relates to a fusion protein, a heterodimerically-tethered bispecific protein complex, a composition comprising a fusion protein or said bispecific protein complex, a multiple, array, library as defined herein.

In one embodiment, the bispecific protein complex is in solution or suspension.

In one embodiment, the bispecific protein complexes are fixed on a solid substrate surface.

In one embodiment, the multiplex is in the form of an array, for example in a microplate, such as a 96 or 384 well plate. Such arrays can be readily implemented in screening assays to identify bispecific protein complexes with desired functionality.

In another embodiment, the bispecific protein complexes are conjugated to beads.

A fusion protein as defined above is a component of the bispecific protein complex according to the present disclosure. In one aspect, the present disclosure relates to a fusion protein described herein.

In a further aspect, there is provided a library, comprising two or more fusion proteins as defined above.

The term "library" as used herein refers to two or more bispecific antibody complexes of the present disclosure or multiple fusion proteins of the present disclosure that can be combined to form at least two different bispecific antibody complexes according to the present disclosure. As described throughout the specification, the term "library" is used in its broadest sense and may also encompass sub-libraries.

Advantageously, the library may comprise a range of different fusion proteins which have either the first binding partner (X) or second binding partner (Y) of a particular binding pair attached thereto. In one embodiment part of the library comprises proteins/antibodies/fragments each connected to a binding partner X and the remainder of the library comprises the same proteins/antibodies/fragments each connected to a binding partner Y. This thus allows any two fusion proteins to be readily combined to form a bispecific protein complex of the present disclosure, as long as one fusion protein has the first binding partner of a binding pair attached and the other fusion protein has the second binding partner of the binding pair attached.

In one embodiment bispecific protein complexes of the present invention are suitable for therapeutic applications and may provide novel therapies for treating diseases. Thus in a further aspect, there is provided a bispecific protein complex as described above for use in therapy. The bispecific protein complex is suitable for treating a range of diseases, such as autoimmune disease and cancer.

Conversely, the bispecific protein complexes of the present disclosure can be engineered with one antibody or antibody fragment specific for T-lymphocytes, and another antibody or antibody fragment specific for a cancer-specific antigen. As a result, the bispecific antibody complexes of the present disclosure may advantageously possess a higher cytotoxic potential compared to ordinary monoclonal antibodies.

The bispecific protein complexes of the present disclosure are also particularly suited for inhibiting B cell function in order to control immune and autoimmune reactions in various autoimmune diseases.

Thus, the present disclosure extends to a method of treating a disease in a patient, comprising the administration of a bispecific protein complex of the present disclosure.

In one aspect, there is provided a pharmaceutical composition comprising one or more bispecific protein complexes of the present disclosure.

In one embodiment there is provided a fusion protein obtained or obtainable for a method of the present disclosure.

In one embodiment there is provided an bispecific antibody complex obtained or obtainable from a method of the present disclosure In one embodiment there is provided an a bispecific or multispecific antibody molecule comprising variable regions combinations identified by a method according to the present disclosure.

In one embodiment there is provided a composition, such as a pharmaceutical composition comprising a fusion protein, a bispecific antibody complex or a bispecific/multispecific antibody molecule obtained from a method of the present disclosure.

Various different components can be included in the composition, including pharmaceutically acceptable carriers, excipients and/or diluents. The composition may, optionally, comprise further molecules capable of altering the characteristics of the population of antibodies of the invention thereby, for example, reducing, stabilizing, delaying, modulating and/or activating the function of the antibodies. The composition may be in solid, or liquid form and may inter alia, be in the form of a powder, a tablet, a solution or an aerosol.

The present disclosure also provides a pharmaceutical or diagnostic composition comprising a bispecific protein complex of the present invention in combination with one or more of a pharmaceutically acceptable excipient, diluent or carrier. Accordingly, provided is the use of a bispecific protein complex of the invention for use in the treatment and for the manufacture of a medicament for the treatment of a pathological condition or disorder.

The pathological condition or disorder, may, for example be selected from the group consisting of infections (viral, bacterial, fungal and parasitic), endotoxic shock associated with infection, arthritis such as rheumatoid arthritis, asthma such as severe asthma, chronic obstructive pulmonary disease (COPD), pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, meningoencephalitis, autoimmune uveitis, immune mediated inflammatory disorders of the central and peripheral nervous system such as multiple sclerosis, lupus (such as systemic lupus erythematosus) and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, other autoimmune disorders, pancreatitis, trauma (surgery), graft-versus-host disease, transplant rejection, heart disease including ischaemic diseases such as myocardial infarction as well as atherosclerosis, intravascular coagulation, bone resorption, osteoporosis, osteoarthritis, periodontitis, hypochlorhydia and cancer, including breast cancer, lung cancer, gastric cancer, ovarian cancer, hepatocellular cancer, colon cancer, pancreatic cancer, esophageal cancer, head & neck cancer, kidney, and cancer, in particular renal cell carcinoma, prostate cancer, liver cancer, melanoma, sarcoma, myeloma, neuroblastoma, placental choriocarcinoma, cervical cancer, and thyroid cancer, and the metastatic forms thereof.

The present disclosure also provides a pharmaceutical or diagnostic composition comprising a bispecific protein complex of the present invention in combination with one or more of a pharmaceutically acceptable excipient, diluent or carrier. Accordingly, provided is the use of a bispecific protein complex of the invention for use in treatment and in the manufacture of a medicament.

The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the antibody molecule or bispecific antibody complex of the present invention together with one or more of a pharmaceutically acceptable excipient, diluent or carrier.

The term "pharmaceutically acceptable excipient" as used herein refers to a pharmaceutically acceptable formulation carrier, solution or additive to enhance the desired characteristics of the compositions of the present disclosure. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent solution used for the formulation, aseptic suspension of the antibody in the sterile buffered solvent solution, and dispensing of the formulation into sterile receptacles by methods familiar to those of ordinary skill in the art.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Such carriers enable the pharmaceutical compositions to be formulated as tablets, pills, dragées, capsules, liquids, gels, syrups, slurries and suspensions, for ingestion by the patient.

The bispecific protein complexes of the invention can be delivered dispersed in a solvent, e.g., in the form of a solution or a suspension. It can be suspended in an appropriate physiological solution, e.g., physiological saline, a pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. As mentioned supra a suspension can made, for example, from lyophilised antibody.

A thorough discussion of pharmaceutically acceptable carriers is available in Remington's Pharmaceutical Sciences (Mack Publishing Company, N.J. 1991).

The bispecific antibody complex (or bispecific/multispecific antibody molecule of the present disclosure) may be the sole active ingredient in the pharmaceutical or diagnostic composition or may be accompanied by other active ingredients including other antibody ingredients, for example anti-TNF, anti-IL-1β, anti-T cell, anti-IFNγ or anti-LPS antibodies, or non-antibody ingredients such as xanthines. Other suitable active ingredients include antibodies capable of inducing tolerance, for example, anti-CD3 or anti-CD4 antibodies.

In a further embodiment, the antibody, fragment or composition according to the disclosure is employed in combination with a further pharmaceutically active agent, for example a corticosteroid (such as fluticasone propionate) and/or a beta-2-agonist (such as salbutamol, salmeterol or formoterol) or inhibitors of cell growth and proliferation (such as rapamycin, cyclophosphmide, methotrexate) or alternatively a CD28 and/or CD40 inhibitor. In one embodiment the inhibitor is a small molecule. In another embodiment the inhibitor is an antibody specific to the target.

The pharmaceutical compositions suitably comprise a therapeutically effective amount of the bispecific antibody complex of the invention (or a bispecific/multispecific antibody molecule of the present disclosure).

The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, for example 0.1 mg/kg to 20 mg/kg. Alternatively, the dose may be 1 to 500 mg per day such as 10 to 100, 200, 300 or 400 mg per day. Pharmaceutical compositions may be conveniently presented in unit dose forms containing a predetermined amount of an active agent of the invention.

Compositions may be administered individually to a patient or may be administered in combination (e.g. simultaneously, sequentially or separately) with other agents, drugs or hormones.

The dose at which the antibody molecule of the present invention is administered depends on the nature of the condition to be treated, the extent of the inflammation present and on whether the antibody molecule is being used prophylactically or to treat an existing condition. The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half-life (e.g. 2 to 15 days) it may only be necessary to give a dosage once per day, once per week or even once every 1 or 2 months.

In the present disclosure, the pH of the final formulation is not similar to the value of the isoelectric point of the antibody or fragment, for if the pH of the formulation is 7 then a pI of from 8-9 or above may be appropriate. Whilst not wishing to be bound by theory it is thought that this may ultimately provide a final formulation with improved stability, for example the antibody or fragment remains in solution.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention.

Direct delivery of the compositions will generally be accomplished by injection, subcutaneously, intraperitoneally, intravenously or intramuscularly, or delivered to the interstitial space of a tissue. The compositions can also be administered into a specific tissue of interest. Dosage treatment may be a single dose schedule or a multiple dose schedule.

Where the product is for injection or infusion, it may take the form of a suspension, solution or emulsion in an oily or aqueous vehicle and it may contain formulatory agents, such as suspending, preservative, stabilising and/or dispersing agents. Alternatively, the bispecific protein complex (or bispecific/multispecific antibody molecule of the present disclosure) may be in dry form, for reconstitution before use with an appropriate sterile liquid. If the composition is to be administered by a route using the gastrointestinal tract, the composition will need to contain agents which protect the antibody from degradation but which release the bispecific protein complex once it has been absorbed from the gastrointestinal tract.

A nebulisable formulation according to the present disclosure may be provided, for example, as single dose units (e.g., sealed plastic containers or vials) packed in foil envelopes. Each vial contains a unit dose in a volume, e.g., 2 ml, of solvent/solution buffer.

The term "variant" as used herein refers to peptide or protein that contains at least one amino acid sequence or nucleotide sequence alteration as compared to the amino acid or nucleotide sequence of the corresponding wild-type peptide or protein. A variant may comprise at least 80%, or 85%, or 90%, or 95%, or 98% or 99% sequence identity to the corresponding wild-type peptide or protein. However, it is possible for a variant to comprise less than 80% sequence identity, provided that the variant exhibits substantially similar function to its corresponding wild-type peptide or protein.

Antigens include cell surface receptors such as T cell or B cell signalling receptors, co-stimulatory molecules, checkpoint inhibitors, natural killer cell receptors, Immunolglobulin receptors, TNFR family receptors, B7 family receptors, adhesion molecules, integrins, cytokine/chemokine receptors, GPCRs, growth factor receptors, kinase receptors, tissue-specific antigens, cancer antigens, pathogen recognition receptors, complement receptors, hormone receptors or soluble molecules such as cytokines, chemokines, leukotrienes, growth factors, hormones or enzymes or ion channels, epitopes, fragments and post translationally modified forms thereof.

In one embodiment, the bispecific protein complex comprises one or two cell surface receptor specificities.

In one embodiment, the bispecific protein complex comprises one or two cytokine or chemokine specificities.

Antibodies or fragments to a pair of targets identified by the method according to the present disclosure may be incorporated into any format suitable for use as a laboratory reagent, an assay reagent or a therapeutic.

Thus in one aspect the disclosure extends to use of antibodies fragments or combinations thereof as pairs in any format, examples of which are given above.

The disclosure also extends to compositions, such as pharmaceutical compositions comprising said novel formats with the particular antigen specificity.

In a further aspect the disclosure includes use of the formats and the compositions in treatment.

In one embodiment, the bispecific protein complex of the present disclosure may be used to functionally alter the activity of the antigen or antigens of interest. For example, the bispecific protein complex may neutralize, antagonize or agonise the activity of said antigen or antigens, directly or indirectly.

The present disclosure also extends to a kit, for example comprising:
a) one or more fusion proteins (A-X) comprising a first antibody or antibody fragment (A) attached to a first binding partner of a binding pair (X); and
b) one or more fusion proteins (B-Y) comprising a second antibody or antibody fragment (B) attached to a second binding partner of the binding pair (Y), wherein the latter is specific for the first binding partner;
   for example wherein the first binding partner (X) is a peptide or polypeptide and the second binding (Y) partner is an antibody or antibody fragment specific thereto;
wherein Y the second binding partner is specific to the first binding partner X and the second binding partner is, for example an antibody or antibody fragment specific thereto; and the specific interaction (such as a binding interaction) of the two binding partners forms a heterodimer-tether which physically brings the two fusion proteins from a) and b) together to form a bispecific protein complex; and
wherein the fusion protein(s) is/are in a complexed or a non-complexed form.

Advantageously, the kit may comprise bispecific protein complexes of the present disclosure, or may comprise fusion proteins which are in a complexed or non-complexed form. In the former case, the bispecific protein complexes are ready for use "out of the box" which provides convenience and ease of use, whereas in the latter case, the bispecific protein complexes can be assembled according to the user's requirements by combining different fusion proteins.

In another embodiment, the kit further comprises instructions for use.

In yet another embodiment, the kit further comprises one or more reagents for performing one or more functional assays.

In one embodiment, fusion proteins, bispecific proteins complexes, multiplexes, grids, libraries, compositions etc as described herein are for use as a laboratory reagent.

In a further aspect, there is provided a nucleotide sequence, for example a DNA sequence encoding a fusion protein and/or a bispecific protein complex as defined above.

In one embodiment, there is provided a nucleotide sequence, for example a DNA sequence encoding a bispecific protein complex according to the present disclosure.

In one embodiment there is provided a nucleotide sequence, for example a DNA sequence encoding a bispecific or multispecific antibody molecule according to the present disclosure.

The disclosure herein also extends to a vector comprising a nucleotide sequence as defined above.

The term "vector" as used herein refers to a nucleic acid molecule capable of transporting another nucleic acid to which it has been linked. An example of a vector is a "plasmid," which is a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell, where they are subsequently replicated along with the host genome. In the present specification, the terms "plasmid" and "vector" may be used interchangeably as a plasmid is the most commonly used form of vector.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

The term "selectable marker" as used herein refers to a protein whose expression allows one to identify cells that have been transformed or transfected with a vector containing the marker gene. A wide range of selection markers are known in the art. For example, typically the selectable marker gene confers resistance to drugs, such as G418, hygromycin or methotrexate, on a host cell into which the vector has been introduced. The selectable marker can also be a visually identifiable marker such as a fluorescent marker for example.

Examples of fluorescent markers include rhodamine, FITC, TRITC, Alexa Fluors and various conjugates thereof.

Also provided is a host cell comprising one or more cloning or expression vectors comprising one or more DNA sequences encoding an antibody of the present disclosure. Any suitable host cell/vector system may be used for expression of the DNA sequences encoding the antibody molecule of the present disclosure. Bacterial, for example E. coli, and other microbial systems may be used or eukaryotic, for example mammalian, host cell expression systems may also be used. Suitable mammalian host cells include CHO, myeloma or hybridoma cells.

The present disclosure also provides a process for the production of a fusion protein according to the present disclosure comprising culturing a host cell containing a vector of the present disclosure under conditions suitable for leading to expression of protein from DNA encoding the molecule of the present disclosure, and isolating the molecule.

The bispecific protein complexes of the present disclosure may be used in diagnosis/detection kits, wherein bispecific protein complexes with particular combinations of antigen specificities are used. For example, the kits may comprise bispecific antibody complexes that are specific for two antigens, both of which are present on the same cell type, and wherein a positive diagnosis can only be made if both antigens are successfully detected. By using the bispecific antibody complexes of the present disclosure rather than two separate antibodies or antibody fragments in a non-complexed form, the specificity of the detection can be greatly enhanced.

In one embodiment, the bispecific antibody complexes are fixed on a solid surface. The solid surface may for example be a chip, or an ELISA plate.

Further provided is the use of a bispecific protein complex of the present disclosure for detecting in a sample the presence of a first and a second peptide, whereby the bispecific complexes are used as detection agents.

The bispecific antibody complexes of the present disclosure may for example be conjugated to a fluorescent marker which facilitates the detection of bound antibody-antigen complexes. Such bispecific antibody complexes can be used for immunofluorescence microscopy. Alternatively, the bispecific antibody complexes may also be used for western blotting or ELISA.

In one embodiment, there is provided a process for purifying an antibody (in particular an antibody or fragment according to the invention).

In one embodiment, there is provided a process for purifying a fusion protein or bispecific protein complex according the present disclosure comprising the steps: performing anion exchange chromatography in non-binding mode such that the impurities are retained on the column and the antibody is maintained in the unbound fraction. The step may, for example be performed at a pH about 6-8.

The process may further comprise an initial capture step employing cation exchange chromatography, performed for example at a pH of about 4 to 5.

The process may further comprise of additional chromatography step(s) to ensure product and process related impurities are appropriately resolved from the product stream.

The purification process may also comprise of one or more ultra-filtration steps, such as a concentration and diafiltration step.

"Purified form" as used supra is intended to refer to at least 90% purity, such as 91, 92, 93, 94, 95, 96, 97, 98, 99% w/w or more pure.

In the context of this specification "comprising" is to be interpreted as "including".

Aspects of the disclosure comprising certain elements are also intended to extend to alternative embodiments "consisting" or "consisting essentially" of the relevant elements.

Positive embodiments employed herein may serve basis for the excluding certain aspects of the disclosure.

Disclosures in the context of the method relating to the bispecific complexes apply equally to the complexes per se and vice versa.

Paragraphs:

1. A method for detecting synergistic function in a heterodimerically-tethered bispecific protein complex of formula A-X:Y-B
   wherein X:Y is a heterodimeric-tether,
   A and B are components of the bispecific in the form of fusion proteins with X and Y respectively, said method comprising the steps of:
   (i) testing for activity in a functional assay for part or all of a multiplex comprising at least one heterodimerically-tethered bispecific protein; and
   (ii) analysing the readouts from the functional assay to identify synergistic biological function in the bispecific protein complex.
2. A method for detecting synergistic function in a heterodimerically-tethered bispecific protein complex according to paragraph 1, wherein the method further comprises a first step of forming a multiplex of heterodimerically-tethered bispecific protein complexes.
3. A method for detecting synergistic function in a heterodimerically-tethered bispecific protein complex according to paragraph 1 or 2, wherein X is a peptide or protein and Y is a peptide or protein binding partner specific to X.
4. A method for detecting synergistic function in a heterodimerically-tethered bispecific protein complex according to paragraph 3, wherein the binding affinity of the heterodimeric-tether is 5 nM or stronger.
5. A method for detecting synergistic function in a heterodimerically-tethered bispecific protein complex according to paragraph 4, wherein the binding affinity of the heterodimeric tether is 900 pM or stronger, such as 800, 700, 600, 500, 400 or 300 pM.
6. A method for detecting synergistic function in a heterodimerically-tethered bispecific protein complex according to paragraph 3, wherein X is an antibody or binding fragment thereof.
7. A method for detecting synergistic function in a heterodimerically-tethered bispecific protein complex according to paragraph 6, wherein the X is an antibody fragment selected from the group comprising a Fab, a Fab', a single chain Fv, and a single domain antibody, such as a VHH.
8. A method for detecting a synergistic function in a heterodimerically-tethered bispecific protein complex according to paragraph 7, wherein the X is a single-chain Fv.
9. A method for detecting a synergistic function in a heterodimerically-tethered bispecific protein complex according to paragraph 8, wherein the single chain Fv is specific to the peptide GCN4.
10. A method for detecting a synergistic function in a heterodimerically-tethered bispecific protein complex according to paragraph 9, wherein the single chain Fv is 52SR4.
11. A method for detecting a synergistic function in a heterodimerically-tethered bispecific protein complex according to any one of paragraph 3 to 10, wherein Y is a peptide.
12. A method for detecting a synergistic function in a heterodimerically-tethered bispecific protein complex according to paragraph 11, wherein the peptide is between 5 and 25 amino acids in length.
13. A method for detecting a synergistic function in a heterodimerically-tethered bispecific protein complex according to any one of paragraph 1 to 12, wherein A is an antibody or binding fragment thereof
14. A method for detecting a synergistic function in a heterodimerically-tethered bispecific protein complex according to any one of paragraph 1 to 13, wherein B is an antibody or binding fragment thereof.
15. The method according to any one of the preceding paragraphs wherein the multiplex comprises at least one biological comparator for the at least one heterodimerically-tethered bispecific protein.
16. The method according to any one of paragraph 1 to 15, wherein multiple bispecific protein complexes are tested simultaneously.
17. A bispecific protein complex having the formula A-X:Y-B wherein:
    A-X is a first fusion protein;
    Y—B is a second fusion protein;
    X:Y is a heterodimeric-tether;
    A is a first protein component of the bispecific;
    B is a second protein component of the bispecific;
    X is a first binding partner of a binding pair;
    Y is a second binding partner of the binding pair; and
    : is an interaction (such as a binding interaction) between X and Y.
18. The bispecific protein complex according to paragraph 17, wherein the binding interaction between the X and Y has a low dissociation constant.
19. The bispecific protein complex according to paragraph 18 wherein the dissociation constant is in the range of $1\text{-}9\times10^{-3}\text{s}^{-1}$ or less, for example $1\text{-}9\times10^{-3}\text{s}^{-1}$, $1\text{-}9\times10^{-4}\text{s}^{-1}$, $1\text{-}9\times10^{-5}\text{s}^{-1}$, $1\text{-}9\times10^{-6}\text{s}^{-1}$ or $1\text{-}9\times10^{-7}\text{s}^{-1}$.
20. The bispecific protein complex according to paragraph 19, wherein the dissociation constant is $1\times10^{-4}\text{s}^{-1}$ or less, for example $1\times10^{-5}\text{s}^{-1}$, $1\times10^{-6}\text{s}^{-1}$ or $1\times10^{-7}\text{s}^{-1}$.
21. The bispecific protein complex according to any one of paragraphs 17 to 20, wherein the affinity of X and Y for each other is 5 nM or stronger, for example 900 pM or stronger, such as 800, 700, 600, 500, 400 or 300 pM.
22. The bispecific protein complex according to any one of paragraphs 17 to 21, wherein Y is a peptide or protein.
23. The bispecific protein complex according to paragraph 22, wherein the peptide is GCN4.
24. The bispecific protein complex according to any one of paragraph 16 to 23, wherein X is an antibody or antibody fragment.
25. A bispecific protein complex according to paragraph 24, wherein the antibody fragment is selected from the group consisting of: a Fab, a Fab', a single chain variable fragment (scFv) and a single domain antibody (sdAb), such as VHH.
26. A bispecific protein complex according to paragraph 25, wherein the antibody fragment is a scFv.
27. The bispecific protein complex according to paragraph 26, wherein the scFv is 52SR4.
28. The bispecific complex according to any one of paragraph 17 to 27, wherein X or Y is a peptide and the peptide is other than the peptide epitope referred to an E5B9.
29. The bispecific protein complex according to paragraph 17, wherein the binding partner pairs are selected from wherein:
    (i) X is glutathione (GSH) and Y is glutathione S-transferase (GST),
    (ii) X is Fos and Y is Jun,
    (iii) X is FLAG and Y is an anti-FLAG antibody or fragment thereof, (iv) X is His and Y is anti-His, and (v) X is maltose-binding protein and Y is an anti-maltose binding protein or fragment thereof 30. The bispecific protein complex according to any one of paragraphs 17 to 29, wherein A is selected from the group consisting of an antibody, an antibody fragment, a ligand, a receptor, an inhibitor and an enzyme, such as an antibody or an antibody fragment.

31. The bispecific protein complex according to any one of paragraphs 17 to 30, wherein B is selected from the group consisting of an antibody, an antibody fragment, a ligand, a receptor, an inhibitor and an enzyme, such as an antibody or an antibody fragment.

32. The bispecific protein complex according to any one of paragraphs 30 or 31, wherein A and/or B is an antibody or antibody fragment specific for a cell surface receptor.

33. The bispecific protein complex according to any one of paragraphs 29 to 30, wherein A and/or B is an antibody or antibody fragment is specific for a cytokine or chemokine.

34. The bispecific protein complex according to any one of paragraphs 30 to 34 wherein X is attached to the C-terminal of the heavy or light chain of the first antibody or antibody fragment, for example wherein X is attached to the C-terminal of the heavy chain of the first antibody or antibody binding fragment.

35. The bispecific protein complex according to any one of paragraphs 31 to 35, wherein Y is attached to the C-terminal of the heavy or light chain of the second antibody or antibody binding fragment, for example wherein the Y is attached to the C-terminal of the heavy chain of the second antibody or antibody fragment.

36. The bispecific protein complex according to any one of paragraphs 17 to 36, wherein A is an antibody or antibody binding fragment specific to a first antigen and B is an antibody or antibody fragment specific to a second antigen, wherein the first and second antigens are different.

37. A composition comprising one or more bispecific protein complexes according to any one of paragraphs 17 to 37.

38. The composition according to paragraphs 38, wherein at least 60%, at least 65%, at least 70%, at least 75%, at least 80%, at least 85%, at least 90%, or at least 95% of the fusion proteins are in a bispecific protein complex form.

39. The composition according to paragraphs 39, wherein at least 60% of the fusion proteins are in a bispecific protein complex form.

40. A multiplex of bispecific protein complexes, comprising: at least two bispecific protein complexes according to any one of paragraphs 19 to 37, wherein the bispecific protein complexes have different specificities.

41. The multiplex according to paragraphs 41, wherein the bispecific protein complexes are in solution or fixed on a solid substrate surface.

42. A multiplex according to paragraphs 42, wherein the multiplex is in the form of an array or a grid, for example in a microplate, such as a 96 well plate or 384 well plate.

43. A multiplex according to any one of paragraphs 41 to 43, wherein the bispecific protein complexes are conjugated to beads.

44. A fusion protein A-X or B-Y as defined in any one of paragraphs 1 to 37.

45. A library comprising two or more fusion proteins as defined in any one of paragrpahs 1 to 37.

46. A nucleotide sequence encoding a fusion protein as defined in any one of paragraphs 1 to 37.

47. A vector comprising a nucleotide sequence according to paragraphs 47.

48. A bispecific protein complex according to any one of paragraphs 17 to 37 or a composition according to any one of paragraphs 38 to 40, for use in therapy.

49. A method of treating a patient, comprising the administration of a bispecific protein complex according to any one of paragraphs 7 to 36 or a composition according to any one of paragraphs 37 to 39.

50. A kit, comprising:
    a) one or more fusion proteins A-X; and
    b) one or more fusion proteins B-Y;
       X:Y is a heterodimeric-tether;
       A is a first protein component on of the bispecific;
       B is a second protein of the bispecific;
       X is a first binding partner of a binding pair, such as a peptide or protein;
       Y is a second binding partner of the binding pair, for example a peptide or protein specific to X; and
    wherein X and Y are incapable of forming homodimers, such that a specific binding interaction between X and Y forms a heterodimeric-tether and physically brings the two fusions together to form a bispecific protein complex; and
    wherein the fusion protein(s) in the kit is/are in a complexed or a non-complexed form.

51. The kit according to paragraph 51, further comprising instructions for use. 52. The kit according to paragraph 50 or 51, further comprising one or more reagents for performing one or more functional assays.

All references referred to herein are specifically incorporated by reference.

REFERENCES

1. Ribosome display efficiently selects and evolves high-affinity antibodies in vitro from immune libraries. Hanes J, Jermutus L, Weber-Bornhauser S, Bosshard HR, Plückthun A. (1998) Proc. Natl. Acad. Sci. U.S.A. 95, 14130-14135
2. Directed in Vitro Evolution and Crystallographic Analysis of a Peptide-binding Single Chain Antibody Fragment (scFv) with Low Picomolar Affinity. Zhand C, Spinelli S, Luginbuhl B, Amstutz P, Cambillau C, Pluckthun A. (2004) J. Biol. Chem. 279, 18870-18877
3. Antigen recognition by conformational selection. Berger C, Weber-Bornhauser S, Eggenberger Y, Hanes J, Pluckthun A, Bosshard H. R. (1999) F.E.B.S. Letters 450, 149-153

EXAMPLES

General Methods Employed in Some of the Examples

General Method 1:

Human PBMC derived from platelet apheresis cones were banked as frozen aliquots. Prior to an assay being performed, cells were thawed, washed in DMEM (Life Technologies) and allowed to acclimatise to a 37° C. and 5% $CO_2$ environment.

General Method 2:

Fab'A-X and Fab'B-Y were incubated together for 90 minutes (in a 37° C./5% $CO_2$ environment) before mixing with $2.5 \times 10^5$ PBMC in V-bottomed 96 well plates. PBMC plus bispecific (Fab'A-X and Fab'B-Y) or bivalent (e.g. Fab'A-X FabA'-Y) combinations were then incubated together for a further 90 minutes. After this time B cells were activated by the addition of 200 nM of goat F(ab')2 anti-human IgM (Southern Biotechnology) for 8 minutes at 37° C. The signalling reaction was then halted by adding an equal volume of Cytofix buffer (BD Biosciences). Plates were then left at room temperature for 15 minutes before centrifugation at 500 g for 5 minutes. Excess supernatant was discarded from the cell pellet which was resuspended in flow buffer and washed once more. Cells were then resuspended in ice cold Perm Buffer III (BD Biosciences) for 30 minutes before being washed twice in flow buffer.

Figure 4:
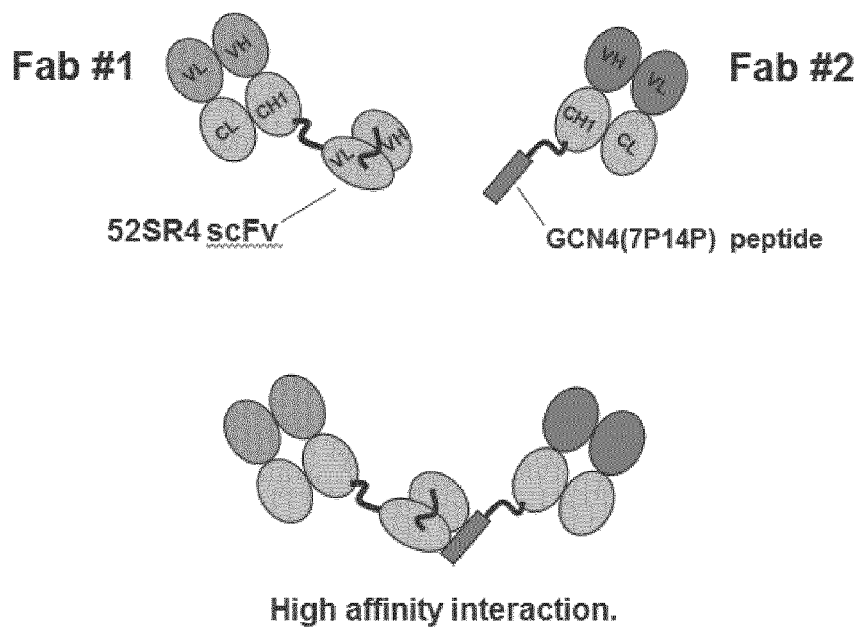
FIG. 4 is a schematic diagram showing a representative bispecific antibody complex of the present disclosure. The diagram depicts how two different Fab fragments come together to form a bispecific antibody complex via the high affinity interaction between the binding partners attached to the Fab fragments.

General Method 3:

Cells were activated as described in general method 2 and stained with a fluorescently labelled anti-CD20 antibody (BD Biosciences), anti-phospho Akt antibody that recognises a modified serine residue at position 473, an anti-phospho PLCg2 antibody that recognises a modified tyrosine residue at position 759 and an anti-IκB antibody that recognised total IκB. Plates were then resuspended and incubated for 1 hour at room temperature in the dark. After this time plates were washed a further two times and resuspended in 25 µl of flow buffer. Cellular expression of CD20, Akt and PLCg2 was measured using an Intellicyt HTFC™ flow cytometer Example 1 Construction of a Bispecific Antibody Complex of the Present Disclosure FabB-GCN4(7P14P):52SR4-FabA FIGS. 2 and 4 show a representative bispecific antibody complex of the present disclosure. The bispecific antibody complex is composed of a first and second fusion protein.

The first fusion protein (A-X) includes a Fab fragment (Fab A (also referred to as Fab#1) with specificity to antigen 6, which is attached to X a scFv (clone 52SR4 SEQ ID NO: 3) via a peptide linker ASGGGG SEQ ID NO: 71 which is linked to the c-terminal of the $CH_1$ domain of the Fab fragment and the $V_L$ domain of the scFv. The scFv itself also contains a peptide linker located in between its $V_L$ and $V_H$ domains.

The second fusion protein (B-Y) includes a Fab fragment (Fab B [also referred to as Fab#2] with specificity to antigen 5). However, in comparison to the first protein, the Fab fragment is attached to Y a peptide GCN4 (clone 7P14P SEQ ID NO: 1) via a peptide linker ASGGGG SEQ ID NO: 71 which is linked to the $CH_1$ domain of the Fab fragment.

The scFv, X, is specific for and complementary to the binding partner Y, GCN4. As a result, when the two fusion proteins are brought into contact with each other, a non-covalent binding interaction between the scFv and GCN4 peptide occurs, thereby physically retaining the two fusion proteins in the form of a bispecific antibody complex.

The single chain antibody (scFv) 52SR4 was derived by constructing and panning a ribosome display VL-linker-VH scFv library from the spleens of mice immunized with GCN4(7P14P) (Reference 1). A further 2004 publication describes the affinity maturation of 52SR4 to a reported 5 pM again using ribosome display of randomised libraries (Reference 2).

The GCN4 peptide was derived from the yeast transcription factor GCN4 by inclusion of Proline residues at positions 7 and 14, hence GCN4(7P14P) remains in a monomeric state on scFv binding as described in a 1999 publication by Berger et al (Reference 3).

The nucleotide sequences encoding the GCN4 peptide and the 52SR4 scFv were cloned into two separate vectors downstream of in-house heavy chain Fab expression vectors which contain $CH_1$ and which are already designed to receive antibody VH-regions.

VH-regions from an anti-antigen 6 antibody and an anti-antigen 5 antibody were then cloned separately into these two heavy chain vectors.

The nucleotide sequences encoding the GCN4 peptide and the 52SR4 scFv were separately cloned into a first and second vector respectively downstream of in-house light chain Fab expression vectors which contain CK and which are designed to receive antibody VL-regions.

VL-regions from an anti-antigen 6 antibody and an anti-antigen 5 antibody were cloned separately in frame with CK in an in-house light chain expression vector for co-expression with the appropriate heavy chain vector to express the Fab-scFv and Fab-peptide proteins.

The vectors were then sequenced to confirm that the cloning has been successful and that the cells subsequently separately expressed Fab-scFv and Fab-peptide proteins with the V-regions from the anti-antigen 6 antibody and the anti-antigen 5 antibody respectively. Antigen 5 and 6 in Example 1 are not the antigens labelled antigen 5 and antigen 6 in later Examples with the large grid formats.

Figure 5:
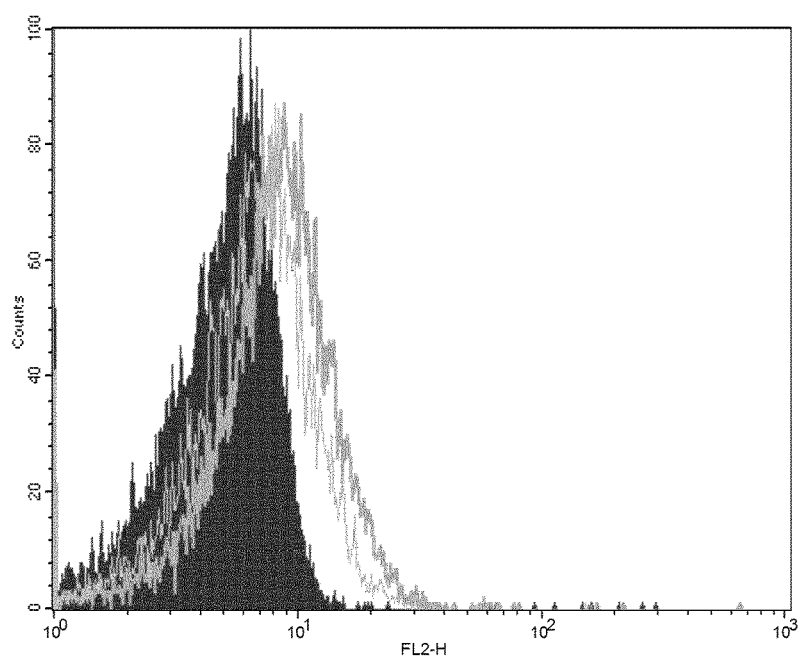
FIG. 5 is a graph showing the results of a flow cytometry experiment which demonstrates that two Fab fragments which are specific for two different target antigens retain their specificities and are able to co-engage their corresponding target antigens simultaneously when the two Fab fragments are combined to form a bispecific antibody complex of the present disclosure. The results further demonstrate that reversing the attachment of the binding partners attached to the Fab fragments does not affect the ability of the Fab fragments to bind specifically to their respective target antigens. The no complex formation control shows no binding detected when both specificities are fused to peptide (Y:Y).

Example 2—Flow Cytometry Demonstration of scFv:Peptide Interaction Forming a Non-Covalent Bispecific Antibody that can Co-Engage Two Target Antigens Simultaneously FIG. 5 shows the results of a flow cytometry experiment which demonstrates the antigen specificities of two different bispecific antibody complexes formed using the scFv:peptide binding interaction.

The first bispecific antibody complex was constructed using the following two fusion proteins:
1. Anti-antigen 5 Fab-scFv (52SR4); and
2. Anti-antigen 6 Fab-peptide (GCN4)

The second bispecific antibody complex was constructed using the following two fusion proteins:
1. Anti-antigen 5 Fab-peptide (GCN4); and
2. Anti-antigen 6 Fab-scFv (52SR4)

Therefore, the two bispecific antibody complexes had the same Fab fragments and same binding partners (i.e. 52SR4 and GCN4). The difference between the two bispecific antibody complexes was in which Fab fragment is attached to which binding partner.

The control mixture which did not form a complex was made from the following fusion proteins:
1. Anti-antigen 5 Fab:GCN4; and
2. Anti-antigen 6 Fab:GCN4

To demonstrate the ability of the bispecific antibody complexes to bind to antigen 5, the complexes were incubated with Jurkat cells which express antigen 5. To demonstrate the ability of the bispecific antibody complexes to bind to antigen 6, the complexes once bound to antigen 5 on Jurkat cells were subsequently contacted with biotinylated antigen 6. The biotinylated antigen 6 was then detected using fluorescently labelled streptavidin.

The Jurkat cells were then run through a Facscalibur flow cytometer machine, wherein the fluorescently labelled Jurkat cells which can only be labelled when bound to a bispecific antibody complex, which is in turn bound to antigen 6, thereby indicating that the bispecific antibody complex is capable of binding to both antigen 5 and antigen 6 can be separated from Jurkat cells incubated with two fusion proteins capable of binding to antigen 5 and antigen 6, both fused to peptide which cannot form a complex.

The FACS plot in FIG. 5 shows significant shifts for both the bispecific antibody complexes (thin and thick line over and above background filled), thus demonstrating that the bispecific antibody complexes can successfully bind to both target antigens and that the ability to bind to both target antigens is retained regardless of whether a given Fab fragment is connected to a scFv or peptide.

The subsequent capture of either peptide or scFv respectively C-terminally fused to the anti-antigen 6 Fab allows further capture of biotinylated antigen 6 which is detected in a final layer with fluorescently labelled streptavidin. Accordingly, the results depicted in the FACS plot shows that the bispecific antibody complexes of the present disclosure are able to successfully bind two different target antigens simultaneously.

Antigen 5 and 6 in Example 2 are not the antigens labelled antigen 5 and antigen 6 in later Examples with the large grid formats below.

Example 3—Biacore Demonstration of scFv:Peptide Interaction

FIG. 6 shows a surface plasmon resonance trace which demonstrates the affinity of the scFv:peptide (i.e. 52SR4:GCN4) interaction. Surface plasmon resonance was performed using a Biacore 3000 (GE Healthcare). All experiments were performed at 25° C. Streptavidin (produced in-house) was immobilised on a CMS Sensor Chip (GE Healthcare) via amine coupling chemistry to a final level of approximately 1750 response units. HBS-N buffer (10 mM HEPES pH 7.4, 0.15M NaCl; GE Healthcare) was used as the running buffer for immobilisation and peptide capture. A 5 µl injection of Biotin-GCN4 peptide in HBS-N (10 nM, M.W. 4360) was used to achieve approximately 6RU of capture on the immobilised streptavidin. The running buffer was switched to HBS-EP+ buffer (10 mM HEPES pH 7.4, 0.15M NaCl, 3 mM EDTA, 0.05% (v/v) surfactant P20; GE Healthcare) for measuring anti-GCN4 (52SR4) scFv binding kinetics. Three-fold serial dilutions of Fab-scFv (generated in-house) from 30 nM, or HBS-EP+ buffer control, were injected over the immobilised GCN4 peptide (3 min association, 15 min dissociation) at a flow rate of 30 µl/min. The surface was regenerated after each injection at a flow-rate of 10 µl/min by two serial 60 sec injection of 2M Guanidine-HCl. Double referenced background subtracted binding curves were analysed using the 3000 BIAEval software (version 4.1) following standard procedures. Kinetic parameters were determined from fitting the 1:1 binding model algorithm. The data demonstrate that the scFv has an affinity for the peptide of 516 pM.

Example 4—Production of Fab-A (Fab-scFv [A-X]) and Fab-B (Fab-peptide [B-Y]) for Functional Assays Cloning Strategy:

Antibody variable region DNA was generated by PCR or gene synthesis flanking restriction enzyme sites DNA sequence. These sites were HindIII and XhoI for variable heavy chains and HindIII and BsiWI for variable light chains. This makes the heavy variable region amenable to ligating into the two heavy chain vectors (pNAFH with FabB-Y and pNAFH with FabA-X) as they have complementary restriction sites. This ligates the variable region upstream (or 5') to the murine constant regions and peptide Y (GCN4) or scFv X (52SR4) creating a whole reading frame. The light chains were cloned into standard in house murine constant kappa vectors (pMmCK or pMmCK S171C) which again use the same complimentary restriction sites. The pMmCK S171C vector is used if the variable region is isolated from a rabbit. The cloning events were confirmed by sequencing using primers which flank the whole open reading frame.

Cultivating CHOSXE:

Suspension CHOSXE cells were pre-adapted to CDCHO media (Invitrogen) supplemented with 2 mM (100×) glutamx. Cells were maintained in logarithmic growth phase agitated at 140 rpm on a shaker incubator (Kuner A G, Birsfelden, Switzerland) and cultured at 37° C. supplemented with 8% $CO_2$.

Electroporation Transfection:

Prior to transfection, the cell numbers and viability were determined using CEDEX cell counter (Innovatis AG. Bielefeld, Germany) and required amount of cells ($2 \times 10^8$ cells/ml) were transferred into centrifuge conical tubes and were spun at 1400 rpm for 10 minutes. The pelleted cells were re-suspended in sterile Earls Balanced Salts Solution and spun at 1400 rpm for further 10 minutes. Supernatant was discarded and pellets were re-suspended to desired cell density.

Vector DNA at a final concentration of 400 µg for $2 \times 10^8$ cells/ml mix and 800 µl was pipetted into cuvettes (Biorad) and electroporated using in-house electroporation system.

Fab-A (Fab-scFv [A-X]) and Fab-B (Fab-Peptide [B-Y] were Transfected Separately.

Transfected cells were transferred directly into 1×3 L Erlenmeyer Flasks contained ProCHO 5 media enriched with 2 mM glutamx and antibiotic antimitotic (100×) solution (1 in 500) and cells were cultured in Kuhner shaker incubator set at 37° C., 5% $CO_2$ and 140 rpm shaking. Feed supplement 2 g/L ASF (AJINOMOTO) was added at 24 hr post transfection and temperature dropped to 32'C for further 13 days culture. At day four 3 mM sodium buryrate (n-butric acid sodium Salt, Sigma B-5887) was added to the culture.

On day 14, cultures were transferred to tubes and supernatant separated from the cells after centrifugation for 30 minutes at 4000 rpm. Retained supernatants were further filtered through 0.22 um SARTOBRAN® P Millipore followed by 0.22 µm Gamma gold filters. Final expression levels were determined by Protein G-HPLC.

Large Scale (1.0 L) Purification:

The Fab-A and Fab-B were purified by affinity capture using the AKTA Xpress systems and HisTrap Excel pre-packed nickel columns (GE Healthcare). The culture supernatants were 0.22 µm sterile filtered and pH adjusted to neutral, if necessary, with weak acid or base before loading onto the columns. A secondary wash step, containing 15-25 mM imidazole, was used to displace any weakly bound host cell proteins/non-specific His binders from the nickel resin. Elution was performed with 10 mM sodium phosphate, pH7.4+1M NaCl+250 mM imidazole and 2 ml fractions collected. One column volume into the elution the system was paused for 10 minutes to tighten the elution peak, and consequently decrease the total elution volume. The cleanest fractions were pooled and buffer exchanged into PBS (Sigma), pH7.4 and 0.22 µm filtered. Final pools were assayed by A280 Scan, SE-HPLC (G3000 method), SDS-PAGE (reduced & non-reduced) and for endotoxin using the PTS Endosafe system.

Example 5-Use of Fab-A (Fab-scFv [A-X]) and Fab-B (Fab-Peptide [B-Y]) in Heterodimerically-Tethered Bispecific Protein Complex Format to Select Functional, Bivalent and Bispecific Antigen Target Combinations Based on Inhibition of Akt Signalling (as a Measure of B Cell Activation)

Human PBMC were prepared according to general method 1. During this period grids of bispecific or bivalent antibodies were created by diluting equimolar (200 nM) quantities of Fab'-A (Fab-scFv) and Fab'-B (Fab-peptide) with varying antigen specificity for the cell surface proteins antigen 3, antigen 1, antigen 4 and antigen 2 in DMEM containing 10% calf serum and 2 mM glutamine. This grid is shown in Table 4.

TABLE 4

Possible grid of bispecific and bivalent combinations of antibodies with specificity for antigen 3, antigen 1, antigen 4 and 2.

| (A-X) Fab A | (B-Y) Fab B | | | |
|---|---|---|---|---|
| | Antigen 3-Y | Antigen 1-Y | Antigen 4-Y | Antigen 2-Y |
| Antigen 3-X | 3-X:Y-3 | 3-X:Y-1 | 3-X:Y-4 | 3-X:Y-2 |
| Antigen 1-X | 1-X:Y-3 | 1-X:Y-1 | 1-X:Y-4 | 1-X:Y-2 |
| Antigen 4-X | 4-X:Y-3 | 4-X:Y-1 | 4-X:Y4 | 4-X:Y-2 |
| Antigen 2-X | 2-X:Y-3 | 2-X:Y-1 | 2-X:Y-4 | 2-X:Y-2 | where X is a scFv (52SR4) and Y is a peptide (GCN4)

Fab'A-X and Fab'B-Y were incubated with PMBCs according to general method 2 following purification as described in Example 4.

Cells were then stained with a fluorescently labelled anti-CD20 antibody (BD Biosciences) and a fluorescently labelled anti-phospho Akt antibody that recognises a modified serine residue at position 473 on the protein. Plates were then resuspended and incubated for 1 hour at room temperature in the dark. After this time plates were washed a further two times and resuspended in 25µl of flow buffer. Cellular expression of CD20 and Akt was measured using an Intellicyt HTFC™ flow cytometer.

Using the data analysis software package FORECYT™ (Intellicyt) B cells were identified as distinct from other cell populations and the geometric mean of Akt levels was calculated for each well. All data was then expressed as the percentage inhibition of the maximal response (anti-IgM only) minus the background (cells only). The relative effect of the combinations of antibodies to antigen 3 (VR0982), antibodies to antigen 1 (VR4247), antibodies to antigen 4 (VR4248) and antibodies to antigen 2 (VR4246) is shown in table 5 ( This data is also represented as a histogram (FIG. 8), showing mean values and the error bars are 95% confidence intervals. The data shows that the combinations of a Fab to antigen 3 (VR0982) with a Fab to antigen 2 (VR4246), a Fab to antigen 1 (VR4247) with a Fab to antigen 2 (VR4246), a Fab to antigen 4 (VR4248) with a Fab to antigen 2 (VR4246) can all inhibit phospho-PLCg2 expression in B cells stimulated with anti-IgM. In contrast, the combinations of a Fab to antigen 3 (VR0982) with a Fab to antigen 3 (VR0982), and a Fab to antigen 3 (VR0982) with a Fab to antigen 4 (VR4248) exhibited elevated levels of phosho-PLCg2 expression. The combination of a Fab to antigen 1 with a Fab to antigen 1 showed no effect.

Example 7—The Use of the Heterodimerically-Tethered Bispecific Protein Complex Format to Select Functional, Bivalent and Bispecific Antigen Target Combinations Based on Inhibition of CD86 Expression (as a Measure of B Cell Activation)

Human PBMC were prepared according to general method 1. During this period grids of bispecific or bivalent antibodies were created by diluting equimolar (200 nM) quantities of Fab'-X (Fab-scFv) and Fab'-Y (Fab-peptide) with antigen specificity for the cell surface proteins antigen 3, antigen 1, antigen 4 and antigen 2 in DMEM containing 10% calf serum and 2 mM glutamine. This grid is shown in Table 7.

Fab'A-X and Fab'B-Y were incubated together for 90 minutes (in a 37° C. & 5% $CO_2$ environment) before mixing with $2.5 \times 10^5$ PBMC in V-bottomed 96 well plates. PBMC plus bispecific or bivalent combinations were then incubated together for a further 90 minutes. After this time B cells were activated by the addition of 200 nM of goat F(ab')2 anti-human IgM (Southern Biotechnology) for 24 hours at 37° C. After this time plates were placed on ice and washed once in ice cold flow buffer (PBS+1% BSA+0.01% $NaN_3$). Cells were then stained with a fluorescently labelled anti-CD19 antibody (BD Biosciences) and a fluorescently labelled anti-CD86 antibody and incubated on ice for 1 hour in the dark. After this time plates were washed a further two times and resuspended in 25 µl of flow buffer. Cellular expression of CD19 and CD86 was measured using an Intellicyt HTFC™ flow cytometer.

Using the data analysis software package FORECYT™ (Intellicyt) B cells were identified as distinct from other cell populations and the geometric mean of CD86 levels was calculated for each well. All data was then expressed as the percentage inhibition of the maximal response (anti-IgM only) minus the background (cells only). The relative effect of the combinations of Fab to antigen 3 (VR0982), Fab to antigen 1 (VR4247), Fab to antigen 4 (VR4248) and Fab to antigen 2 (VR4246) is shown in table 7 (↓=inhibition, ↑=stimulation and ↔=no overall effect). The number of arrows is indicative of the intensity of the activity.

TABLE 7

Table of the relative potency of inhibition of B Cell CD86 expression for bispecific and bivalent combinations of antibodies with specificity for antigen 3, 1, 4 & 2

| (A-X) Fab A specific to | (B-Y) Fab B Antigen 3-Y | Antigen 1-Y | Antigen 4-Y | Antigen 2-Y |
|---|---|---|---|---|
| Antigen 3-X | ↑ | Not Tested | ↔ | ↓↓↓ |
| Antigen 1-X | ↔ | ↔ | ↑↑ | ↔ |
| Antigen 4-X | Not Tested | Not Tested | Not Tested | Not Tested |
| Antigen 2-X | ↓↓↓ | ↓ | ↓↓↓↓ | ↓↓ | where X is a scFv (52SR4) and Y is a peptide (GCN4)

This data is also shown as a histogram (FIG. 9), as mean values and the error bars are 95% confidence intervals. The data shows that the combinations of a Fab to antigen 3 (VR0982) with a Fab to antigen 2 (VR4246), a Fab to antigen 1 (VR4247) with a Fab to antigen 2 (VR4246), a Fab to antigen 4 (VR4248) with a Fab to antigen 2 (VR4246) and a Fab to antigen 2 (VR4246) with a Fab to antigen 2 (VR4246) can all inhibit CD86 expression on B cells stimulated with anti-IgM. In contrast the combinations of a Fab to antigen 3 (VR0982) with a Fab to antigen 3 (VR0982), and a Fab to antigen 1 (VR4247) with a Fab to antigen 4 (VR4248) exhibited elevated levels of CD86 expression. All the other combinations tested showed no effect.

Example 8—the Inhibitory Effect of a Fab to Antigen 1 (VR4247) and a Fab to Antigen 2 (VR4246) can Only be Reproduced when the Antibodies are Arranged in a Bispecific Orientation Human PBMC were prepared according to general method 1. During this period combinations of bispecific, bivalent or mixtures of antibodies were created by diluting equimolar (200 nM) quantities of Fab'A-X (Fab-scFv) and/or Fab'B-Y (Fab-peptide) with antigen specificity for the cell surface proteins antigen 1 and antigen 2 in DMEM containing 10% calf serum and 2 mM glutamine. In addition single fab controls (Fab'-X and Fab'-Y) were also added. These combinations are shown in Table 8.

TABLE 8

Grid of bispecific, bivalent, mixtures or single Fab's with specificity for antigen 1 and antigen 2

| (A-X) Fab A specific to | (B-Y) Fab B — | Antigen 1-Y | Antigen 2-Y | Antigen 2-X |
|---|---|---|---|---|
| Antigen 1-X | 1-X | 1-X:Y-1 | 1-X:Y-2 | 1-X X-2 |
| Antigen 2-X | 2-X | 2-X:Y-1 | 2-X:Y-2 | — |
| Antigen 1-Y | 1-Y | — | 1-Y Y-2 | — |
| Antigen 2-Y | 2-Y | — | — | — | where X is a scFv (52SR4) and Y is a peptide (GCN4)

Fab'A-X and/or Fab'B-Y were incubated according to general method 2.

Cells were then stained with a fluorescently labelled anti-CD20 antibody (BD Biosciences) and a fluorescently labelled anti-phospho Akt antibody that recognises a modified serine residue at position 473 on the protein. Plates were then resuspended and incubated for 1 hour at room temperature in the dark. After this time plates were washed a further two times and resuspended in 25 µl of flow buffer. Cellular expression of CD20 and Akt was measured using an Intellicyt HTFC™ flow cytometer.

Using the data analysis software package FORECYT™ (Intellicyt) B cells were identified as distinct from other cell populations and the geometric mean of Akt levels was calculated for each well. All data was then expressed as the percentage inhibition of the maximal response (anti-IgM only) minus the background (cells only). FIG. 10 shows that only the bispecific combination of a Fab to antigen 1 (VR4247) and a Fab to antigen 2 (VR4246) but not any other combination can modulate B cell phospho-Akt levels (the data represents mean values and the error bars are 95% confidence intervals).

Example 9 the Inhibitory Effect of an Anti-Antigen 3 (VR0982) and an Anti-Antigen 2 (VR4246) can Only be Reproduced when the Antibodies are Arranged in a Bispecific Orientation Human PBMC were prepared according to general method 1. During this period combinations of bispecific, bivalent or mixtures of antibodies were created by diluting equimolar (200 nM) quantities of Fab'-X (Fab-scFv) and/or Fab'-Y (Fab-peptide) with antigen specificity for the cell surface proteins antigen 1 and antigen 2 in DMEM containing 10% calf serum and 2 mM glutamine. These combinations are shown in Table 9.

TABLE 9

Grid of bispecific, bivalent or mixtures with specificity for antigen 3 & 2

| (A-X) | (B-Y) Fab B | | |
|---|---|---|---|
| Fab A specific to | Antigen 3-Y | Antigen 2-Y | Antigen 2-X |
| Antigen 3-X | 3-X:Y-3 | 3-X:Y-2 | 3-X X-2 |
| Antigen 2-X | 2-X:Y-3 | 2-X:Y-2 | — |
| Antigen 3-Y | — | 3-Y Y-2 | — | where X is a scFv (52SR4) and Y is a peptide (GCN4)

Fab'A-X and/or Fab'B-Y were incubated according to general method 2.

Cells were then stained according to general method 3.

Using the data analysis software package FORECYT™ (Intellicyt) B cells were identified as distinct from other cell populations and the geometric mean of Akt and PLCg2 levels were calculated for each well. All data was then expressed as the percentage inhibition of the maximal response (anti-IgM only) minus the background (cells only). FIGS. 11 and 12 show that only the bispecific combination to antigen 3 and antigen 2 but not the mixtures of an anti-antigen 3 (VR0982) and an anti-antigen 2 (VR4246) antibodies inhibited phosphorylated Akt and PLCg2 expression (the data represents mean values and the error bars are 95% confidence intervals).

In order to validate the inhibition seen with the bispecific combination to antigen 3 and to antigen 2, this combination along with a mixture of anti-antigen 3 (VR0982) and anti-antigen 2 (VR4246) antibodies was titrated and inhibition of total intracellular IkB (signalling readout) and CD86 (activation marker after 24 hours) was measured in B cells.

As can be seen in FIG. 13, a combination of antigen-3-X/antigen-2-Y but not the combination of antigen-3-X/antigen-2-X (i.e. as a simple unlinked mixture) was able to inhibit NF-kB signal activation after anti-IgM stimulation as measured by the level of total IkB protein. The $IC_{50}$, as extrapolated using a 4 parameter logistic curve fit using Graphpad Prism 6, was 7.5 nM (the data represents mean values and the error bars are standard deviations). Additionally a titration of the combination of antigen-3-X/antigen-2-Y but not the combination of antigen-3-X/antigen-2-X was able to inhibit anti-IgM induced CD86 expression on B cells after 24 hours (see FIG. 14). The $IC_{50}$, as extrapolated using a 4 parameter logistic curve fit using Graphpad Prism 6, was 10.3 nM (the data represents mean values and the error bars are standard deviations).

Example 10 the Inhibitory Effect of an Anti-Antigen 4 and an Anti-Antigen 2 can Only Reproduced when the Antibodies are Arranged in a Bispecific Orientation Human PBMC were prepared according to general method 1. During this period combinations of bispecific, bivalent or mixtures of antibodies were created by diluting equimolar (200 nM) quantities of Fab'A-X (Fab-scFv) and/or Fab'B-Y (Fab-peptide) with antigen specificity for the cell surface proteins antigen 4 and antigen 2 in DMEM containing 10% calf serum and 2 mM glutamine. These combinations are shown in Table 10.

TABLE 10

Grid of bispecific, bivalent or mixtures with specificity for antigen 4 & 2

| (A-X) | (B-Y) Fab B | |
|---|---|---|
| Fab A | antigen 2-X | antigen 2-Y |
| antigen 4-Y | 2-X:Y-4 | 4-Y Y-2 |
| antigen 2-X | — | 2-X:Y-2 | where X is a scFv (52SR4) and Y is a peptide (GCN4)

Fab'A-X and/or Fab'B-Y were incubated according to general method 2. Cells were then stained according to general method 3.

Using the data analysis software package FORECYT™ (Intellicyt) B cells were identified as distinct from other cell populations and the geometric mean of Akt and PLCg2 levels were calculated for each well. All data was then expressed as the percentage inhibition of the maximal response (anti-IgM only) minus the background (cells only). FIGS. 15 and 16 show that only the bispecific combination of an anti-antigen 4 (VR4248) and an anti-antigen 2 (VR4246) but not the mixtures of anti-antigen 4 (VR4248) and anti-antigen 2 (VR4246) antibodies inhibited phosphorylated Akt and PLCg2 expression (the data represents mean values and the error bars are 95% confidence intervals).

In order to validate the inhibition seen with the bispecific combination of an anti-antigen 4 (VR4248) and an anti-antigen 2 (VR4246), this combination was titrated in an assay system measuring anti-IgM induced CD86 expression on B cells.

As can be seen in FIG. 17, a titration of the combination of antigen 4-X/antigen 2-Y was able to inhibit anti-IgM induced CD86 expression on B cells after 24 hours. The $IC_{50}$, as extrapolated using a 4 parameter logistic curve fit using Graphpad Prism 6, was 4.7 nM (the data represents mean values and the error bars are standard deviations).

Example 11 Bispecific Complex Characterisation

Purification of Functional Screening Reagents:

The functional screening formats Fab-X (Fab-scFv-His) and Fab-Y (Fab-peptide-His) were purified as follows after standard CHO expression. Clarified cell culture supernatants were 0.22 μm sterile filtered using a 1 L stericup. The pH was measured and where necessary adjusted to pH7.4. The prepared supernatants were loaded at 5 ml/min onto 5 ml HisTrap Nickel Excel (GE Healthcare) columns equilibrated in 10 mM Sodium phosphate, 0.5 M NaCl, pH7.4. The columns were washed with 15 mM imidazole, 10 mM Sodium phosphate, 0.5M NaCl, pH7.4 and then eluted with 250 mM imidazole, 10 mM Sodium phosphate, 0.5M NaCl, pH7.4. The elution was followed by absorbance at 280 nm and the elution peak collected. The peak elutions were analysed by size exclusion chromatography on a TSKgel G3000SWXL; 5 μm, 7.8×300 mm column developed with an isocratic gradient of 0.2M phosphate, pH7.0 at 1 ml/min, with detection by absorbance at 280 nm. Samples of sufficient purity were concentrated to >1 m/ml and diafiltered into PBS pH7.4 (Sigma Aldrich Chemicals) using Amicon Ultra-15 concentrators with a 10 kDa molecular weight cut off membrane and centrifugation at 4000×g in a swing out rotor. Where product quality was not sufficient the nickel column elutions were concentrated and applied to either a XK16/60 or XK16/60 Superdex200 (GE Healthcare) column equilibrated in PBS, pH7.4 (Sigma Aldrich Chemicals). The columns were developed with an isocratic gradient of PBS, pH7.4 (Sigma Aldrich Chemicals) at 1 ml/min or 2.6 ml/min respectively. Fractions were collected and analysed by size exclusion chromatography on a TSKgel G3000SWXL; 5 μm, 7.8×300 mm column developed with an isocratic gradient of 0.2 M phosphate, pH7.0 at 1 ml/min, with detection by absorbance at 280 nm. Selected fractions were pooled and concentrated to >1 mg/ml using an Amicon Ultra-15 concentrator with a 10 kDa molecular weight cut off membrane and centrifugation at 4000×g in a swing out rotor.

Analysis of Bispecific Formation in Solution

Experiment 1

Purified Fab-X (VR4247) and purified Fab-Y (VR4248) were mixed in a one to one molar ratio, with a total protein concentration of 500 μg/ml and incubated overnight at ambient temperature. Controls consisted of the individual parts of the mixture at the same concentration as they would be in the mixture. 100 μl of the sample and each control was injected onto a TSKgel G3000SWXL; 5 μm, 7.8×300 mm column developed with an isocratic gradient of 0.2 M phosphate, pH7.0 at 1 ml/min. Detection was by absorbance at 280 nm (see FIG. 18).

The size exclusion chromatograms in FIG. 18 show that the Fab-X (VR4247) control has a main peak of 92% of the total peak area with a retention time of 8.610 metric minutes. The Fab-Y (VR4248) control has a main peak of 94% of the total peak area with a retention time of 10.767 metric minutes. The retention times measured for the Fab-X and Fab-Y controls were converted to apparent molecular weight of 95 kDa and 35 kDa respectively by using a standard curve created from the retention times of BioRad gel filtration standards (151-1901) run under the same conditions. These apparent molecular weights are consistent with the expected apparent molecular weights for Fab-scFv and Fab-peptide molecules. The main peak for the Fab-X (VR4247)/Fab-Y (VR4248) mixture has a retention time of 9.289 metric minutes. This is converted as above to an apparent molecular weight of 187 kDa. This apparent molecular weight is consistent with that expected for the pairing of one Fab-X (VR4247) with one Fab-Y (VR4248). The main peak is also 84% of the total peak area suggesting that most of the Fab-X (VR4247) and Fab-Y (VR4248) have formed the 1 to 1 bispecific protein complex. The small additional shoulder and peak that elute after the main peak are consistent with the Fab-X (VR4247) and Fab-Y (VR4248) starting materials.

Experiment 2

Purified Fab-X (VR4130) and Fab-Y (VR4131) were mixed in a one to one molar ratio, with a total protein concentration of 500 μg/ml. Aliquots of this mixture were then diluted with PBS pH7.4 to a concentration of 50 μg/ml and 5 μg/ml. Controls consisting of the individual parts of the mixture at the same concentration as they would be in the 500 μg/ml mixture were also set up. All mixtures and controls were incubated overnight at ambient temperature. 100 μl of all samples and controls were injected onto a TSKgel G3000SWXL; 5 μm, 7.8×300 mm column developed with an isocratic gradient of 0.2M phosphate, pH7.0 at 1 ml/min. Detection was by absorbance at 214 nm (see FIG. 19, FIG. 20 and Table 11).

The size exclusion chromatograms in FIG. 19 show that the Fab-X (VR4130) control has a main peak of 91% of total peak area with a retention time of 8.634 metric minutes. The Fab-Y (VR4131) control has a main peak of 97% of total peak area with a retention time of 9.361 metric minutes. The retention times measured for the Fab-X and Fab-Y controls were converted to apparent molecular weights of 109 kDa and 55 kDa respectively by using a standard curve created from the retention times of BioRad gel filtration standards (151-1901) run under the same conditions. These apparent molecular weights are consistent with the expected apparent molecular weights for Fab-scFv and Fab-peptide molecules. The main peak for the Fab-X (VR4130)/Fab-Y (VR4131) mixture has a retention time of 8.016 metric minutes. This was converted as above to an apparent molecular weight of 198 kDa. This apparent molecular weight is consistent with that expected for the pairing of one Fab-X (VR4130) with one Fab-Y (VR4131). The main peak is also 82% of the total peak area suggesting that most of the Fab-X (VR4130) and Fab-Y (VR4131) have formed the 1 to 1 complex. The two small peaks that elute after the main peak are consistent with the Fab-X (VR4130) and Fab-Y (VR4131) starting materials.

The size exclusion chromatograms in FIG. 20 are for the Fab-X (VR4130)/Fab-Y (VR4131) 1 to 1 mixtures at 500 μg/ml, 50 μg/ml and 5 μg/ml concentration. All the traces are similar with corresponding peaks between samples having similar retention times and similar relative peak heights and areas. The percentage peak area is collated in Table 11, where the % of each peak remains fairly constant upon dilution of the mixture. This indicates that the Fab-X/Fab-Y 1 to 1 complex remains as a complex at all the concentrations tested. 75% of the Fab-X and Fab-Y are present as the 1 to 1 complex even when the mixture is diluted to 5 μg/ml which is equivalent to concentration of 40 nM for the complex.

TABLE 11

Size exclusion peak area data for Fab-X (VR4130)/Fab-Y (VR4131)
1:1 molar ratio mixtures at 500 µg/ml, 50 µg/ml and
5 µg/ml. Peaks were detected at an absorbance of 214 nm.

| Concentrations | | % Peak Area | | |
|---|---|---|---|---|
| µg/ml | nM | Fab-X (VR4130)/ Fab-Y (VR4131) 1 to 1 complex | Fab-X (VR4130) | Fab-Y (VR4131) |
| 500 | 4000 | 82% | 4% | 5% |
| 50 | 400 | 81% | 11% | 3% |
| 5 | 40 | 75% | 21% | 3% |

Hence, the results of these experiments indicate that a high proportion of the Fab-X and Fab-Y fusion proteins form the desired bispecific complexes, with a minimal proportion of monomers left over and no evidence of homodimer formation.

Example 12: Grid Screening of Large Panels of Heterodimerically Tethered Protein Complexes to Identify Novel Bispecific Antibody Targets Introduction:

Following the successful validation of the bispecific format and screening method in the earlier examples the screening was expanded to a larger number of antigen pairs. A panel of antibody variable (V) region pairs to 23 different antigens expressed on B cells was generated. Using the Fab-Kd-Fab [i.e. A-X:Y-B wherein A and B are Fab fragments] format a grid of heterodimerically tethered protein complexes was formed representing multiple V region combinations of each of 315 different antigen pair combinations. These combinations were screened for their ability to modulate BCR (B cell receptor) signalling in a high through-put flow cytometry assay to select novel target pairs for intervention with a bispecific antibody.

Immunisation:

DNA encoding selected antigens was obtained by gene synthesis or commercial sources & cloned into an expression vector with a strong constitutive promoter. Plasmid DNA was then transfected into Rab-9 rabbit fibroblast cells (ATCC® CRL-1414™) using an in-house electroporation system. Twenty four hours later cells were checked for antigen expression by flow cytometry & frozen in aliquots in liquid nitrogen until use. Up to 6 antigens were immunised per rabbit by either co-expression on the same cell or making mixtures of singly or multiple transfected cells. Rabbits were immunised with 3 doses of cells.

Antibody Discovery:

B cell cultures were prepared using a method similar to that described by Zubler et al. (1985). Briefly, spleen or PBMC-derived B cells from immunized rabbits were cultured at a density of approximately 2000-5000 cells per well in bar-coded 96-well tissue culture plates with 200 µl/well RPMI 1640 medium (Gibco BRL) supplemented with 10% FCS (PAA laboratories ltd), 2% HEPES (Sigma Aldrich), 1% L-Glutamine (Gibco BRL), 1% penicillin/streptomycin solution (Gibco BRL), 0.1% β-mercaptoethanol (Gibco BRL), 3% activated splenocyte culture supernatant and gamma-irradiated mutant EL4 murine thymoma cells ($5 \times 10^4$/well) for seven days at 37° C. in an atmosphere of 5% $CO_2$.

The presence of antigen-specific antibodies in B cell culture supernatants was determined using a homogeneous fluorescence-based binding assay using HEK293 cells co-transfected with the antigens that the rabbits were immunized with. Screening involved the transfer of 10 ul of supernatant from barcoded 96-well tissue culture plates into barcoded 384-well black-walled assay plates containing HEK293 cells transfected with target antigen (approximately 3000 cells/well) using a Matrix Platemate liquid handler. Binding was revealed with a goat anti-rabbit IgG Fcγ-specific Cy-5 conjugate (Jackson). Plates were read on an Applied Biosystems 8200 cellular detection system.

Following primary screening, positive supernatants were consolidated on 96-well bar-coded master plates using an Aviso Onyx hit-picking robot and B cells in cell culture plates frozen at −80° C. Master plates were then screened in a homogeneous fluorescence-based binding assay on HEK293 cells transfected with antigens separately and SUPERAVIDIN™ beads (Bangs Laboratories) coated with recombinant protein as a source of antigen. This was done in order to determine the antigen specificity for each well.

To allow recovery of antibody variable region genes from a selection of wells of interest, a deconvolution step was performed to enable identification of the antigen-specific B cells in a given well that contained a heterogeneous population of B cells. This was achieved using the Fluorescent foci method (Clargo et al., 2014.Mabs 2014 Jan. 1: 6(1) 143-159; EP1570267B1). Briefly, Immunoglobulin-secreting B cells from a positive well were mixed with either HEK293 cells transfected with target antigen or streptavidin beads (New England Biolabs) coated with biotinylated target antigen and a 1:1200 final dilution of a goat anti-rabbit Fcγ fragment-specific FITC conjugate (Jackson). After static incubation at 37° C. for 1 hour, antigen-specific B cells could be identified due to the presence of a fluorescent halo surrounding that B cell. A number of these individual B cell clones, identified using an Olympus microscope, were then picked with an Eppendorf micromanipulator and deposited into a PCR tube. The fluorescent foci method was also used to identify antigen-specific B cells from a heterogeneous population of B cells directly from the bone marrow of immunized rabbits.

Antibody variable region genes were recovered from single cells by reverse transcription (RT)-PCR using heavy and light chain variable region-specific primers. Two rounds of PCR were performed, with the nested secondary PCR incorporating restriction sites at the 3' and 5' ends allowing cloning of the variable region into mouse Fab-X and Fab-Y (VH) or mouse kappa (VL) mammalian expression vectors. Heavy and light chain constructs for the Fab-X and Fab-Y expression vectors were co-transfected into HEK-293 cells using Fectin 293 (Life Technologies) or Expi293 cells using Expifectamine (Life Technologies) and recombinant antibody expressed in 6-well tissue culture plates in a volume of 5 ml. After 5-7 days expression, supernatants were harvested. Supernatants were tested in a homogeneous fluorescence-based binding assay on HEK293 cells transfected with antigen and SUPERAVIDIN™ beads (Bangs Laboratories) coated with recombinant protein or antigen transfected HEK cells. This was done to confirm the specificity of the cloned antibodies.

Production of Small Scale Fab A-X and Fab B-Y (Small Scale (50 mL) Expi293 Transfection)

The Expi293 cells were routinely sub-cultured in EXPI293™ Expression Medium to a final concentration of $0.5 \times 10^6$ viable cells/mL and were incubated in an orbital shaking incubator (Multitron, Infors HT) at 120 rpm 8% $CO_2$ and 37° C.

On the day of transfection cell viability and concentration were measured using an automated Cell Counter (Vi-CELL, Beckman Coulter). To achieve a final cell concentration of $2.5 \times 10^6$ viable cells/mL the appropriate volume of cell suspension was added to a sterile 250 mL Erlenmeyer shake flask and brought up to the volume of 42.5 mL by adding fresh, pre-warmed EXPI293™ Expression Medium for each 50 mL transfection.

To prepare the lipid-DNA complexes for each transfection a total of 50 µg of heavy chain and light chain plasmid DNAs were diluted in OPTI-MEM® I medium (LifeTechnologies) to a total volume of 2.5 mL and 135 µL of EXPI-FECTAMINE™ 293 Reagent (LifeTechnologies) was diluted in OPTI-MEM® I medium to a total volume of 2.5 mL. All dilutions were mixed gently and incubate for no longer than 5 minutes at room temperature before each DNA solution was added to the respective diluted EXPI-FECTAMINE™ 293 Reagent to obtain a total volume of 5 mL. The DNA-EXPIFECTAMINE™ 293 Reagent mixtures were mixed gently and incubated for 20-30 minutes at room temperature to allow the DNA-EXPIFECTAMINE™ 293 Reagent complexes to form.

After the DNA-EXPIFECTAMINE™ 293 reagent complex incubation was completed, the 5 mL of DNA-EXPI-FECTAMINE™ 293 Reagent complex was added to each shake flask. The shake flasks were incubated in an orbital shaking incubator (Multitron, Infors HT) at 120 rpm, 8% $CO_2$ and 37° C.

Approximately 16-18 hours post-transfection, 250 µL of EXPIFECTAMINE™ 293 Transfection Enhancer 1 (LifeTechnologies) and 2.5 mL of EXPIFECTAMINE™ 293 Transfection Enhancer 2 (LifeTechnologies) were added to each shake flask.

The cell cultures were harvested 7 days post transfection. The cells were transferred into 50 mL spin tubes (Falcon) and spun down for 30 min at 4000 rpm followed by sterile filtration through a 0.22 µm Stericup (Merck Millipore). The clarified and sterile filtered supernatants were stored at 4° C. Final expression levels were determined by Protein G-HPLC.

Small Scale (50 ml) Purification:

Both Fab-X and Fab-Y were purified separately by affinity capture using a small scale vacuum based purification system. Briefly, the 50 ml of culture supernatants were 0.22 µm sterile filtered before 500 µL of Ni Sepharose beads (GE Healthcare) were added. The supernatant beads mixture was then tumbled for about an hour before supernatant was removed by applying vacuum. Beads were then washed with Wash 1 (50 mM Sodium Phosphate 1 M NaCl pH 6.2) and Wash 2 (0.5 M NaCl). Elution was performed with 50 mM sodium acetate, pH4.0+1M NaCl. The eluted fractions buffer exchanged into PBS (Sigma), pH7.4 and 0.22 µm filtered. Final pools were assayed by A280 scan, SE-UPLC (BEH200 method), SDS-PAGE (reduced & non-reduced) and for endotoxin using the PTS Endosafe system.

Screening Assays

Donor PBMCs were rapidly thawed using a water bath set to 37° C., and carefully transferred to a 50 ml Falcon tube. They were then diluted dropwise to 5 ml in assay media to minimise the osmotic shock. The cells were then diluted to 20 ml carefully before adding the final media diluent to make the volume 50 ml. The cells were then spun at 500 g for 5 minutes before removing the supernatant and resuspending the cells in 1 ml media. The cells were then counted and diluted to $1.66 \times 10^6$ cells/ml before dispensing 30 µl per well into a V-bottom TC plate giving a final assay concentration of $5.0 \times 10^4$ cells/well. The cell plate was then stored covered in a 37° C., 5% $CO_2$ incubator until they were required, giving them a minimum of 1 hour to rest.

Fab-X and Fab-Y reagents were mixed in an equimolar ratio at 5× the final assay concentration in assay media and incubated for 90 min at 37° C., 5% $CO_2$. Samples were prepared in a 96-well U-bottom polypropylene plate and covered during the incubation. 10 µl of 5× Fab-KD-Fab mixture was added to the appropriate test wells containing cells and mixed by shaking at 1000 rpm for 30 sec prior to being incubated for 90 min at 37° C., 5% $CO_2$.

The cells were then stimulated with 10µl of anti-human IgM. The final assay concentration of stimulus varied depending on the assay panel readouts, the three antibody cocktails A, B and C (detailed below) were stimulated at a final assay concentration of either 50 µg/ml (cocktail A & C) or 25 µg/ml (cocktail B). The assay plates were then gently mixed at 1000 rpm for 30 sec prior to incubation at 37° C., 5% $CO_2$ for 5 min (antibody cocktail A & C) or 2 min (antibody cocktail B). The assay was stopped by adding 150 µl ice-cold BD CytoFix to all wells and incubated for 15 min at RT. The fixed cells were then spun at 500 g for 5 min to pellet the cells and allow removal of the supernatant using a BioTek ELx405 plate washer. The pellet was re-suspended by vortexing the plate at 2400 rpm for 30 sec. The cells were then permeabilised at 4° C. by adding 100 µl ice-cold BD Cell Permeabilisation Buffer III for 30 min. The cells were then washed in 100 µl FACS buffer and spun at 500 g for 5 min. Supernatant was again removed by the ELx405 before using it to rapidly dispense 200 µl FACS Buffer to wash away any residual permeabilisation buffer. Cells were again spun at 500 g and the supernatant removed by inversion. During the preceding spin step the antibody cocktail was prepared in FACS Buffer and kept shielded from the light. The cells were then re-suspended by vortexing (2400 RPM, 30 sec) before 20 µl of antibody cocktail was added to all wells and the plate shaken for 30 sec at 1000 rpm. The cells were then incubated for 60 min at RT in the dark.

The cells were then washed twice in 200 µl FACS buffer with a 500 g spin and supernatant removed after each step. Finally the cells were re-suspended by vortexing for 30 sec at 2400 rpm before adding a final 20 µl FACS buffer. The plate(s) were then read on the Intellicyt HTFC/iQue instrument.

FACS Buffer=PBS+1% BSA+0.05% $NaN_3$+2 mM EDTA
Antibody Cocktail A=1:2 CD20 PerCp-Cy5.5 (BD Biosciences)+1:5 PLCγ2 AF88+1:10 Akt AF647+1:50 ERK1/2 PE (diluted in FACS buffer).

Antibody Cocktail B=1:2 CD20 PerCp-Cy5.5 (BD Biosciences)+1:5 Syk PE+1:5 BLNK AF647 (diluted in FACS buffer)

Antibody Cocktail C=1:5 CD20 PerCp-Cy5.5 (Biolegend)+1:5 PLCγ2 AF488+1:10 Akt AF647+1:5 Syk PE (diluted in FACS buffer)

| Reagent | Supplier | Catalogue number |
|---|---|---|
| Anti-human IgM | Southern Biotech | 2022-14 |
| CytoFix | BD Biosciences | 554655 |
| Perm Buffer III | BD Biosciences | 558050 |
| Anti Akt (pS473) AF647 | BD Biosciences | 561670 |
| Anti SYK (pY348) PE | BD Biosciences | 558529 |
| Anti PLCγ2 (pY759) AF488 | BD Biosciences | 558507 |
| Anti-BLNK(pY84) AF647 | BD Biosciences | 558443 |
| Anti ERK1/2 (pT202/pY204) PE | BD Biosciences | 561991 |
| Anti-human CD20 PerCp-Cy5.5 | BD Biosciences | 558021 |
| Anti-human CD20 AF488 | BD Biosciences | 558056 |
| Anti-human CD20 PerCp-Cy5.5 | Biolegend | 340508 |

| Reagent | Supplier | Catalogue number |
|---|---|---|
| Phosphate Buffer Saline (PBS) | Fisher Scientific | 10562765 |
| RPMI 1640 | Life Technologies | 31870 |
| Foetal Calf Serum (FCS) | Life Technologies | 16140 |
| Glutamax | Life Technologies | 35050 |
| Penicillin/Streptomycin (P/S) | Life Technologies | 15070 |
| EDTA | Sigma | 03690 |
| Sodium Azide (NaN3) | Sigma | S2002 |
| Bovine Serum Albumin (BSA) | Sigma | A1470 |

Fab-X+Fab-Y combinations were screened with either antibody cocktail A and B or C alone. All screens were conducted on cone cells from 2 different blood donors. Data was captured and evaluated using commercially available software tools. A total of 2500 Fab-X+Fab-Y combinations were screened to 315 different antigen combinations.

Results

The percentage inhibition of the induction of phosphorylation of BCR signalling cascade proteins by each Fab-Kd-Fab [i.e. A-X:Y-B where A and B are Fab fragments] combination was calculated, in this example looking for new combinations of antigens that inhibit B cell function, the criteria for a positive combination was set as at least 30% inhibition of at least two phospho-readouts by at least one combination of V regions. According to this threshold 11 new antigen pair combinations out of 315 examined met the required criteria. This represents a 3.5% hit rate demonstrating the importance of screening large numbers of combinations to find those of desired activity.

FIGS. 21-23 show the data for the antigen grid cross specificities. Values are percentage inhibition (negative value for activation) of phosphorlylation of Syk, PLCg2 & AKT respectively and represent the mean of multiple V-region combinations evaluated. 315 different antigen combinations were tested and as can be seen the effect on BCR signalling by different combinations of antibody varied significantly from strong inhibition e.g. antigen 2 on Fab-X combined with antigen 3 and 4 on Fab-Y (69.66% and 70.4% inhibition of phospho Syk FIG. 21) to activation e.g antigen 6 on X and antigen 11 on Y (minus 118.10% phospho Syk FIG. 21).

Each data point representing the mean % values represented in FIGS. 21-23 is shown for antigen 2 on Fab-X and antigen 3 on Fab-Y in FIG. 24. In this case, 23 different combinations of different antibody V regions were evaluated. The same antigen combination but in alternative orientation, i.e. antigen 2 on Fab-Y and antigen 3) on Fab-X is shown in FIG. 25. In this case, 9 different combinations of different antibody V-regions were evaluated. All V regions show inhibition but advantageously this method can also be used in the selection of optimal V-region combinations.

Similarly, each data point representing the mean % values represented in FIGS. 21-23 is shown for antigen combination 2 on Fab-X and antigen 4 on Fab-Y in FIG. 26. In this case, 10 different combinations of different antibody V regions were evaluated. The same antigen combination but in alternative orientation, i.e. antigen 2 on Fab-Y and antigen 4 on Fab-X is shown in FIG. 27. In this case, 6 different combinations of different antibody V regions were evaluated. Again, all V regions show inhibition but optimal V region combinations can be identified and selected using the method.

Example 13—Evaluation of Transiently Expressed Heterodimerically Tethered Protein Complexes to Evaluate Whether FabA-X:Y-FabB Grid Screening can Identify Novel Bispecific Antibody Targets without Recourse to Protein Purification Introduction:

V-regions to 2 different antigens, 2 and 3 that inhibit B cell signalling as a bispecific antibody which were identified using the Fab-Kd-Fab [FabA-X:Y-FabB] format and grid screening of heterodimerically tethered protein complexes were expressed transiently as FabA-X and FabB-Y. The activity of transiently expressed (without subsequent purification) and a purified FabA-X and FabB-Y combination was compared to evaluate whether grid screening could be conducted with the direct products of transient expression instead of purified components.

Immunisation:

The preparation of antigen expressing cells and immunisation of rabbits was carried out in the same way as described in Example 12.

Antibody Discovery

B cell cultures were prepared in the same way as described in Example 12.

The screening of antigen-specific antibodies in B cell culture supernatants and the deconvolution step for identification of antigen specific B cells was determined in the same way as described in Example 12.

Antibody variable region genes were recovered from single cells by reverse transcription (RT)-PCR using heavy and light chain variable region-specific primers. Two rounds of PCR were performed, with the nested 2° PCR incorporating restriction sites at the 3' and 5' ends allowing cloning of the variable region into mouse Fab-X and Fab-Y (VH) or mouse kappa (VL) mammalian expression vector. A 3° PCR was then performed enabling the combination of amplified variable regions, human CMV promoter fragment and rabbit gamma 1 heavy constant or rabbit kappa constant fragment to generate separate heavy and light transcriptionally active PCR (TAP) fragments. These DNA fragments were used directly for recombinant expression of rabbit full-length IgG antibodies in HEK-293 cells using 293Fectin (Life Technologies) or in Expi293 cells using Expifectamine (Life Technologies). The resulting recombinant antibodies were then screened for antigen binding using a homogeneous fluorescence-based binding assay on HEK-293 cells transfected with antigen and SUPERAVIDIN™ beads (Bangs Laboratories) coated with recombinant protein. Once specificity was confirmed with the TAP transients, antibody genes were cloned into Fab-X and Fab-Y expression vectors. Heavy and light chain constructs were co-transfected into HEK-293 cells using Fectin 293 (Life Technologies) or Expi293 cells using Expifectamine (Life Technologies) and recombinant antibody expressed in 6-well tissue culture plates in a volume of 5 ml. After 5-7 days expression, supernatants were harvested. Supernatants were tested in a homogeneous fluorescence-based binding assay on HEK293 cells transfected with antigen and SUPERAVIDIN™ beads (Bangs Laboratories) coated with recombinant protein or antigen transfected HEK cells. This was done to confirm the specificity of the cloned antibodies.

Production of Transient Supernatants Containing Fab-X and Fab-Y

The same Expi293 transfection method described in Example 12 was used to produce the transient supernatants containing Fab-X and Fab-Y.

Production of Purified Fab-X and Fab-Y Suspension CHOSXE cells were pre-adapted to CDCHO media (Invitrogen) supplemented with 2 mM (100×) glutamx. Cells were maintained in logarithmic growth phase agitated at 140 rpm on a shaker incubator (Kuner A G, Birsfelden, Switzerland) and cultured at 37° C. supplemented with 8% $CO_2$.

Prior to transfection, the cell numbers and viability were determined using CEDEX cell counter (Innovatis AG. Bielefeld, Germany) and required amount of cells ($2\times10^8$ cells/ml) were transferred into centrifuge conical tubes and were spun at 1400 rpm for 10 minutes. The Pelleted cells were re-suspended in sterile Earls Balanced Salts Solution and spun at 1400 rpm for further 10 minutes. Supernatant was discarded and pellets were re-suspended to desired cell density.

Vector DNA at a final concentration of 400 ug for $2\times10^8$ cells/ml mix and 800 μl was pipetted into Cuvettes (Biorad) and electroporated using in-house electroporation system.

Transfected cells were transferred directly into 1×3 L Erlenmeyer Flasks contained ProCHO 5 media enriched with 2 mM glutamx and antibiotic antimitotic (100×) solution (1 in 500) and Cells were cultured in Kuhner shaker incubator set at 37° C., 5% $CO_2$ and 140 rpm shaking. Feed supplement 2 g/L ASF (AJINOMOTO) was added at 24 hr post transfection and temperature dropped to 37° C. for further 13 days culture. At day four 3 mM sodium buryrate (n-butric acid sodium salt, Sigma B-5887) was added to the culture.

On day 14, cultures were transferred to tubes and supernatant separated from the cells after centrifugation for 30 minutes at 4000 rpm. Retained supernatants were further filtered through 0.22 μm SARTOBRAN® P Millipore followed by 0.22 μm Gamma gold filters. Final expression levels were determined by Protein G-HPLC.

The Fab-X and Fab-Y were purified by affinity capture using the AKTA Xpress systems and HisTrap Excel pre-packed nickel columns (GE Healthcare). The culture supernatants were 0.22 μm sterile filtered and pH adjusted to neutral, if necessary, with weak acid or base before loading onto the columns. A secondary wash step, containing 15-25 mM Imidazole, was used to displace any weakly bound host cell proteins/non-specific His binders from the nickel resin. Elution was performed with 10 mM sodium phosphate, pH7.4+1 M NaCl+250 mM imidazole and 2 ml fractions collected. One column volume into the elution the system was paused for 10 minutes to tighten the elution peak, and consequently decrease the total elution volume. The cleanest fractions were pooled and buffer exchanged into PBS (Sigma), pH7.4 and 0.22 μm filtered. Final pools were assayed by A280 Scan, SE-HPLC (G3000 method), SDS-PAGE (reduced & non-reduced) and for endotoxin using the PTS Endosafe system.

Functional Assays

Activation Marker Assay:

Antigen 2-specific Fab'-Y and antigen 3-specific Fab'-X, either purified or in transient supernatant, were incubated together for 60 minutes (in a 37° C. & 5% $CO_2$ environment) at equimolar concentration. The combinations were titrated from a starting molarity of 185 nM, in 1:4 serial dilutions. A mock supernatant was also included, titrated from neat. In V-bottomed 96 well plates, $1.5\times10^5$ PBMC were added to wells, to which were added titrated Fab'-X and Fab'-Y combinations or mock supernatant. The combinations and cells were then incubated together for a further 90 minutes. After this time B cells were activated by the addition of 12.5 μg/mL of goat F(ab')2 anti-human IgM (Southern Biotechnology) for 24 hours at 37° C. plus 5% $CO_2$.

To the wells were added 100 μL, ice-cold FACS buffer (PBS+1% BSA+0.1% $NaN_3$+2 mM EDTA), the plates were sealed and covered with wet-ice for approximately 15 minutes, before centrifuging at 500×g for 5 minutes at 4° C. Excess supernatant was discarded from the cell pellets and the plates shaken at 2000 rpm for 30 seconds.

Cells were then stained with a cocktail of fluorescently labelled anti-CD19, anti-CD20 and anti-CD71 antibodies (BD Biosciences). Plates were shaken briefly and incubated for 1 hour on wet-ice in the dark. After this time plates were washed twice and resuspended in 20 μL of FACS buffer. Cellular expression of CD19, CD20 and CD71 was measured using an Intellicyt IQUE® Screener flow cytometer.

Using the data analysis software package FORECYT™ (Intellicyt) B cells were identified as distinct from other cell populations and the geometric mean of CD71 levels were calculated for each well. All data was then expressed as the percentage inhibition of the maximal response (anti-IgM only) minus the background (cells only).

PhosFlow Assay:

Antigen 2-specific Fab'-Y and antigen 3-specific Fab'-X, either purified or in transient supernatant, were incubated together for 60 minutes (in a 37° C. & 5% $CO_2$ environment) at equimolar concentration. The combinations were titrated from a starting molarity of 185 nM, in 1:4 serial dilutions. A mock supernatant was also included, titrated from neat. In V-bottomed 96 well plates, $5.0\times10^4$ PBMC were added to wells, to which were added titrated Fab'-X and Fab'-Y combinations or mock supernatant. The combinations and cells were then incubated together for a further 90 minutes. After this time B cells were activated by the addition of 25 μg/mL of goat F(ab')2 anti-human IgM (Southern Biotechnology) for 15 minutes at 37° C. plus 5% $CO_2$. The signalling reaction was then halted by adding an equal volume of Cytofix buffer (BD Biosciences). Plates were then left at room temperature for 15 minutes before centrifugation at 500×g for 5 minutes. Excess supernatant was discarded from the cell pellet which was resuspended in FACS buffer (PBS+1% BSA+0.01% $NaN_3$+2 mM EDTA) and washed once more. Cells were then resuspended in ice cold Perm Buffer III (BD Biosciences) for 30 minutes before being washed twice in flow buffer. Cells were then stained with a fluorescently labelled anti-CD20 antibody (BD Biosciences) and an anti-phosphorylated p38 antibody that recognises the conserved dual phosphorylated site pT180/pY182. Plates were then resuspended and incubated for 1 hour at room temperature in the dark. After this time plates were washed a further two times and resuspended in 20 μL of FACS buffer. Cellular expression of CD20 and phospho-p38 was measured using an Intellicyt IQUE® flow cytometer.

Using the data analysis software package FORECYT™ (Intellicyt) B cells were identified as distinct from other cell populations and the geometric mean of p38 levels were calculated for each well. All data was then expressed as the percentage inhibition of the maximal response (anti-IgM only) minus the background (cells only).

Results

Activation Marker Assay:

As can be seen in FIG. 28, the data shows that the combination of Antigen 3 with Antigen 2 whether purified or from transient supernatant, can inhibit CD71 expression on B-cells stimulated with anti-IgM.

PhosFlow Assay:

The data in FIG. 29 shows that the combination of Antigen 3 with Antigen 2 whether purified or from transient supernatant, can inhibit phosphorylated p38 in B-cells stimulated with anti-IgM.

The surprising ability to be able to construct the bispecific complexes of the present invention directly from transiently expressed cultures without recourse to purification allows even higher throughput screening of bispecific complexes to be achieved than when purified components are used.

Example 14—Screening of Transiently Expressed V-Regions to Antigen 3 as Fab-X with Purified Anti-Antigen 2 Fab-Y in Heterodimerically Tethered Protein Complexes to Select Optimal Antigen 3 Antibody V-Regions Introduction:

New V-regions to Antigen 3 that inhibit B cell signalling as a bispecific antibody in combination with Antigen 2 specific V regions were identified using grid screening of heterodimerically tethered protein complexes. The Antigen 3 V regions were expressed transiently as Fab-X and combined with purified ant-antigen 2 Fab-Y. The inhibition of activation of B cell signalling was measured to select the most potent Antigen 3 and antigen 2 V regions.

The preparation of antigen expressing cells and immunisation of rabbits was carried out in the same way as described in Example 12.

Antibody Discovery:

B cell cultures were prepared in the same way as described in Example 12.

The screening of antigen-specific antibodies in B cell culture supernatants and the deconvolution step for identification of antigen specific B cells was determined in the same way as Example 12.

Additional variable regions were discovered by the direct foci method directly from spleen and bone marrow-derived B cells of immunized mice. Briefly, cells at a final density of between $4\times10^5$ and $8\times10^5$ cells/ml were mixed with streptavidin beads (New England Biolabs) coated with biotinylated antigenand a 1:1200 final dilution of goat anti-mouse Fcy fragment-specific FITC conjugate (Jackson). After static incubation at 37° C. for 1 hour, antigen-specific B cells could be identified due to the presence of a fluorescent halo surrounding that B cell. A number of these individual B cell clones, identified using an Olympus microscope, were then picked with an Eppendorf micromanipulator and deposited into a PCR tube.

Antibody variable region genes were recovered from single cells by reverse transcription (RT)-PCR using heavy and light chain variable region-specific primers. Two rounds of PCR were performed, with the nested 2° PCR incorporating restriction sites at the 3' and 5' ends allowing cloning of the variable region into mouse Fab-X and mouse kappa (VL) mammalian expression vector. These vectors were then co-transfected in HEK-293 cells using 293Fectin (Life Technologies) or in Expi293 cells using Expifectamine (Life Technologies) and left to express for 6 days. Supernatants were tested in a homogeneous fluorescence-based binding assay on HEK293 cells transfected with antigen and SUPERAVIDIN™ beads (Bangs Laboratories) coated with recombinant protein or antigen transfected HEK cells. This was done to confirm the specificity of the cloned antibodies.

In addition to the Fab-X transient supernatants, negative control Mock supernatants were prepared in the same way using an irrelevant control DNA.

The expression levels of Fab-X were determined by Protein G-HPLC.

Production of Purified Fab-Y:

Purified Fab-Y was prepared using the same method described in Example 13

Functional Assay

The same functional assay as described in Example 12 was used, except that instead of 3 different antibody cocktails, only one cocktail was used with the same assay concentrations and incubation conditions as described for antibody cocktail A in Example 12.

Antibody Cocktail=1:3 CD20 PerCp-Cy5.5+1:5 PLCγ2 AF88+1:10 Akt AF647+1:5 p38 MAPK PE (diluted in FACS buffer).

Results

As can be seen in FIGS. 30-33, the data shows that the combination of different transiently expressed antigen 3 mouse V regions in Fab-X with 2 different purified antigen 2 V regions (VR447 and VR4450) in Fab-Y can inhibit B cell activation to different levels and screening therefore facilitates selection of optimal V regions. Combinations with transient Fab-X are compared to a reference combination with a purified Fab-X (VR4126).

Example 15—Comparison of the Activity of Antigen 2 Plus Antigen 3 Co-Targeting in Fab-Kd-Fab Screening Format to a Molecularly Linked Bispecific BYbe Format Introduction:

To check that target pair activity identified in the Fab-Kd-Fab heterodimerically tethered screening complex could translate to similar desired activity in an alternative therapeutic molecularly linked format, Antigen 2 specificity (VR4447) and antigen 3 specificity (VR4130) were generated in a BYbe format. This BYbe format consists of the anti-Antigen 3 V regions (VR4130) as a disulphide stabilised (ds) single chain (sc)-Fv fused to the heavy chain of the anti-Antigen 2 Fab (VR4447).

Methods:

As described in Example 13 except the purification of BYbes for functional screening was performed as follows:

The functional screening BYbe (Fab-dsscFv [scFv off C-terminus of Fab heavy chain]) formats were purified as follows. Clarified cell culture supernatants from standard expiHEK or CHO expression were 0.22 μm sterile filtered. The filtered supernatants were loaded at 2 ml/min onto 50 ml GammabindPlus Sepharose XK26 columns (GE Healthcare) equilibrated in PBS pH7.4 (Sigma Aldrich Chemicals). After loading the columns were washed with PBS pH7.4 and then eluted with 0.1M Glycine/HCl. pH2.7. The elution was followed by absorbance at 280 nm, the elution peak collected, and then neutralised with $1/25^{th}$ volume of 2M Tris/HCl pH8.5. The neutralised samples were concentrated using Amicon Ultra-15 concentrators with a 10 kDa (BYbes) molecular weight cut off membrane and centrifugation at 4000×g in a swing out rotor. Concentrated samples were applied to either a XK16/60 or XK26/60 Superdex200 column (GE Healthcare) equilibrated in PBS, pH7.4. The columns were developed with an isocratic gradient of PBS, pH7.4 at either 1 ml/min or 2.6 ml/min respectively. Fractions were collected and analysed by size exclusion chromatography on a TSK gel G3000SWXL; 5 μm, 7.8×300 mm column developed with an isocratic gradient of 0.2M phosphate, pH7.0 at 1 ml/min, with detection by absorbance at 280 nm. Selected monomer fractions were pooled and concentrated to >1 mg/ml using an Amicon Ultra-15 concentrator with a 10 kDa molecular weight cut off membrane and centrifugation at 4000×g in a swing out rotor. Final samples were assayed; for concentration by A280 Scanning UV-visible spectrophotometer (Cary 50Bio); for % monomer by size exclusion chromatography on a TSK gel G3000SWXL; 5 µm, 7.8×300 mm column developed with an isocratic gradient of 0.2 M phosphate, pH7.0 at 1 ml/min, with detection by absorbance at 280 nm; by reducing and non-reducing SDS-PAGE run on 4-20% Tris-Glycine 1.5 mm gels (Novex) at 50 mA (per gel) for 53 minutes; and for endotoxin by Charles River's ENDOSAFE® Portable Test System with Limulus Amebocyte Lysate (LAL) test cartridges.

Functional Assays

Activation Marker Assay:

Antigen 2-specific Fab'-Y and Antigen 3-specific Fab'-X, were incubated together for 60 minutes (in a 37° C. and 5% $CO_2$ environment) at equimolar concentration. The combinations were titrated from a starting molarity of 100 nM, in 1:4 serial dilutions. Antigen 2 and 3-specific BYbe was also titrated from a starting molarity of 100 nM, in 1:4 serial dilutions. In V-bottomed 96 well plates, $1.5 \times 10^5$ PBMC were added to wells, to which were added titrated Fab'-X and Fab'-Y combinations or titrated BYbe. The Fab'-X and Fab'-Y combinations or BYbe were incubated with cells for a further 90 minutes. After this time B cells were activated by the addition of 25 µg/mL of goat F(ab')2 anti-human IgM (Southern Biotechnology) for 24 hours at 37° C. plus 5% $CO_2$.

To the wells were added 100 µL ice-cold FACS buffer (PBS+1% BSA+0.1% $NaN_3$+2 mM EDTA), the plates were sealed and covered with wet-ice for approximately 15 minutes, before centrifuging at 500×g for 5 minutes at 4° C. Excess supernatant was discarded from the cell pellets and the plates shaken at 2000 rpm for 30 seconds.

Cells were then stained with a cocktail of fluorescently labelled anti-CD19, anti-CD20 and anti-CD71, anti-CD40 and anti-CD86 antibodies (BD Biosciences). Plates were shaken briefly and incubated for 1 hour on wet-ice in the dark. After this time plates were washed twice and resuspended in 20 µL of FACS buffer. Cellular expression of CD19, CD20 and CD71, CD40 and CD86 was measured using an Intellicyt IQUE® Screener flow cytometer.

Using the data analysis software package FORECYT™ (Intellicyt) B cells were identified as distinct from other cell populations and the geometric mean of CD71, CD40 and CD86 levels were calculated for each well. All data was then expressed as the percentage inhibition of the maximal response (anti-IgM only) minus the background (cells only).

PhosFlow Assay:

Antigen 2-specific Fab'-Y and Antigen 3-specific Fab'-X, were incubated together for 60 minutes (in a 37° C. and 5% $CO_2$ environment) at equimolar concentration. The combinations were titrated from a starting molarity of 100 nM, in 1:4 serial dilutions. Antigen 2 and Antigen 3-specific BYbe was also titrated from a starting molarity of 100 nM, in 1:4 serial dilutions. In V-bottomed 96 well plates, $5.0 \times 10^4$ PBMC were added to wells, to which were added titrated Fab'-X and Fab'-Y combinations or titrated BYbe. The Fab'-X and Fab'-Y combinations or BYbe were incubated with cells for a further 90 minutes. After this time B cells were activated by the addition of 25 µg/mL of goat F(ab')2 anti-human IgM (Southern Biotechnology) for 15 minutes at 37° C. plus 5% $CO_2$. The signalling reaction was then halted by adding an equal volume of Cytofix buffer (BD Biosciences). Plates were then left at room temperature for 15 minutes before centrifugation at 500×g for 5 minutes. Excess supernatant was discarded from the cell pellet which was resuspended in FACS buffer (PBS+1% BSA+0.01% $NaN_3$+2 mM EDTA) and washed once more. Cells were then resuspended in ice cold Perm Buffer III (BD Biosciences) for 30 minutes before being washed twice in flow buffer.

Cells were then stained with a fluorescently labelled anti-CD20 antibody (BD Biosciences) and anti-phosphorylated PLCγ2, anti-phosphorylated Akt and anti-phosphorylated p38 antibodies (BD Biosciences). Plates were then resuspended and incubated for 1 hour at room temperature in the dark. After this time plates were washed a further two times and resuspended in 20 µL of FACS buffer. Cellular expression of CD20 and phospho-PLCγ2, phospho-Akt and phospho-p38 were measured using an Intellicyt IQUE® flow cytometer. Using the data analysis software package FORECYT™ (Intellicyt) B cells were identified as distinct from other cell populations and the geometric mean of PLCγ2, Akt and p38 levels were calculated for each well. All data was then expressed as the percentage inhibition of the maximal response (anti-IgM only) minus the background (cells only).

Results

PhosFlow Assay:

The data in FIG. 34 show that targeting antigen 3 and antigen 2 either in the Fab-Kd-Fab or BYbe format can inhibit phosphorylated PLCγ2 in B-cells stimulated with anti-IgM. The data in FIG. 35 show that targeting antigen 3 and antigen 2 either in the Fab-Kd-Fab or BYbe format can inhibit phosphorylated P38 in B-cells stimulated with anti-IgM. The data in FIG. 36 show that targeting antigen 3 and antigen 2 either in the Fab-Kd-Fab or BYbe format can inhibit phosphorylated Akt in B-cells stimulated with anti-IgM.

Activation Marker Assay:

As can be seen in FIG. 37, the data show that targeting antigen 3 and antigen 2 either in the Fab-Kd-Fab or BYbe format can inhibit CD71 expression on B-cells stimulated with anti-IgM. The data in FIG. 38 show that targeting antigen 3 and antigen 2 either in the Fab-Kd-Fab or BYbe format can inhibit CD40 expression on B-cells stimulated with anti-IgM. The data in FIG. 39 show that targeting antigen 3 and antigen 2 either in the Fab-Kd-Fab or BYbe format can inhibit CD86 expression on B-cells stimulated with anti-IgM Example 16—Comparison of the Activity of Antigen 2 Plus Antigen 3 Co-Targeting in a Molecularly Linked Bispecific Bybe Format with the Further Addition of an Anti-Albumin Binding Domain for Extention of In Vivo Half-Life Introduction:

To check that target pair activity identified in the Fab-Kd-Fab heterodimerically tethered screening complex could translate to similar desired activity in a potential therapeutic molecularly linked format with an anti-albumin targeted in vivo half-life extension, an anti-albumin antibody fragment was fused to the light chain of the antigen 3 Fab of the BYbe format described in Example 15. Antigen 2 specificity (VR4447) and antigen 3 specificity (VR4130 and VR4126)

were generated in a Bybe format with and without addition of an anti-albumin fragment (VR0645).

Description of constructs used in this experiment.

| Construct Name | Fab Specificity | Heavy Chain | Light Chain |
|---|---|---|---|
| VR4447/VR4126 BYbe | Antigen 2 | Antigen 3 | None |
| VR4447/VR4126/VR645) BYbe/Albumin | Antigen 2 | Antigen 3 | Albumin |
| VR4447/VR4130 BYbe | Antigen 2 | Antigen 3 | None |
| VR4447/VR4130/VR645) BYbe/Albumin | Antigen 2 | Antigen 3 | Albumin |

Methods

Purification of BYbes for Functional Screening:

The functional screening BYbe (Fab-dsscFv [scFv off C-terminus of Fab heavy chain]) format was purified as follows. Clarified cell culture supernatants from standard expiHEK or CHO expression were 0.22 μm sterile filtered. The filtered supernatants were loaded at 2 ml/min onto 50 ml GammabindPlus Sepharose XK26 columns (GE Healthcare) equilibrated in PBS pH7.4 (Sigma Aldrich Chemicals). After loading the columns were washed with PBS pH7.4 and then eluted with 0.1M Glycine/HCl. pH 2.7. The elution was followed by absorbance at 280 nm, the elution peak collected, and then neutralised with $\frac{1}{25}^{th}$ volume of 2 M Tris/HCl pH8.5. The neutralised samples were concentrated using Amicon Ultra-15 concentrators with either a 10 kDa or 30 kDa molecular weight cut off membrane and centrifugation at 4000×g in a swing out rotor. Concentrated samples were applied to either a XK16/60 or XK26/60 Superdex 200 column (GE Healthcare) equilibrated in PBS, pH7.4. The columns were developed with an isocratic gradient of PBS, pH7.4 at either 1 ml/min or 2.6 ml/min respectively. Fractions were collected and analysed by size exclusion chromatography on a TSK gel G3000SWXL; 5 μm, 7.8×300 mm column developed with an isocratic gradient of 0.2 M phosphate, pH 7.0 at 1 ml/min, with detection by absorbance at 280 nm. Selected monomer fractions were pooled and concentrated to >1 mg/ml using an Amicon Ultra-15 concentrator with a 10 kDa or 30 kDa molecular weight cut off membrane and centrifugation at 4000×g in a swing out rotor. Final samples were assayed; for concentration by A280 Scanning UV-visible spectrophotometer (Cary 50Bio); for % monomer by size exclusion chromatography on a TSK gel G3000SWXL; 5 μm, 7.8×300 mm column developed with an isocratic gradient of 0.2 M phosphate, pH7.0 at 1 ml/min, with detection by absorbance at 280 nm; by reducing and non-reducing SDS-PAGE run on 4-20% Tris-Glycine 1.5 mm gels (Novex) at 50 mA (per gel) for 53 minutes; and for endotoxin by Charles River's ENDOSAFE® Portable Test System with Limulus Amebocyte Lysate (LAL) test cartridges.

100 nM of each construct purified protein were pre-incubated with human PBMC derived from five separate donors for 60 min at 37 degree C./5% $CO_2$ in RMPI 1640 media plus 10% foetal bovine serum and 2 mM Glutamax (R10 media). After 60 min cells were stimulated with 25 ug/ml of a goat anti-IgM antibody designed to stimulate B cells only. 24 hours later plates were placed on ice to halt any further cell activation before washing once with ice cold flow cytometry buffer (PBS+1% BSA+0.01% $NaN_3$). All supernatant was removed and cell pellets resuspended. Cells were placed on ice and a cocktail of anti-CD19, -CD20, -CD27, -CD71 and CD86 antibodies added. Cells were incubated for 60 min before washing twice in flow cytometry buffer. Data on the binding of anti-CD27, -CD71 and CD86 to CD19/CD20 positive B cells was generated using an iQUE high throughput flow cytometer. Forecyt software was used to generate histograms and derive geometric mean intensity readings for the binding of anti-CD27, -CD71 and CD86 antibodies to B cells. This data was imported into Excel and percentage inhibition values generated for each combination. The data was then imported into Graphpad Prism and box and whisker charts generated for each combination with the mean indicated by a '+'.

FIG. 40 shows the inhibition of CD27 expression on B cells induced by VR4447NR4126 BYbe and VR4447/VR4126/VR645 BYbe/Albumin. Across the five donors tested both showed consistently similar levels of inhibition of anti-IgM induced CD27. FIG. 41 shows the inhibition of CD71 expression on B cells induced by VR4447NR4126 BYbe and VR4447/VR4126/VR645 BYbe/Albumin. Across the five donors both showed consistently similar levels of inhibition of anti-IgM induced CD71. FIG. 42 shows the inhibition of CD86 expression on B cells induced by VR4447/VR4126 BYbe and VR4447/VR4126/VR645 BYbe/Albumin. Across the five donors both showed consistently similar levels of inhibition of anti-IgM induced CD86.

GCN4(7P14P) sequences

SEQ ID NO: 1
*ASGGG*RMKQLEPKVEELLPKNYHLENEVARLKKLVGERHHHHHH
wherein the amino acids in bold are optional and the amino acids in italics are the linking sequence SEQ ID NO: 2
GCTAGCGGAGGCGGAAGAATGAAACAACTTGAACCCAAGGTTGAAGAATT
GCTTCCGAAAAATTATCACTTGGAAAATGAGGTTGCCAGATTAAAGAAAT
TAGTTGGCGAACGCCATCACCATCACCATCAC 52SR4 ds scFv- sequence

SEQ ID NO: 3
DAVVTQESALTSSPGETVTLTCRSSTGAVTTSNYASWVQEKPDHLFTGLI

GGTNNRAPGVPARFSGSLIGDKAALTITGAQTEDEAIYFCVLWYSDHWVF

GCGTKLTVLGGGGSGGGGSGGGGSGGGGSDVQLQQSGPGLVAPSQSLSI

TCTVSGFLLTDYGVNWVRQSPGKCLEWLGVIWGDGITDYNSALKSRLSVT

KDNSKSQVFLKMNSLQSGDSARYYCVTGLFDYWGQGTTLTVSSAAAHHHH

HHEQKLISEEDL-

SEQ ID NO: 4
GATGCGGTGGTGACCCAGGAAAGCGCGCTGACCAGCAGCCCGGGCGAAAC

CGTGACCCTGACCTGCCGCAGCAGCACCGGCGCGGTGACCACCAGCAACT

ATGCGAGCTGGGTGCAGGAAAAACCGGATCATCTGTTTACCGGCCTGATT

GGCGGCACCAACAACCGCGCGCCGGGCGTGCCGGCGCGCTTTAGCGGCAG

CCTGATTGGCGATAAAGCGGCGCTGACCATTACCGGCGCGCAGACCGAAG

ATGAAGCGATTTATTTTTGCGTGCTGTGGTATAGCGACCATTGGGTGTTT

GGCTGCGGCACCAAACTGACCGTGCTGGGTGGAGGCGGTGGCTCAGGCGG

AGGTGGCTCAGGCGGTGGCGGGTCTGGCGGCGGCGGCAGCGATGTGCAGC

TGCAGCAGAGCGGCCCGGGCCTGGTGGCGCCGAGCCAGAGCCTGAGCATT

ACCTGCACCGTGAGCGGCTTTCTCCTGACCGATTATGGCGTGAACTGGGT

GCGCCAGAGCCCGGGCAAATGCCTGGAATGGCTGGGCGTGATTTGGGGCG

ATGGCATTACCGATTATAACAGCGCGCTGAAAAGCCGCCTGAGCGTGACC

-continued

AAAGATAACAGCAAAAGCCAGGTGTTTCTGAAAATGAACAGCCTGCAGAG

CGGCGATAGCGCGCGCTATTATTGCGTGACCGGCCTGTTTGATTATTGGG

-continued

GCCAGGGCACCACCCTGACCGTGAGCAGCGCGGCCGCCCATCACCATCAC

CATCACGAACAGAAACTGATTAGCGAAGAAGATCTGTAATAG

---

The invention claimed is:

1. A bispecific protein complex having the formula A-X:Y-B wherein:
   - A-X is a first fusion protein;
   - Y-B is a second fusion protein;
   - : is a binding interaction between X and Y to form a bispecific protein complex between the first and second fusion proteins:
   - A is a first protein component of the bispecific protein complex selected from a Fab or Fab' fragment;
   - B is a second protein component of the bispecific protein complex selected from a Fab or Fab' fragment;
   - X is a first binding partner of a binding pair independently selected from an antigen or an antibody or binding fragment thereof,
   - wherein when X is an antigen, Y is an antibody or binding fragment thereof specific to the antigen represented by X; and
   - Y is a second binding partner of the binding pair independently selected from an antigen or an antibody or a binding fragment thereof,
   - wherein when Y is an antigen, X is an antibody or binding fragment thereof specific to the antigen represented by Y;
   - wherein A and B bind to two different epitopes on an antigen, or bind two different antigens, and wherein X or Y is a scFv specific to the peptide GCN4 having SEQ ID NO:1 or amino acids 1 to 38 of SEQ ID NO:1 and wherein the scFv is 525R4 having SEQ ID NO:3 or amino adds 1 to 243 of SEQ ID NO:3; or wherein X or Y is a peptide GCN4 having SEQ ID NO:1 or amino acids 1 to 38 of SEQ ID NO: 1.

2. The bispecific protein complex according to claim 1, wherein A is a Fab fragment.

3. The bispecific protein complex according to claim 1, wherein B is a Fab fragment.

4. The bispecific protein complex according to claim 1, wherein X is fused, optionally via a linker, to the C-terminal of the heavy chain in the Fab or Fab' fragment.

5. The bispecific protein complex according to claim 1, wherein Y is fused, optionally via a linker, to the C-terminal of the heavy chain in the Fab or Fab' fragment.

6. The bispecific protein complex according to claim 1, wherein A and/or B is specific for an antigen selected from the group consisting of cell surface receptors, co-stimulatory molecules, checkpoint inhibitors, natural killer cell receptors, Immunoglobulin receptors, TNFR family receptors, B7 family receptors, adhesion molecules, integrins, cytokine/chemokine receptors, GPCRs, growth factor receptors, kinase receptors, tissue-specific antigens, cancer antigens, pathogen recognition receptors, complement receptors, hormone receptors, soluble molecules, cytokines, chemokines, leukotrienes, growth factors, hormones, enzymes, and ion channels.

7. The bispecific protein complex of claim 1, wherein the bispecific protein complex is a biparatopic.

8. The bispecific protein complex of claim 1, wherein the bispecific protein complex binds two different antigens.

9. A composition comprising one or more bispecific protein complexes defined in claim 1.

\* \* \* \* \*

SEQUENCE LISTING

<160> NUMBER OF SEQ ID NOS: 72

<210> SEQ ID NO 1
<211> LENGTH: 44
<212> TYPE: PRT
<213> ORGANISM: Artificial Sequence
<220> FEATURE:
<223> OTHER INFORMATION: GCN4(7P14P) sequence

<400> SEQUENCE: 1

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Lys
            20                  25                  30

Lys Leu Val Gly Glu Arg His His His His His His
        35                  40

<210> SEQ ID NO 2
<211> LENGTH: 132
<212> TYPE: DNA
<213> ORGANISM: Artificial Sequence
<220> FEATURE:
<223> OTHER INFORMATION: DNA encoding SEQ ID NO: 1

<400> SEQUENCE: 2
gctagcggag gcggaagaat gaaacaactt gaacccaagg ttgaagaatt gcttccgaaa      60
aattatcact tggaaaatga ggttgccaga ttaaagaaat tagttggcga acgccatcac    120
catcaccatc ac                                                       132

<210> SEQ ID NO 3
<211> LENGTH: 262
<212> TYPE: PRT
<213> ORGANISM: Artificial Sequence
<220> FEATURE:
<223> OTHER INFORMATION: 52SR4 ds scFv sequence

<400> SEQUENCE: 3

Asp Ala Val Val Thr Gln Glu Ser Ala Leu Thr Ser Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Trp Tyr Ser Asp
                85                  90                  95

His Trp Val Phe Gly Cys Gly Thr Lys Leu Thr Val Leu Gly Gly Gly
            100                 105                 110

Gly Gly Ser Gly Gly Gly Gly Ser Gly Gly Gly Ser Gly Gly Gly
        115                 120                 125

```
Gly Ser Asp Val Gln Leu Gln Gln Ser Gly Pro Gly Leu Val Ala Pro
    130                 135                 140

Ser Gln Ser Leu Ser Ile Thr Cys Thr Val Ser Gly Phe Leu Leu Thr
145                 150                 155                 160

Asp Tyr Gly Val Asn Trp Val Arg Gln Ser Pro Gly Lys Cys Leu Glu
                165                 170                 175

Trp Leu Gly Val Ile Trp Gly Asp Gly Ile Thr Asp Tyr Asn Ser Ala
                180                 185                 190

Leu Lys Ser Arg Leu Ser Val Thr Lys Asp Asn Ser Lys Ser Gln Val
            195                 200                 205

Phe Leu Lys Met Asn Ser Leu Gln Ser Gly Asp Ser Ala Arg Tyr Tyr
210                 215                 220

Cys Val Thr Gly Leu Phe Asp Tyr Trp Gly Gln Gly Thr Thr Leu Thr
225                 230                 235                 240

Val Ser Ser Ala Ala Ala His His His His His His Glu Gln Lys Leu
                245                 250                 255

Ile Ser Glu Glu Asp Leu
            260
```

<210> SEQ ID NO 4
<211> LENGTH: 792
<212> TYPE: DNA
<213> ORGANISM: Artificial Sequence
<220> FEATURE:
<223> OTHER INFORMATION: DNA encoding SEQ ID NO: 3

<400> SEQUENCE: 4

```
gatgcggtgg tgacccagga aagcgcgctg accagcagcc cgggcgaaac cgtgaccctg      60
acctgccgca gcagcaccgg cgcggtgacc accagcaact atgcgagctg ggtgcaggaa     120
aaaccggatc atctgtttac cggcctgatt ggcggcacca caaccgcgc gccgggcgtg      180
ccggcgcgct tagcggcag cctgattggc gataaagcgg cgctgaccat taccggcgcg      240
cagaccgaag atgaagcgat ttattttgc gtgctgtggt atagcgacca ttgggtgttt      300
ggctgcggca ccaaactgac cgtgctgggt ggaggcggtg gctcaggcgg aggtggctca      360
ggcggtggcg gtctggcgg cggcggcagc gatgtgcagc tgcagcagag cggcccgggc      420
ctggtggcgc cgagccagag cctgagcatt acctgcaccg tgagcggctt tctcctgacc      480
gattatggcg tgaactgggt gcgccagagc ccgggcaaat gcctggaatg gctgggcgtg      540
atttggggcg atggcattac cgattataac agcgcgctga aaagccgcct gagcgtgacc      600
aaagataaca gcaaaagcca ggtgtttctg aaaatgaaca gcctgcagag cggcgatagc      660
gcgcgctatt attgcgtgac cggcctgttt gattattggg gccagggcac caccctgacc      720
gtgagcagcg cggccgccca tcaccatcac catcacgaac agaaactgat tagcgaagaa      780
gatctgtaat ag                                                          792
```

<210> SEQ ID NO 5
<211> LENGTH: 8
<212> TYPE: PRT
<213> ORGANISM: Artificial Sequence
<220> FEATURE:
<223> OTHER INFORMATION: FLEXIBLE PEPTIDE LINKER

<400> SEQUENCE: 5

```
Asp Lys Thr His Thr Cys Ala Ala
1               5
```

```
<210> SEQ ID NO 6
<211> LENGTH: 11
<212> TYPE: PRT
<213> ORGANISM: Artificial Sequence
<220> FEATURE:
<223> OTHER INFORMATION: FLEXIBLE PEPTIDE LINKER

<400> SEQUENCE: 6

Asp Lys Thr His Thr Cys Pro Pro Cys Pro Ala
1               5                   10

<210> SEQ ID NO 7
<211> LENGTH: 18
<212> TYPE: PRT
<213> ORGANISM: Artificial Sequence
<220> FEATURE:
<223> OTHER INFORMATION: FLEXIBLE PEPTIDE LINKER

<400> SEQUENCE: 7

Asp Lys Thr His Thr Cys Pro Pro Cys Pro Ala Thr Cys Pro Pro Cys
1               5                   10                  15

Pro Ala

<210> SEQ ID NO 8
<211> LENGTH: 25
<212> TYPE: PRT
<213> ORGANISM: Artificial Sequence
<220> FEATURE:
<223> OTHER INFORMATION: FLEXIBLE PEPTIDE LINKER

<400> SEQUENCE: 8

Asp Lys Thr His Thr Cys Pro Pro Cys Pro Ala Thr Cys Pro Pro Cys
1               5                   10                  15

Pro Ala Thr Cys Pro Pro Cys Pro Ala
            20                  25

<210> SEQ ID NO 9
<211> LENGTH: 30
<212> TYPE: PRT
<213> ORGANISM: Artificial Sequence
<220> FEATURE:
<223> OTHER INFORMATION: FLEXIBLE PEPTIDE LINKER

<400> SEQUENCE: 9

Asp Lys Thr His Thr Cys Pro Pro Cys Pro Ala Gly Lys Pro Thr Leu
1               5                   10                  15

Tyr Asn Ser Leu Val Met Ser Asp Thr Ala Gly Thr Cys Tyr
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: FLEXIBLE PEPTIDE LINKER

<400> SEQUENCE: 10

Asp Lys Thr His Thr Cys Pro Pro Cys Pro Ala Gly Lys Pro Thr His
1               5                   10                  15

Val Asn Val Ser Val Val Met Ala Glu Val Asp Gly Thr Cys Tyr
            20                  25                  30

<210> SEQ ID NO 11
<211> LENGTH: 15
<212> TYPE: PRT
```

```
<213> ORGANISM: Artificial Sequence
<220> FEATURE:
<223> OTHER INFORMATION: FLEXIBLE PEPTIDE LINKER

<400> SEQUENCE: 11

Asp Lys Thr His Thr Cys Cys Val Glu Cys Pro Pro Cys Pro Ala
1               5                   10                  15

<210> SEQ ID NO 12
<211> LENGTH: 26
<212> TYPE: PRT
<213> ORGANISM: Artificial Sequence
<220> FEATURE:
<223> OTHER INFORMATION: FLEXIBLE PEPTIDE LINKER

<400> SEQUENCE: 12

Asp Lys Thr His Thr Cys Pro Arg Cys Pro Glu Pro Lys Ser Cys Asp
1               5                   10                  15

Thr Pro Pro Pro Cys Pro Arg Cys Pro Ala
            20                  25

<210> SEQ ID NO 13
<211> LENGTH: 11
<212> TYPE: PRT
<213> ORGANISM: Artificial Sequence
<220> FEATURE:
<223> OTHER INFORMATION: FLEXIBLE PEPTIDE LINKER

<400> SEQUENCE: 13

Asp Lys Thr His Thr Cys Pro Ser Cys Pro Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Flexible linker

<400> SEQUENCE: 14

Ser Gly Gly Gly Gly Ser Glu
1               5

<210> SEQ ID NO 15
<211> LENGTH: 6
<212> TYPE: PRT
<213> ORGANISM: Artificial Sequence
<220> FEATURE:
<223> OTHER INFORMATION: Flexible linker

<400> SEQUENCE: 15

Asp Lys Thr His Thr Ser
1               5

<210> SEQ ID NO 16
<211> LENGTH: 6
<212> TYPE: PRT
<213> ORGANISM: Artificial Sequence
<220> FEATURE:
<223> OTHER INFORMATION: Flexible linker

<400> SEQUENCE: 16

Ser Gly Gly Gly Gly Ser
1               5

<210> SEQ ID NO 17
```

```
<211> LENGTH: 11
<212> TYPE: PRT
<213> ORGANISM: Artificial Sequence
<220> FEATURE:
<223> OTHER INFORMATION: Flexible linker

<400> SEQUENCE: 17

Ser Gly Gly Gly Gly Ser Gly Gly Gly Gly Ser
1               5                   10

<210> SEQ ID NO 18
<211> LENGTH: 16
<212> TYPE: PRT
<213> ORGANISM: Artificial Sequence
<220> FEATURE:
<223> OTHER INFORMATION: Flexible linker

<400> SEQUENCE: 18

Ser Gly Gly Gly Gly Ser Gly Gly Gly Gly Ser Gly Gly Gly Gly Ser
1               5                   10                  15

<210> SEQ ID NO 19
<211> LENGTH: 21
<212> TYPE: PRT
<213> ORGANISM: Artificial Sequence
<220> FEATURE:
<223> OTHER INFORMATION: Flexible linker

<400> SEQUENCE: 19

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 20
<211> LENGTH: 26
<212> TYPE: PRT
<213> ORGANISM: Artificial Sequence
<220> FEATURE:
<223> OTHER INFORMATION: Flexible linker

<400> SEQUENCE: 20

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser
            20                  25

<210> SEQ ID NO 21
<211> LENGTH: 11
<212> TYPE: PRT
<213> ORGANISM: Artificial Sequence
<220> FEATURE:
<223> OTHER INFORMATION: Flexible linker

<400> SEQUENCE: 21

Ala Ala Ala Gly Ser Gly Gly Ala Ser Ala Ser
1               5                   10

<210> SEQ ID NO 22
<211> LENGTH: 16
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
```

-continued

```
<223> OTHER INFORMATION: Xaa can be any naturally occurring amino acid

<400> SEQUENCE: 22

Ala Ala Ala Gly Ser Gly Xaa Gly Gly Gly Ser Gly Ala Ser Ala Ser
1               5                   10                  15

<210> SEQ ID NO 23
<211> LENGTH: 21
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 23

Ala Ala Ala Gly Ser Gly Xaa Gly Gly Gly Ser Xaa Gly Gly Gly Ser
1               5                   10                  15

Gly Ala Ser Ala Ser
            20

<210> SEQ ID NO 24
<211> LENGTH: 26
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 24

Ala Ala Ala Gly Ser Gly Xaa Gly Gly Gly Ser Xaa Gly Gly Gly Ser
1               5                   10                  15

Xaa Gly Gly Gly Ser Gly Ala Ser Ala Ser
            20                  25

<210> SEQ ID NO 25
<211> LENGTH: 31
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
```

```
<221> NAME/KEY: misc_feature
<222> LOCATION: (22)..(22)
<223> OTHER INFORMATION: Xaa can be any naturally occurring amino acid

<400> SEQUENCE: 25

Ala Ala Ala Gly Ser Gly Xaa Gly Gly Ser Xaa Gly Gly Ser
1               5                   10                  15

Xaa Gly Gly Gly Ser Xaa Gly Gly Ser Gly Ala Ser Ala Ser
                20                  25                  30

<210> SEQ ID NO 26
<211> LENGTH: 13
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid

<400> SEQUENCE: 26

Ala Ala Ala Gly Ser Gly Xaa Ser Gly Ala Ser Ala Ser
1               5                   10

<210> SEQ ID NO 27
<211> LENGTH: 28
<212> TYPE: PRT
<213> ORGANISM: Artificial Sequence
<220> FEATURE:
<223> OTHER INFORMATION: Flexible linker

<400> SEQUENCE: 27

Pro Gly Gly Asn Arg Gly Thr Thr Thr Thr Arg Arg Pro Ala Thr Thr
1               5                   10                  15

Thr Gly Ser Ser Pro Gly Pro Thr Gln Ser His Tyr
                20                  25

<210> SEQ ID NO 28
<211> LENGTH: 11
<212> TYPE: PRT
<213> ORGANISM: Artificial Sequence
<220> FEATURE:
<223> OTHER INFORMATION: Flexible linker

<400> SEQUENCE: 28

Ala Thr Thr Thr Gly Ser Ser Pro Gly Pro Thr
1               5                   10

<210> SEQ ID NO 29
<211> LENGTH: 6
<212> TYPE: PRT
<213> ORGANISM: Artificial Sequence
<220> FEATURE:
<223> OTHER INFORMATION: Flexible linker

<400> SEQUENCE: 29

Ala Thr Thr Thr Gly Ser
1               5

<210> SEQ ID NO 30
<211> LENGTH: 13
<212> TYPE: PRT
<213> ORGANISM: Artificial Sequence
<220> FEATURE:
<223> OTHER INFORMATION: Flexible linker
```

```
<400> SEQUENCE: 30

Ala Ala Ala Ala Ala Ala Ala Ala Ala Ala Ala
1               5                   10

<210> SEQ ID NO 31
<211> LENGTH: 21
<212> TYPE: PRT
<213> ORGANISM: Artificial Sequence
<220> FEATURE:
<223> OTHER INFORMATION: Flexible linker

<400> SEQUENCE: 31

Glu Pro Ser Gly Pro Ile Ser Thr Ile Asn Ser Pro Pro Ser Lys Glu
1               5                   10                  15

Ser His Lys Ser Pro
            20

<210> SEQ ID NO 32
<211> LENGTH: 15
<212> TYPE: PRT
<213> ORGANISM: Artificial Sequence
<220> FEATURE:
<223> OTHER INFORMATION: Flexible linker

<400> SEQUENCE: 32

Gly Thr Val Ala Ala Pro Ser Val Phe Ile Phe Pro Pro Ser Asp
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Flexible linker

<400> SEQUENCE: 33

Gly Gly Gly Gly Ile Ala Pro Ser Met Val Gly Gly Gly Gly Ser
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Flexible linker

<400> SEQUENCE: 34

Gly Gly Gly Gly Lys Val Glu Gly Ala Gly Gly Gly Gly Gly Ser
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Flexible linker

<400> SEQUENCE: 35

Gly Gly Gly Gly Ser Met Lys Ser His Asp Gly Gly Gly Gly Ser
1               5                   10                  15

<210> SEQ ID NO 36
<211> LENGTH: 15
<212> TYPE: PRT
<213> ORGANISM: Artificial Sequence
<220> FEATURE:
```

<223> OTHER INFORMATION: Flexible linker

<400> SEQUENCE: 36

Gly Gly Gly Gly Asn Leu Ile Thr Ile Val Gly Gly Gly Gly Ser
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Flexible linker

<400> SEQUENCE: 37

Gly Gly Gly Gly Val Val Pro Ser Leu Pro Gly Gly Gly Gly Ser
1               5                   10                  15

<210> SEQ ID NO 38
<211> LENGTH: 12
<212> TYPE: PRT
<213> ORGANISM: Artificial Sequence
<220> FEATURE:
<223> OTHER INFORMATION: Flexible linker

<400> SEQUENCE: 38

Gly Gly Glu Lys Ser Ile Pro Gly Gly Gly Gly Ser
1               5                   10

<210> SEQ ID NO 39
<211> LENGTH: 18
<212> TYPE: PRT
<213> ORGANISM: Artificial Sequence
<220> FEATURE:
<223> OTHER INFORMATION: Flexible linker

<400> SEQUENCE: 39

Arg Pro Leu Ser Tyr Arg Pro Pro Phe Pro Phe Gly Phe Pro Ser Val
1               5                   10                  15

Arg Pro

<210> SEQ ID NO 40
<211> LENGTH: 18
<212> TYPE: PRT
<213> ORGANISM: Artificial Sequence
<220> FEATURE:
<223> OTHER INFORMATION: Flexible linker

<400> SEQUENCE: 40

Tyr Pro Arg Ser Ile Tyr Ile Arg Arg Arg His Pro Ser Pro Ser Leu
1               5                   10                  15

Thr Thr

<210> SEQ ID NO 41
<211> LENGTH: 18
<212> TYPE: PRT
<213> ORGANISM: Artificial Sequence
<220> FEATURE:
<223> OTHER INFORMATION: Flexible linker

<400> SEQUENCE: 41

Thr Pro Ser His Leu Ser His Ile Leu Pro Ser Phe Gly Leu Pro Thr
1               5                   10                  15

Phe Asn

```
<210> SEQ ID NO 42
<211> LENGTH: 18
<212> TYPE: PRT
<213> ORGANISM: Artificial Sequence
<220> FEATURE:
<223> OTHER INFORMATION: Flexible linker

<400> SEQUENCE: 42

Arg Pro Val Ser Pro Phe Thr Phe Pro Arg Leu Ser Asn Ser Trp Leu
1               5                   10                  15

Pro Ala

<210> SEQ ID NO 43
<211> LENGTH: 18
<212> TYPE: PRT
<213> ORGANISM: Artificial Sequence
<220> FEATURE:
<223> OTHER INFORMATION: Flexible linker

<400> SEQUENCE: 43

Ser Pro Ala Ala His Phe Pro Arg Ser Ile Pro Arg Pro Gly Pro Ile
1               5                   10                  15

Arg Thr

<210> SEQ ID NO 44
<211> LENGTH: 18
<212> TYPE: PRT
<213> ORGANISM: Artificial Sequence
<220> FEATURE:
<223> OTHER INFORMATION: Flexible linker

<400> SEQUENCE: 44

Ala Pro Gly Pro Ser Ala Pro Ser His Arg Ser Leu Pro Ser Arg Ala
1               5                   10                  15

Phe Gly

<210> SEQ ID NO 45
<211> LENGTH: 18
<212> TYPE: PRT
<213> ORGANISM: Artificial Sequence
<220> FEATURE:
<223> OTHER INFORMATION: Flexible linker

<400> SEQUENCE: 45

Pro Arg Asn Ser Ile His Phe Leu His Pro Leu Leu Val Ala Pro Leu
1               5                   10                  15

Gly Ala

<210> SEQ ID NO 46
<211> LENGTH: 18
<212> TYPE: PRT
<213> ORGANISM: Artificial Sequence
<220> FEATURE:
<223> OTHER INFORMATION: Flexible linker

<400> SEQUENCE: 46

Met Pro Ser Leu Ser Gly Val Leu Gln Val Arg Tyr Leu Ser Pro Pro
1               5                   10                  15

Asp Leu

<210> SEQ ID NO 47
<211> LENGTH: 18
<212> TYPE: PRT
<213> ORGANISM: Artificial Sequence
```

```
<220> FEATURE:
<223> OTHER INFORMATION: Flexible linker

<400> SEQUENCE: 47

Ser Pro Gln Tyr Pro Ser Pro Leu Thr Leu Thr Leu Pro Pro His Pro
1               5                   10                  15

Ser Leu

<210> SEQ ID NO 48
<211> LENGTH: 18
<212> TYPE: PRT
<213> ORGANISM: Artificial Sequence
<220> FEATURE:
<223> OTHER INFORMATION: Flexible linker

<400> SEQUENCE: 48

Asn Pro Ser Leu Asn Pro Pro Ser Tyr Leu His Arg Ala Pro Ser Arg
1               5                   10                  15

Ile Ser

<210> SEQ ID NO 49
<211> LENGTH: 17
<212> TYPE: PRT
<213> ORGANISM: Artificial Sequence
<220> FEATURE:
<223> OTHER INFORMATION: Flexible linker

<400> SEQUENCE: 49

Leu Pro Trp Arg Thr Ser Leu Leu Pro Ser Leu Pro Leu Arg Arg Arg
1               5                   10                  15

Pro

<210> SEQ ID NO 50
<211> LENGTH: 18
<212> TYPE: PRT
<213> ORGANISM: Artificial Sequence
<220> FEATURE:
<223> OTHER INFORMATION: Flexible linker

<400> SEQUENCE: 50

Pro Pro Leu Phe Ala Lys Gly Pro Val Gly Leu Leu Ser Arg Ser Phe
1               5                   10                  15

Pro Pro

<210> SEQ ID NO 51
<211> LENGTH: 18
<212> TYPE: PRT
<213> ORGANISM: Artificial Sequence
<220> FEATURE:
<223> OTHER INFORMATION: Flexible linker

<400> SEQUENCE: 51

Val Pro Pro Ala Pro Val Val Ser Leu Arg Ser Ala His Ala Arg Pro
1               5                   10                  15

Pro Tyr

<210> SEQ ID NO 52
<211> LENGTH: 17
<212> TYPE: PRT
<213> ORGANISM: Artificial Sequence
<220> FEATURE:
<223> OTHER INFORMATION: Flexible linker

<400> SEQUENCE: 52
```

Leu Arg Pro Thr Pro Pro Arg Val Arg Ser Tyr Thr Cys Cys Pro Thr
1               5                   10                  15

Pro

<210> SEQ ID NO 53
<211> LENGTH: 18
<212> TYPE: PRT
<213> ORGANISM: Artificial Sequence
<220> FEATURE:
<223> OTHER INFORMATION: Flexible linker

<400> SEQUENCE: 53

Pro Asn Val Ala His Val Leu Pro Leu Leu Thr Val Pro Trp Asp Asn
1               5                   10                  15

Leu Arg

<210> SEQ ID NO 54
<211> LENGTH: 18
<212> TYPE: PRT
<213> ORGANISM: Artificial Sequence
<220> FEATURE:
<223> OTHER INFORMATION: Flexible linker

<400> SEQUENCE: 54

Cys Asn Pro Leu Leu Pro Leu Cys Ala Arg Ser Pro Ala Val Arg Thr
1               5                   10                  15

Phe Pro

<210> SEQ ID NO 55
<211> LENGTH: 11
<212> TYPE: PRT
<213> ORGANISM: Artificial Sequence
<220> FEATURE:
<223> OTHER INFORMATION: Linker

<400> SEQUENCE: 55

Asp Leu Cys Leu Arg Asp Trp Gly Cys Leu Trp
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Linker

<400> SEQUENCE: 56

Asp Ile Cys Leu Pro Arg Trp Gly Cys Leu Trp
1               5                   10

<210> SEQ ID NO 57
<211> LENGTH: 15
<212> TYPE: PRT
<213> ORGANISM: Artificial Sequence
<220> FEATURE:
<223> OTHER INFORMATION: Linker

<400> SEQUENCE: 57

Met Glu Asp Ile Cys Leu Pro Arg Trp Gly Cys Leu Trp Gly Asp
1               5                   10                  15

<210> SEQ ID NO 58
<211> LENGTH: 20
<212> TYPE: PRT

```
<213> ORGANISM: Artificial Sequence
<220> FEATURE:
<223> OTHER INFORMATION: Linker

<400> SEQUENCE: 58

Gln Arg Leu Met Glu Asp Ile Cys Leu Pro Arg Trp Gly Cys Leu Trp
1               5                   10                  15

Glu Asp Asp Glu
            20

<210> SEQ ID NO 59
<211> LENGTH: 20
<212> TYPE: PRT
<213> ORGANISM: Artificial Sequence
<220> FEATURE:
<223> OTHER INFORMATION: Linker

<400> SEQUENCE: 59

Gln Gly Leu Ile Gly Asp Ile Cys Leu Pro Arg Trp Gly Cys Leu Trp
1               5                   10                  15

Gly Arg Ser Val
            20

<210> SEQ ID NO 60
<211> LENGTH: 21
<212> TYPE: PRT
<213> ORGANISM: Artificial Sequence
<220> FEATURE:
<223> OTHER INFORMATION: Linker

<400> SEQUENCE: 60

Gln Gly Leu Ile Gly Asp Ile Cys Leu Pro Arg Trp Gly Cys Leu Trp
1               5                   10                  15

Gly Arg Ser Val Lys
            20

<210> SEQ ID NO 61
<211> LENGTH: 15
<212> TYPE: PRT
<213> ORGANISM: Artificial Sequence
<220> FEATURE:
<223> OTHER INFORMATION: Linker

<400> SEQUENCE: 61

Glu Asp Ile Cys Leu Pro Arg Trp Gly Cys Leu Trp Glu Asp Asp
1               5                   10                  15

<210> SEQ ID NO 62
<211> LENGTH: 18
<212> TYPE: PRT
<213> ORGANISM: Artificial Sequence
<220> FEATURE:
<223> OTHER INFORMATION: Linker

<400> SEQUENCE: 62

Arg Leu Met Glu Asp Ile Cys Leu Pro Arg Trp Gly Cys Leu Trp Glu
1               5                   10                  15

Asp Asp

<210> SEQ ID NO 63
<211> LENGTH: 16
<212> TYPE: PRT
<213> ORGANISM: Artificial Sequence
<220> FEATURE:
<223> OTHER INFORMATION: Linker
```

<400> SEQUENCE: 63

Met Glu Asp Ile Cys Leu Pro Arg Trp Gly Cys Leu Trp Glu Asp Asp
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Linker

<400> SEQUENCE: 64

Met Glu Asp Ile Cys Leu Pro Arg Trp Gly Cys Leu Trp Glu Asp
1               5                   10                  15

<210> SEQ ID NO 65
<211> LENGTH: 18
<212> TYPE: PRT
<213> ORGANISM: Artificial Sequence
<220> FEATURE:
<223> OTHER INFORMATION: Linker

<400> SEQUENCE: 65

Arg Leu Met Glu Asp Ile Cys Leu Ala Arg Trp Gly Cys Leu Trp Glu
1               5                   10                  15

Asp Asp

<210> SEQ ID NO 66
<211> LENGTH: 20
<212> TYPE: PRT
<213> ORGANISM: Artificial Sequence
<220> FEATURE:
<223> OTHER INFORMATION: Linker

<400> SEQUENCE: 66

Glu Val Arg Ser Phe Cys Thr Arg Trp Pro Ala Glu Lys Ser Cys Lys
1               5                   10                  15

Pro Leu Arg Gly
            20

<210> SEQ ID NO 67
<211> LENGTH: 20
<212> TYPE: PRT
<213> ORGANISM: Artificial Sequence
<220> FEATURE:
<223> OTHER INFORMATION: Linker

<400> SEQUENCE: 67

Arg Ala Pro Glu Ser Phe Val Cys Tyr Trp Glu Thr Ile Cys Phe Glu
1               5                   10                  15

Arg Ser Glu Gln
            20

<210> SEQ ID NO 68
<211> LENGTH: 11
<212> TYPE: PRT
<213> ORGANISM: Artificial Sequence
<220> FEATURE:
<223> OTHER INFORMATION: Linker

<400> SEQUENCE: 68

Glu Met Cys Tyr Phe Pro Gly Ile Cys Trp Met
1               5                   10

```
<210> SEQ ID NO 69
<211> LENGTH: 11
<212> TYPE: PRT
<213> ORGANISM: Artificial Sequence
<220> FEATURE:
<223> OTHER INFORMATION: peptide sequence

<400> SEQUENCE: 69

Gly Ala Pro Ala Pro Ala Ala Pro Ala Pro Ala
1               5                   10

<210> SEQ ID NO 70
<211> LENGTH: 4
<212> TYPE: PRT
<213> ORGANISM: Artificial Sequence
<220> FEATURE:
<223> OTHER INFORMATION: peptide sequence

<400> SEQUENCE: 70

Pro Pro Pro Pro
1

<210> SEQ ID NO 71
<211> LENGTH: 6
<212> TYPE: PRT
<213> ORGANISM: Artificial Sequence
<220> FEATURE:
<223> OTHER INFORMATION: Linker

<400> SEQUENCE: 71

Ala Ser Gly Gly Gly Gly
1               5

<210> SEQ ID NO 72
<211> LENGTH: 8
<212> TYPE: PRT
<213> ORGANISM: Artificial Sequence
<220> FEATURE:
<223> OTHER INFORMATION: Linker

<400> SEQUENCE: 72

Ala Ser Gly Gly Gly Gly Ser Gly
1               5
```